United States Patent [19]

Bundy

[11] 3,987,087

[45] Oct. 19, 1976

[54] PHENYL-SUBSTITUTED PROSTAGLANDIN-F TYPE ANALOGS

[75] Inventor: Gordon L. Bundy, Portage, Mich.

[73] Assignee: The Upjohn Company, Kalamazoo, Mich.

[22] Filed: Jan. 7, 1974

[21] Appl. No.: 431,011

Related U.S. Application Data

[63] Continuation-in-part of Ser. No. 167,446, July 29, 1971, abandoned, which is a continuation-in-part of Ser. No. 86,303, Nov. 2, 1970, abandoned.

[52] U.S. Cl............................. 260/410.9; 424/305; 424/308; 260/240 R; 260/340.9; 260/343.6; 260/408; 260/410; 260/410.5; 260/413; 260/456 R; 260/468 D; 260/473 A; 260/473 R; 260/520 B; 260/586 R
[51] Int. Cl.$^2$........................................ C07C 49/28
[58] Field of Search........ 260/240 R, 468 G, 473 R, 260/473 A, 520 B

[56] References Cited
UNITED STATES PATENTS

| | | | |
|---|---|---|---|
| 3,505,386 | 4/1970 | Babcock et al.................. | 260/468 D |
| 3,524,867 | 8/1970 | Beal et al..................... | 260/468 D X |
| 3,671,570 | 6/1972 | Bagli et al...................... | 260/473 A |
| 3,678,092 | 7/1972 | Finch............................. | 260/473 A |
| 3,679,705 | 7/1972 | Babcock et al............. | 260/468 D X |
| 3,767,695 | 10/1973 | Pike et al........................ | 260/468 D |

*Primary Examiner*—John D. Randolph
*Attorney, Agent, or Firm*—Morris L. Nielsen

[57] ABSTRACT

This invention is a group of phenyl-substituted PGE-type, PGF-type, PGA-type and PGB-type compounds, and processes for making them. These compounds are useful for a variety of pharmacological purposes, including anti-ulcer, inhibition of platelet aggregation, increase of nasal patency, labor inducement at term, and wound healing.

260 Claims, No Drawings

PHENYL-SUBSTITUTED PROSTAGLANDIN-F TYPE ANALOGS

CROSS REFERENCE TO RELATED APPLICATIONS

This application is a continuation-in-part of my copending application Ser. No. 167,446, filed July 29, 1971, now abandoned, which in turn is a continuation-in-part of my application Ser. No. 86,303 filed Nov. 2, 1970, now abandoned.

DESCRIPTION OF THE INVENTION

This invention relates to compositions of matter, and to methods and intermediates for producing them. The several aspects of this invention relate to novel analogs of some of the known prostaglandins, for example, prostaglandin $E_1$ ($PGE_1$), prostaglandin $E_2$ ($PGE_2$), prostaglandin $F_1$ ($PGF_{1\alpha}$ and $PGF_{1\beta}$), prostaglandin $F_2$ ($PGF_{2\alpha}$ and $PGF_{2\beta}$), prostaglandin $A_1$ ($PGA_1$), prostaglandin $A_2$ ($PGA_2$), prostaglandin $B_1$ ($PGB_1$), prostaglandin $B_2$ ($PGB_2$), and the dihydro derivatives of $PGE_1$, $PGF_{1\alpha}$, $PGF_{1\beta}$, $PGA_1$, and $PGB_1$, to novel methods for producing those novel prostaglandin analogs, and to novel chemical intermediates useful in those novel methods. In particular, the novel prostaglandin analogs of this invention are phenyl-substituted in the C-13 to C-20 chain.

Each of the above-mentioned known prostaglandins is a derivative of prostanoic acid which has the following structure and atom numbering:

A systematic name for prostanoic acid is 7-[(2β-octyl)-cyclopent-1α-yl]heptanoic acid.

$PGE_1$ has the following structure:

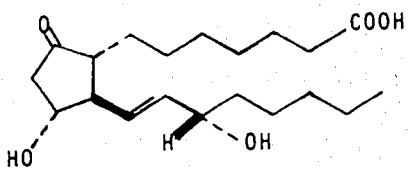

$PGF_{1\alpha}$ has the following structure:

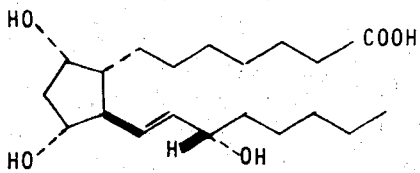

$PGF_{1\beta}$ has the following structure:

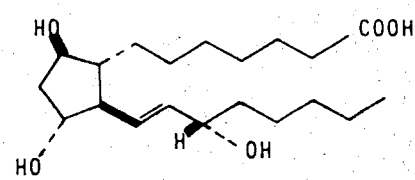

$PGA_1$ has the following structure:

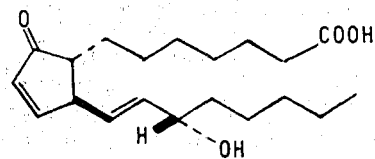

$PGB_1$ has the following structure:

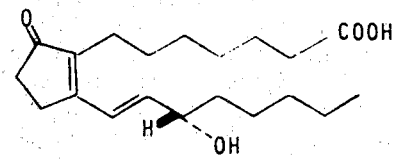

Each of the known prostaglandins $PGE_2$, $PGF_{2\alpha}$, $PGF_{2\beta}$, $PGA_2$, and $PGB_2$ has a structure the same as that shown for the corresponding $PG_1$ compound except that, in each, C-5 and C-6 are linked with a cis carbon-carbon double bond. For example, $PGE_2$ has the following structure:

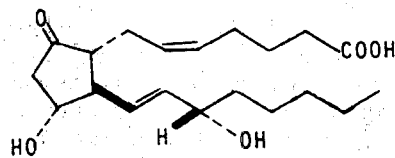

Each 13,14-dihydro derivative of $PGE_1$, $PGF_{1\alpha}$, $PGF_{1\beta}$, $PGA_1$, and $PGB_1$ has a structure the same as that shown for the corresponding $PG_1$ compound except that in each, C-13 and C-14 are linked with a carbon-carbon single bond. For example, 13,14-dihydro-$PGE_1$ has the following structure:

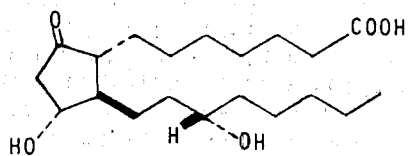

The prostaglandin formulas mentioned above each have several centers of asymmetry. As drawn, each formula represents the particular optically active form of the prostaglandin obtained from certain mammalian tissues, for example, sheep vesicular glands, swine lung, and human seminal plasma, or by reduction or dehydration of a prostaglandin so obtained. See, for example, Bergstrom et al., Pharmacol. Rev. 20, 1 (1968), and references cited therein. The mirror image of each formula represents a molecule of the enantiomer of that prostaglandin. The racemic form of the prostaglandin consists of equal numbers of two types of molecules, one represented by one of the above formulas and the other represented by the mirror image of that formula. Thus, both formulas are needed to define a racemic prostaglandin. See Nature 212, 38 (1968) for discussion of the stereochemistry of the prostaglandins. For convenience hereinafter, use of the terms $PGF_1$, $PGF_{1\alpha}$, and the like, will means the optically active form of that prostaglandin with the same absolute configuration as PGE$_1$ obtained from mammalian tissues. When reference to the racemic form of either of these prostaglandins is intended, either the word racemic or the prefix dl will precede the prostaglandin name, thus, racemic PGE$_1$ or dl-PGF$_{1\alpha}$ and the like.

In the formulas given above, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

Prostaglandins with carboxyl-terminated side chains attached to the cyclopentane ring in beta configuration are also known. These are derivatives of 8-iso-prostanoic acid which has the following formula:

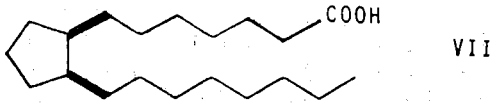

VII

A systematic name for 8-iso-prostanoic acid is 7-[(2β-octyl)-cyclopent-1β-yl]heptanoic acid.

PGE$_1$, PGE$_2$, dihydro-PGE$_1$, and the corresponding PGF$_\alpha$, PGF$_\beta$, PGA, and PGB compounds, and their esters, acylates, and pharmacologically acceptable salts, are extremely potent in causing various biological responses. For that reason, these compounds are useful for pharmacological purposes. See, for example, Bergstrom et al., Pharmacol. Rev. 20, 1 (1968), and references cited therein. A few of those biological responses are stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; controlling spasm and facilitating breathing in asthmatic conditions; decreasing blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE and PGB compounds, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 μg. to about 10 mg. per ml. of a pharmacologically suitable liquid vehicle or as an aerosol spray, both for topical application.

The PGE, PGF$_\alpha$, PGF$_\beta$, and PGA compounds are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such a sympathomimetics (isoproterenol, phenylephrine, ephedrine, etc); xanthine derivatives (theophylline and aminophylline); and corticosteroids (ACTH and prednisolone). Regarding use of these compounds see South African Pat. No. 681 055.

The PGE and PGA compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, PGF$_\alpha$, and PGF$_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, PGF$_\alpha$, and PGF$_\beta$ compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in a single or multiple portions to the circulating blood, to the blood of the donor animal, to the perfused body portion, attached or detached, to the recipient, or to two or all of those at a total steady state dose of about .001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, $PGE_2$, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 $\mu$g. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact does depending on the age, weight, and condition of the patient or animal.

The PGE, $PGF_\alpha$, and $PGF_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50$\mu$g. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGE, $PGF_\alpha$, and $PGF_\beta$ compounds are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose, $PGF_{2\alpha}$, for example, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

The PGE and PGF compounds are useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by PGE and PGF compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the PGE and PGF compounds are administered locally or systemically. $PGF_2$, for example, is administered orally or vaginally at doses of about 5 to 50 mg. per treatment of an adult female human, with from one to five treatments per 24 hour period. $PGE_2$ is also administered intramuscularly or subcutaneously at doses of about one to 25 mg. per treatment. The exact dosages for these purposes depend on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGA compounds and derivatives and salts thereof increase the flow of blood in the mammalian kidney, thereby increasing volume and electrolyte content of the urine. For that reason, PGA compounds are useful in managing cases of renal dysfunction, especially those involving blockage of the renal vascular bed. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 $\mu$g. per kg. of body weight or by intravenous infusion at a dose in the range 0.1 to 20 $\mu$g. per kg. of body weight per minute until the desired effect is obtained. Subsequent doses are given by intravenous, intramuscular, or subcutaneous injection or infusion in the range 0.05 to 2 mg. per kg. of body weight per day.

The PGE and PGB compounds promote and accelerate the growth of epidermal cells and keratin in animals, including humans, useful domestic animals, pets, zoological specimens, and laboratory animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 μg./ml. of the PGB compound or several times that concentration of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

SUMMARY OF THE INVENTION

It is the purpose of this invention to provide novel prostaglandin analogs, and processes for making them.

The novel prostaglandin analogs of this invention each have a benzene ring as part of the C-13 to C-20 chain of the prostanoic acid structure (I) acid or 8-isoprostanoic acid structure (VII). That benzene ring is present as a substituted or unsubstituted phenyl moiety (1) attached as a substituent replacing one of the hydrogens on one of the methylenes between C-15 and the terminal methyl of the prostanoic acid or 8-isoprostanoic acid structure or (2) attached to the terminal or omega carbon of the C-16 to C-20 portion of the chain, replacing either (a) one of the hydrogens of the terminal methyl, (b) the entire terminal methyl, or (c) the terminal methyl plus one to four of the methylenes adjacent to that terminal methyl. For example, three of the novel prostaglandin analogs of this invention are represented by the formulas:

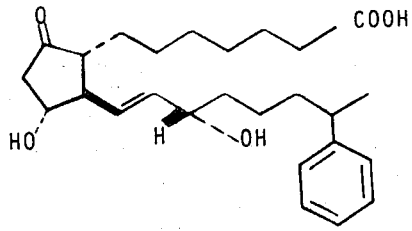

VIII

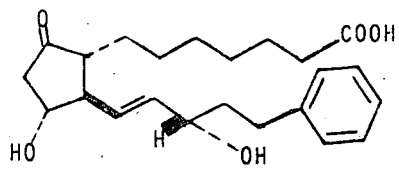

IX

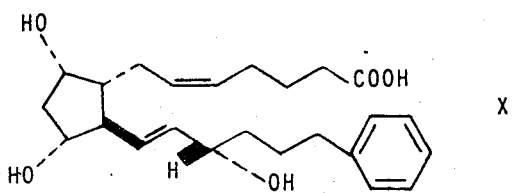

X

Based upon its relationship to $PGE_1$ and prostanoic acid, the compound of Formula VIII is named 19-phenyl-$PGE_1$, that of Formula IX is named 17-phenyl-18,19,20-trinor-$PGE_1$, and that of Formula X is named 18-phenyl-19,20-dinor-$PGF_{2\alpha}$. In Formulas IX and X, trinor and dinor indicate absence of the terminal -$CH_2$-$CH_2$-$CH_3$ and the terminal -$CH_2$-$CH_3$, respectively, of $PGE_1$ and $PGF_{2\alpha}$. The words nor, dinor, trinor, tetranor, and pentanor in the names given here and hereinafter for novel prostaglandins of this invention are to be construed as indicating the number of carbon atoms, i.e. one, 2, 3, 4 or 5, missing from the C-16 to C-20 position of the prostanoic acid carbon skeleton. The phenyl or substituted phenyl moiety is attached to the remaining portion of the prostanoic acid skeleton, i.e., to C-19 for the nor-compounds, to C-18 for the dinor compounds, to C-17 for the trinor compounds, to C-16 for the tetranor compounds, and to C-15 for the pentanor compounds. In addition, the term can include carbon atoms missing from the C-1 to C-7 position of the prostanoic acid skeleton, for example, 17-phenyl-2,18,19,20-tetranor $PGF_{2\alpha}$.

Some of the novel prostaglandin analogs of this invention differ structurally in other ways from the known prostanoic acid derivatives, having, for example, more or fewer carbon atoms in the C-1 to C-7 chain of prostanoic acid, and having one or more alkyl and/or fluoro substituents in that chain or in the C-13 to C-20 chain of prostanoic acid.

Each of the novel phenyl-substituted prostaglandin analogs of this invention is encompassed by one of the following formulas or by the combination of that formula and its mirror image:

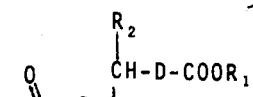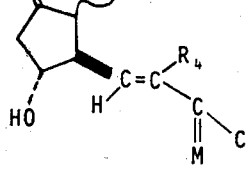
XI
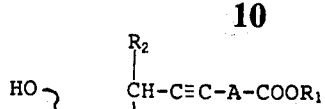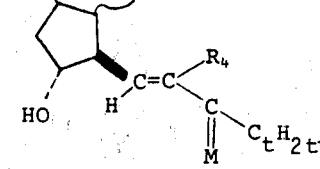
XVII
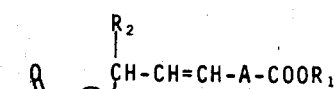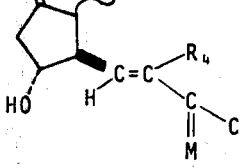
XII
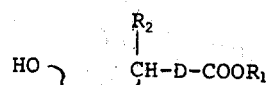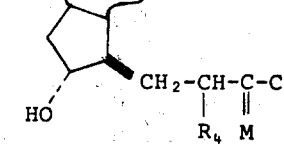
XVIII
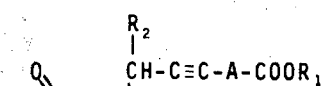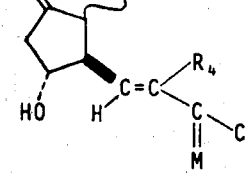
XIII
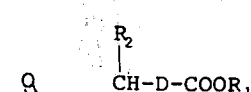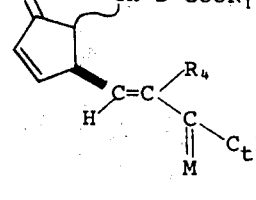
XIX
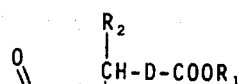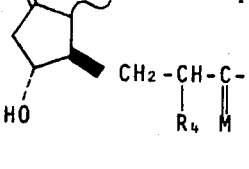
XIV
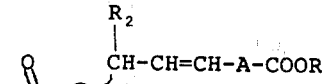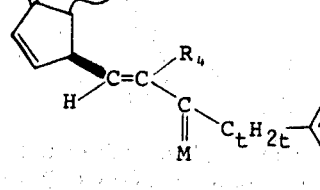
XX
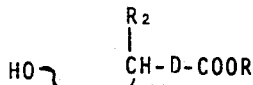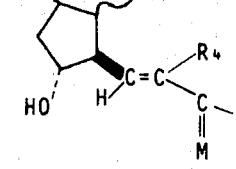
XV
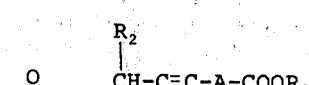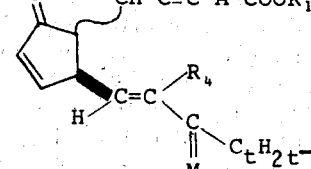
XXI
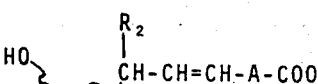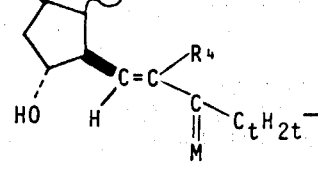
XVI
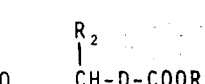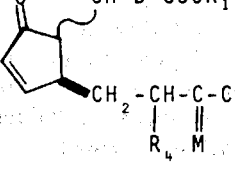
XXII

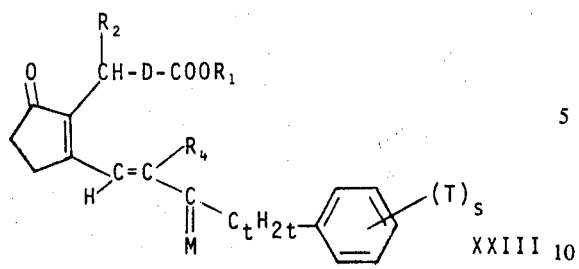

XXIII

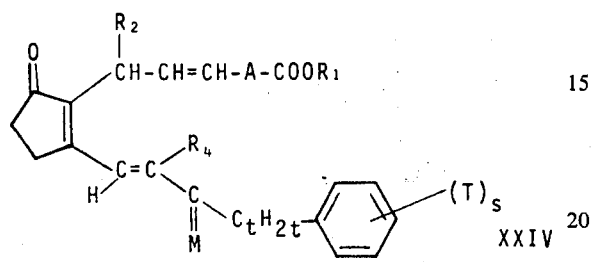

XXIV

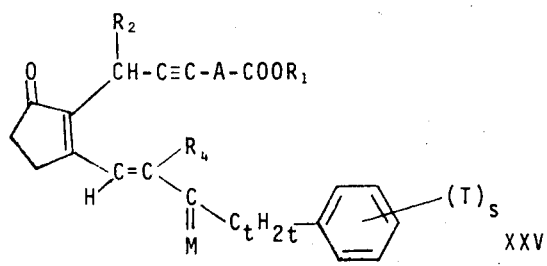

XXV

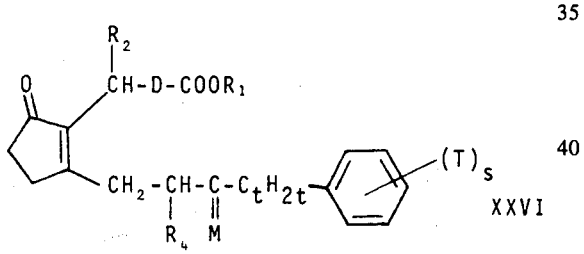

XXVI

Formulas XI to XIV represent phenyl-substituted compounds of the PGE type. Formulas XV to XVIII represent phenyl-substituted compounds of the PGF type. Formulas XIX to XXII represent phenyl-substituted compounds of the PGA type. Formulas XXIII to XXVI represent phenyl-substituted compounds of the PGB type.

In Formulas XI to XXVI, $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2 or 3 chloro or alkyl of one to 4 carbon atoms, inclusive, or ethyl substituted in the β-position with 3 chloro, 2 or 3 bromo, or 1, 2, or 3 iodo. M is

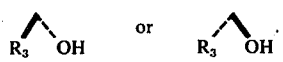

$R_2$, $R_3$, and $R_4$ are hydrogen or alkyl of one to 4 carbon atoms, inclusive. The moiety $-C_tH_{2t}-$ represents (a) a valence bond or (b) alkylene of one to 10 carbon atoms, inclusive, substituted with zero, one, or 2 fluoro, with one to 7 carbon atoms, inclusive, between

and the ring. When one or 2 fluoro are present as substituents of $-C_tH_{2t}$, that moiety will contain $2t$-1 or $2t$-2 hydrogen atoms, respectively, rather than $2t$ hydrogen atoms. The symbol T represents alkyl of one to 4 carbon atoms, inclusive, fluoro, chloro, trifluoromethyl, or $-OR_9$, wherein $R_9$ is hydrogen or alkyl of one to 4 carbon atoms, inclusive. The symbol s represents zero, one, 2, or 3. Regarding the combination $(T)_s$ attached to the phenyl ring, no more than two T's are other than alkyl. Except for that proviso, when two or three T's are present as substituents, they are the same or different. The symbol D represents alkylene of 3 to 12 carbon atoms, inclusive, substituted with zero, one, 2, 3, or 4 fluoro, with 3 to 7 carbon atoms, inclusive, between $-CHR_2-$ and $COOR_1$, and with the proviso that when 3 or 4 fluoro are present, they are all substituents of the carbon atoms alpha and beta to $COOR_1$. The symbol A represents alkylene of one to 10 carbon atoms, inclusive, substituted with zero, one, 2, 3, or 4 fluoro, with one to 5 carbon atoms, inclusive, between =CH- or ≡C- and $-COOR_1$, and with the proviso that when 3 or 4 fluoro are present, they are all substituents of the carbon atoms alpha and beta to $-COOR_1$.

The wavy line ~ in Formulas XI to XXII indicates attachment of the hydroxyl or the side chain to the cyclopentane ring in alpha or beta configuration. In the case of the compounds of Formulas XV to XVIII, there are two wavy lines, and those formulas encompass compounds wherein the configurations of the hydroxyl and the carboxyl-terminated moieties are, respectively, α,α, α,β, β,α, and β,β.

Formulas XI to XXVI include the separate isomers wherein M is either

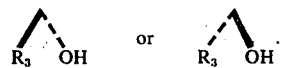

i.e. where the side chain hydroxy is in either S (alpha) or R (epi or beta) configuration. Referring to the prostanoic acid atom numbering (formula I above), the point of attachment corresponds to C-15, and, herein regardless of the variation in the C-1 to C-7 carbon chain, these epimers are referred to as C-15 epimers.

Formulas XV – XVIII wherein the C-9 hydroxyl (following the prostanoic acid numbering) is attached to the cyclopentane ring with a wavy line ~ include both PGF α - and PGF β -type compounds.

Included in Formulas XII, XVI, XX, and XXIV are both the cis and the trans compounds with respect to the C-5 to C-6 carbon-carbon double bond in the carboxyl-terminated side chain. In all of the compounds containing the C-13 to C-14 double bond, that carbon-carbon double bond is in trans configuration, and the chain containing $R_4$ is attached to the cyclopentane ring in beta configuration in compounds encompassed by Formulas XI to XXII.

Formulas XI to XXVI include lower alkanoates, and also pharmacologically aceptable salts when $R_1$ is hydrogen.

Like the natural prostaglandins described above, these novel phenyl-substituted prostaglandin compounds have several centers of asymmetry. The novel compounds of this invention include (a) compounds having the same configuration as naturally occurring prostaglandins and (b) racemic compounds of (a) plus optically active enantiomeric forms thereof. As discussed hereinabove, two structural formulas are required to define accurately these racemic compounds. Formulas XI through XXVI, inclusive, are intended to represent optically active prostanoic acid analogs having the same absolute configuration as the naturally-occurring prostaglandins. However, for convenience in the charts herein only a single formula is used to define not only the optically active form but also the racemic compounds which generally undergo the same reactions.

Formula XI represents 17-phenyl-18,19,20-trinor-$PGE_1$ (Formula IX above) when $R_1$, $R_2$, $R_3$, and $R_4$ are each hydrogen, D is pentamethylene, $C_tH_{2t}$ is ethylene ($t$ is 2), $s$ is zero, the carboxyl-terminated side chain is attached to the cyclopentane ring in alpha configuration, and the configuration of the hydroxy in the

group is alpha (S).

With regard to Formulas XI to XXVI, examples of alkyl of one to 4 carbon atoms, inclusive, are methyl, ethyl, propyl, butyl, and isomeric forms thereof. Examples of alkyl of one to 10 carbon atoms, inclusive, are those given above, and pentyl, hexyl, heptyl, octyl, nonyl, decyl and isomeric forms thereof. Examples of alkyl of one to 12 carbon atoms, inclusive, are those given above, and undecyl, dodecyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 3-pentylcyclopentyl, 3tert-butylcyclopentyl, cyclohexyl, 4-tert-butylcyclohexyl, 3isopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive are p-chlorophenyl, m-chlorophenyl, o-chlorophenyl, 2,4,-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of alkylene within the various scopes of $-C_tH_{2t}-$, D, and A, as those are defined above, are methylene, ethylene, trimethylene, tetramethylene, pentamethylene, hexamethylene, and heptamethylene, those alkylenes with one or more alkyl substituents on one or more carbon atoms thereof, e.g., $-CH(CH_3)-$, $-C(CH_3)_2-$, $-CH(CH_2CH_3)-$, $-CH_2-CH(CH_3)-$, $-CH(CH_3)-CH(CH_3)-$, $-CH_2-C(CH_3)_2-$, $-CH_2-CH(CH_3)-CH_2-$, $-CH_2-CH_2-CH(CH_2CH_3)-$, $-CH(CH_3)-CH(CH_3)-CH_2-CH_2-$, $-CH_2-CH_2-CH_2-C(CH_3)_2-CH_2-$, $-CH_2-CH_2-CH_2-CH_2-CH(CH_3)-$, $-CH_2-CH_2-CH_2-CH_2-C(CH_3)_2-$, $-CH(CH_3)-CH_2-CH(CH_3)-CH_2-CH_2-CH(CH_3)-$, and $-CH_2-CH_2-CH_2-CH_2-CH_2-CH_2-C(CH_3)_2-$.

Examples of alkylene substituted with one or 2 fluoro in the case of $C_tH_{2t}$, and with one, 2, 3, or 4 fluoro in the case of D and A, e.g., $-CHF-CH_2-$, $-CHF-CHF-$, $-CH_2-CH_2-CF_2-$, $-CH_2-CHF-CH_2-$, $-CH_2-CH_2-CF(CH_3)-$, $-CH_2-CH_2-CF_2-CF_2-$, $-CH(CH_3)-CH_2-CH_2-CHF-CF_2-$, $CH_2-CH_2-CH_2-CH_2-CH_2-CF_2-$, and $-CH_2-CH_2-CH_2-CH_2-CH_2-CF_2-CF_2-$.

Examples of

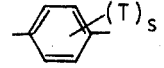

as defined above are phenyl, p-tolyl, m-tolyl, o-tolyl, p-fluorophenyl, m-fluorophenyl, o-fluorophenyl, p-chlorophenyl, m-chlorophenyl, o-chlorophenyl, p-trifluoromethylphenyl, m-trifluoromethylphenyl, o-trifluoromethylphenyl, p-hydroxyphenyl, m-hydroxyphenyl, o-hydroxyphenyl, p-methoxyphenyl, m-methoxyphenyl, o-methoxyphenyl, o-ethylphenyl, m-isopropylphenyl, p-tert-butylphenyl, p-butoxyphenyl, 3,4-dimethylphenyl, 2,4-diethylphenyl, 2,4,6-trimethylphenyl, 3,4,5-trimethylphenyl, 2,4-dichlorophenyl, 3,4-difluorophenyl, 2-chloro-4-methylphenyl, 2-fluoro-4-methoxyphenyl, 3,5-dimethyl-4-fluorophenyl, 2,6-dimethyl-4-hydroxyphenyl, and 2,4di(trifluoromethyl)-phenyl.

The novel Formula XI - XIV PGE-type, Formula XV - XVIII PGF$_\alpha$ -type and PGF$_\beta$ -type, Formula XIX - XXII PGA-type and Formula XXIII - XXVI PGB-type phenyl-substituted prostaglandins each cause the same biological responses described above for the PGE, PGF$_\alpha$ , PGF$_\beta$ , PGA, and PGB compounds, respectively. Each of these novel compounds is accordingly useful for the above-described corresponding purposes, and is used for those purposes in the same manner as described above.

The known PGE, PGF$_\alpha$ , PGF$_\beta$ , PGA, and PGB compounds uniformly cause multiple biological responses even at low doses. For example, $PGE_1$ and $PGE_2$ both cause vasodepression and smooth muscle stimulaton, and at the same time they exert antilipolytic activity. Moreover, for many applications, these known prostaglandins have an inconveniently short duration of biological activity. In striking contrast, the novel Formula XI-to-XXVI compounds are substantially more specific with regard to potency in causing prostaglandin-like biological responses, and have a substantially longer duration of biological activity. Therefore, each of these novel prostaglandin analogs is useful in place of one of the corresponding above-mentioned known prostaglandins for at least one of the pharmacological purposes indicated above for the latter, and is surprisingly and unexpectedly more useful because it has a different and narrower spectrum of biological activity than the known prostaglandins, and therefore is more specific in its activity and causes smaller and fewer undesired side effects than the known prostaglandin. Moreover, because of its prolonged activity, fewer and smaller doses of the novel prostaglandin analog can frequently be used to attain the desired result.

To obtain the optimum combination of biological response specificity, potency, and duration of activity, certain compounds within the scope of Formulas XI to XXVI are preferred. For example, it is preferred that the carboxy-terminated chain in each formula contain a chain of five or six atoms between the carboxy and the cyclopentane ring. Accordingly and with reference to Formulas XI to XXVI, it is preferred that D represents either a 4- or 5-carbon divalent chain, especially a 5-carbon divalent chain, and that A represents a 2- or 3-carbon divalent chain, especially a 3-carbon divalent chain. These preferences do not exclude additional carbon atoms (alkyl groups) as branching.

Another preference for the carboxy-terminated chain in Formulas XI to XXVI is that D be $-(CH_2)_a-X-$ and A be $-(CH_2)_b-X-$, wherein $a$ is one, 2, 3, 4, or 5, $b$ is zero, one, 2, or 3, and X is ethylene substituted by one, 2, 3, or 4 fluoro, methyl, or ethyl, or by one alkyl of 3 or 4 carbon atoms. Examples of X so defined are $-CH_2-CHF-$, $CHF-CH_2-$, $-CHF-CF_2-$, $-CF_2-CH_2-$, $-CHF-CHF-$, $-CHF-CF_2-$, $-CF_2-CHF-$, $-CF_2-CF_2-$, $-CH_2-CH(CH_3)-$, $-CH(CH_3)-CH_2-$, $-CH_2-C(CH_3)_2-$, $-C(CH_3)_2-CH_2-$, $-CH(CH_3)-CH(CH_3)-$, and similarly for ethyl and the several combinations of methyl and ethyl, methyl and fluoro, ethyl and fluoro, and a single propyl, isopropyl, butyl, isobutyl, sec-butyl, and tert-butyl on either carbon atom of X. Especially preferred among these substituted compounds are those wherein $a$ is 3 and $b$ is one, those containing 7-carbon carboxy-terminated side chains.

Another preference for the compounds of Formulas XI to XXVI is that $R_2$, $R_3$, and $R_4$ be hydrogen or methyl. All of those R groups can be hydrogen, all can be methyl, or there can be any of the possible combinations of hydrogen and methyl. Especially preferred are compounds in which $R_3$ is methyl.

Another preference for the compounds of Formulas XI to XXVI is that $-C_tH_{2t}$ be a chain of one to 4 carbon atoms, either branched, e.g. with one or two alkyl substituents on C-16 (the carbon adjacent to the hydroxy-substituted carbon) wherein alkyl has one to 4 carbon atoms, inclusive, especially $-CH_3$, or straight-chain alkylene, i.e., $-(CH_2)_d-$ wherein $d$ is one, 2, 3, or 4, with or without a fluoro substituent on C-16, e.g., $-CHF-(CH_2)_g-$ wherein $g$ is zero, one, 2, or 3. It is also preferred that the phenyl ring, when substituted, i.e., $s$ is not zero, be substituted at least at the para position.

Another advantage of the novel compounds of this invention, especially the preferred compounds defined hereinabove, compared with the known prostaglandins, is that these novel compounds are administered effectively orally, sublingually, intravaginally, buccally, or rectally, in addition to the usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

The phenyl-substituted PGE, PGF$_\alpha$, PGF$_\beta$, PGA, and PGB type compounds encompassed by Formulas XI to XXVI including the special classes of compounds described above, are used for the purposes described above in the free acid form, in ester form, or in pharmacologically acceptable salt form. When the ester form is used, the ester is any of those within the above definition of $R_1$. However, it is preferred that the ester be alkyl of one to twelve carbon atoms, inclusive. Of those alkyl, methyl and ethyl are especially preferred for optimum absorption of the compound by the body or experimental animal system and straight-chain octyl, nonyl, decyl, undecyl and dodecyl are especially preferred for prolonged activity in the body or experimental animal.

Pharmacologically acceptable salts of these Formula XI-to-XXVI compounds useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The phenyl-substituted PGE, PGF$_\alpha$, PGF$_\beta$, PGA, and PGB type compounds encompassed by Formulas XI to XXVI including the special classes of compounds described above, are also used for the purposes described above either in free hydroxy form or in the form wherein the hydroxy moieties are transformed to lower alkanoate moieties, e.g., -OH to -OCOCH$_3$. Examples of lower alkanoate moieties are acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

As discussed above, the compounds of formulas XI to XXVI are administered in various ways for various purposes, e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred.

For that purpose, it is preferred because of increased water solubility that $R_1$ in the Formula XI-to-XXVI compounds be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used.

The phenyl-substituted PGE, PGF$_\alpha$, PGF$_\beta$, PGA and PGB compounds encompassed by Formulas XI to XXVI are produced by the reactions and procedures described and exemplified hereinafter.

Reference to Chart A will make clear the various transformations of phenyl-substituted PGE-type compounds of Formulas XI to XIV to the corresponding PGF$_\alpha$, PFG$_\beta$, PGA, and PGB type compounds. Therein, E is -CH$_2$CHR$_4$- or trans-CH=CR$_4$-, Q is

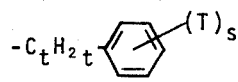

and V is either D, -CH=CH-A- (cis or trans), or -C≡C-A-; and A, M, -C$_t$H$_{2t}$-, D, R$_1$, R$_2$, R$_4$, s, T, and ~ are as defined above, with the proviso that V is D when E is -CH$_2$-CHR$_4$-.

The various phenyl-substituted PGF$_\alpha$-type and PGF$_\beta$-type compounds encompassed by Formulas XV to XVIII are prepared by carbonyl reduction of the corresponding PGE-type compounds. For example, carbonyl reduction of 17-phenyl-18,19,20-trinor-PGE$_1$ gives a mixture of 17-phenyl-18,19,20-trinor-PGF$_{1\alpha}$ and -PGF$_{1\beta}$.

These ring carbonyl reductions are carried out by methods known in the art for ring carbonyl reductions of known prostanoic acid derivatives. See, for example, Bergstrom et al., Arkiv Kemi 19, 563 (1963), Acta Chem. Scand. 16, 969 (1962), and British Specification No. 1,097,533. Any reducing agent is used which does not react with carbon-carbon double bonds or ester groups. Preferred reagents are lithium (tritertbutoxy) aluminum hydride, the metal borohydrides, e.g., sodium, potassium and zinc borohydrides and metal trialkoxy borohydrides, e.g., sodium trimethoxyborohydride. The mixtures of alpha and beta hydroxy reduction products are separated into the individual alpha and beta isomers by methods known in the art for the separation of analogous pairs of known isomeric prostanoic acid derivatives. See for example, Bergstrom et al., cited above, Granstrom et al., J. Biol. Chem. 240, 457 (1965), and Green et al., J. Lipid Research 5, 117

CHART A

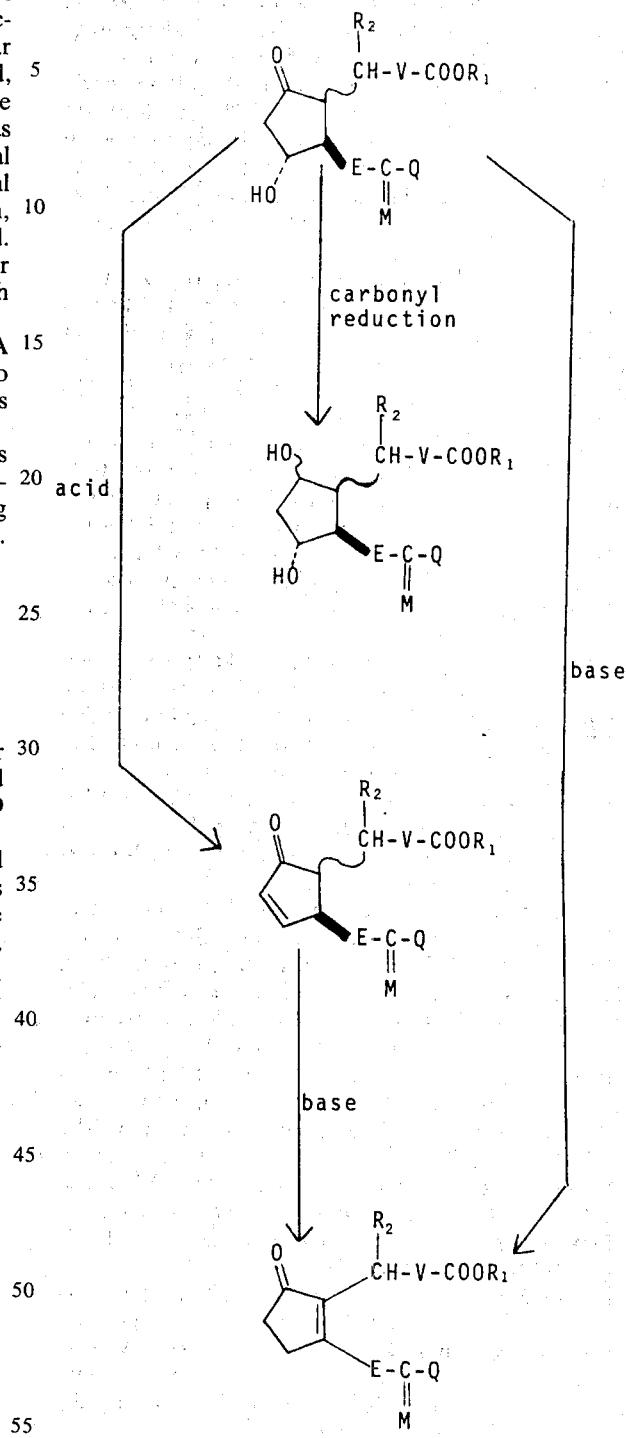

(1964). Especially preferred as separation methods are partition chromatographic procedures, both normal and reversed phase, preparative thin layer chromatography, and countercurrent distribution procedures.

The various phenyl-substituted PGA-type compounds encompassed by Formulas XIX to XXII are prepared by acidic dehydration of the corresponding PGE-type compounds encompassed by Formulas XI to XIV. For example, acidic dehydration of 17-phenyl-18, 19, 20-trinor-PGE$_1$ gives 17-phenyl-18,19,20-trinor-PGA$_1$.

These acidic dehydrations are carried out by methods known in the art for acidic dehydrations of known prostanoic acid derivatives. See, for example, Pike et al., Proc. Nobel Symposium II, Stockholm (1966); Interscience Publishers, New York, pp. 162–163 (1967), British Specification No. 1,097,533. Alkanoic acids of 2 to 6 carbon atoms, inclusive, especially acetic acid, are preferred acids for this acidic dehydration. Dilute aqueous solutions of mineral acids, e.g., hydrochloric acid, especially in the presence of a solubilizing diluent, e.g., tetrahydrofuran, are also useful as reagents for this acidic dehydration, although these reagents may also cause partial hydrolysis of an ester reactant.

The various phenyl-substituted PGB-type compounds encompassed by Formulas XXIII to <XVI are prepared by basic dehydration of the corresponding PGE type compounds encompassed by Formulas XI to XIV, or by contacting the corresponding PGA type compounds encompassed by Formulas XIX to XXII with base. For example, both 17-phenyl-18,19,20trinor-PGE$_1$ and -PGA$_1$ give 17-phenyl-18,19,20-trinor-PGB$_1$ on treatment with base.

These basic dehydrations and double bond migrations are carried out by methods known in the art for similar reactions of known prostanoic acid derivatives. See for example, Bergstrom et al., J. Biol. Chem. 238, 3555 (1963). The base is any whose aqueous solution has pH greater than 10. Preferred bases are the alkali metal hydroxides. A mixture of water and sufficient of a water-miscible alkanol to give a homogeneous reaction mixture is suitable as a reaction medium. The PGE-type or PGA-type compound is maintained in such a reaction medium until no further PGB-type compound is formed, as shown by the characteristic ultraviolet light absorption near 278 m$\mu$ for the PGB-type compound Reference to Chart B will make clear the formation of the phenyl-substituted 13,14-dihydro-PG$_1$-type compounds of Formulas XIV, XVIII, XXII, and XXVI by reduction of the corresponding PG$_1$, PG$_2$, or 5,6-dehydro-PG$_2$ type compounds. Therein, D, M, Q, R$_1$, R$_2$, R$_4$, V, and ~ are as defined above.

The various phenyl-substituted dihydro-PG$_1$-type compounds are prepared by carbon-carbon double bond reduction of the corresponding PGE, PGF$_\alpha$, PGF$_\beta$, PGA, and PGB type compound containing a trans double bond in the hydroxy-containing side chain. A cis or trans double bond or triple bond can also be present in the carboxy-terminated side chain of the unsaturated reactant, and will be reduced at the same time to -CH$_2$CH$_2$-. For example, 13-14-dihydro-17-phenyl-18,19,20-trinor-PGE$_1$ is produced by reduction of 17-phenyl-18,19,20-trinor-PGE$_1$, 17-phenyl-18,19,20-trinor-PGE$_2$, or 5,6-dehydro-17-phenyl-18, 19,20-trinor-PGE$_2$.

These reductions are carried out by reacting the unsaturated PGE, PGF$_\alpha$, PGF$_\beta$, PGA, or PGB type compound with

CHART B

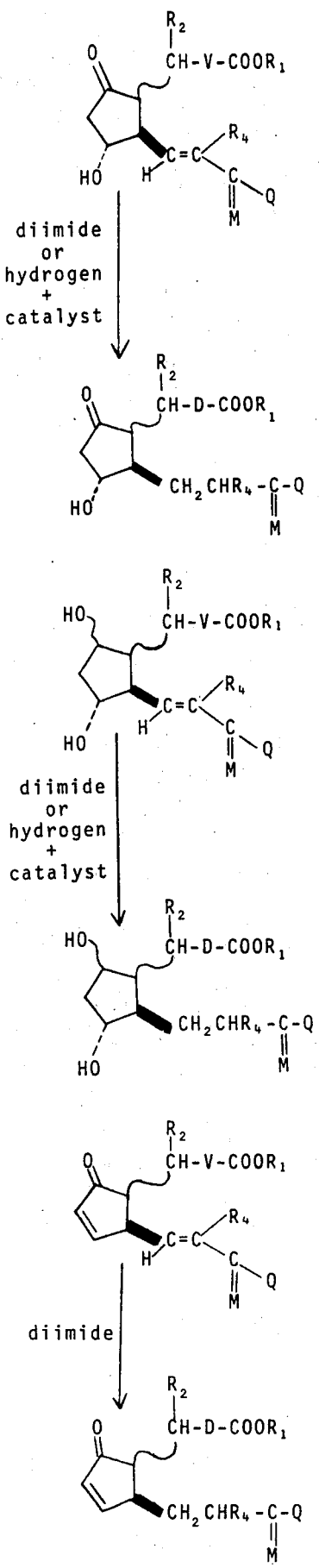

CHART B (Continued)

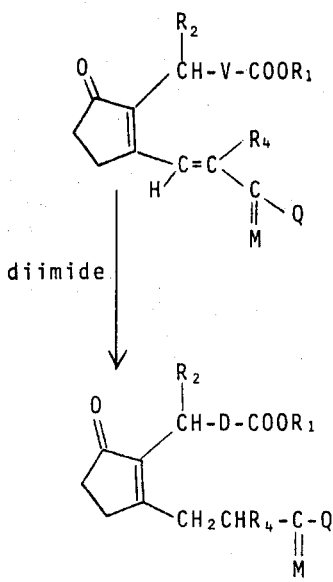

diimide, following the general procedure described by van Tamelen et al., J. Am. Chem. Soc. 83, 3726 (1961). See also Fieser et al., "Topics in Organic Chemistry," Reinhold Publishing Corp., New York, pp. 432–434 (1963) and references cited therein. The unsaturated acid or ester reactant is mixed with a salt of azodiformic acid, preferably an alkali metal salt such as the disodium or dipotassium salt, in the presence of an inert diluent, preferably a lower alkanol such as methanol or ethanol, and preferably in the absence of substantial amounts of water. At least one molecular equivalent of the azodiformic acid salt is used for each multiple bond equivalent of the unsaturated reactant. The resulting suspension is then stirred, preferably with exclusion of oxygen, and the mixture is made acid, advantageously with a carboxylic acid such as acetic acid. When a reactant wherein $R_1$ is a hydrogen is used, the carboxylic acid reactant also serves to acidify an equivalent amount of the azodiformic acid salt. A reaction temperature in the range about 10° to about 40° C. is usually suitable. Within that temperature range, the reaction is usually complete within less than 24 hours. The desired dihydro product is then isolated by conventional methods, for example, evaporation of the diluent, followed by separation from inorganic materials by solvent extraction.

In the case of the phenyl-substituted unsaturated PGE, PGF$\alpha$, and PGF$\beta$ type reactants, the reductions to the corresponding phenyl-substituted dihydro-PGE$_1$, dihydro-PGF$_{1\alpha}$, and dihydro-PGF$_{1\beta}$ compounds are also carried out by catalytic hydrogenation. For that purpose, palladium catalysts, especially on a carbon carrier, are preferred. It is also preferred that the hydrogenation be carried out in the presence of an inert liquid diluent, for example, methanol, ethanol, dioxane, ethyl acetate, and the like. Hydrogenation pressures ranging from about atmospheric to about 50 p.s.i., and hydrogenation temperatures ranging from about 10° to about 100° C. are preferred. The resulting dihydro product is isolated from the hydrogenation reaction mixture by conventional methods, for example, removal of the catalyst by filtration or centrifugation, followed by evaporation of the solvent.

The phenyl-substituted compounds of the PGE$_2$, PGF$_2$, PGA$_2$ and PGB$_2$ type wherein the carbon-carbon double bond in the carboxy-terminated side chain is in cis configuration are prepared by reduction of the corresponding 5,6-dehydro PG$_2$ compounds, i.e., those with a carbon-carbon triple bond in place of said carbon-carbon double bond. For that purpose, there are used any of the known reducing agents which reduce an acetylenic linkage to a cis-ethylenic linkage. Especially preferred for that purpose are diimide or hydrogen and a catalyst, for example, palladium (5%) on barium sulfate, especially in the presence of pyridine. See Fieser et al., "Reagents for Organic Synthesis," pp. 566-567, John Wiley & Sons, Inc., New York, N.Y. (1967). These phenyl-substituted cis compounds of the PG$_2$ type are also prepared as described hereinafter.

Chart C shows the series of reactions by which the phenyl-substituted PGE-type compounds of Formulas XI to XIII except wherein $R_1$ is hydrogen, and the phenyl-substituted PGA-type compounds of Formulas XIX to XXI except wherein $R_1$ is hydrogen are prepared. Therein Q, M, $R_2$, $R_3$, $R_4$, and V are as defined above, Q' is

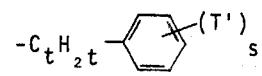

wherein T' is the same as T above except that $R_9$ is not hydrogen;

CHART C

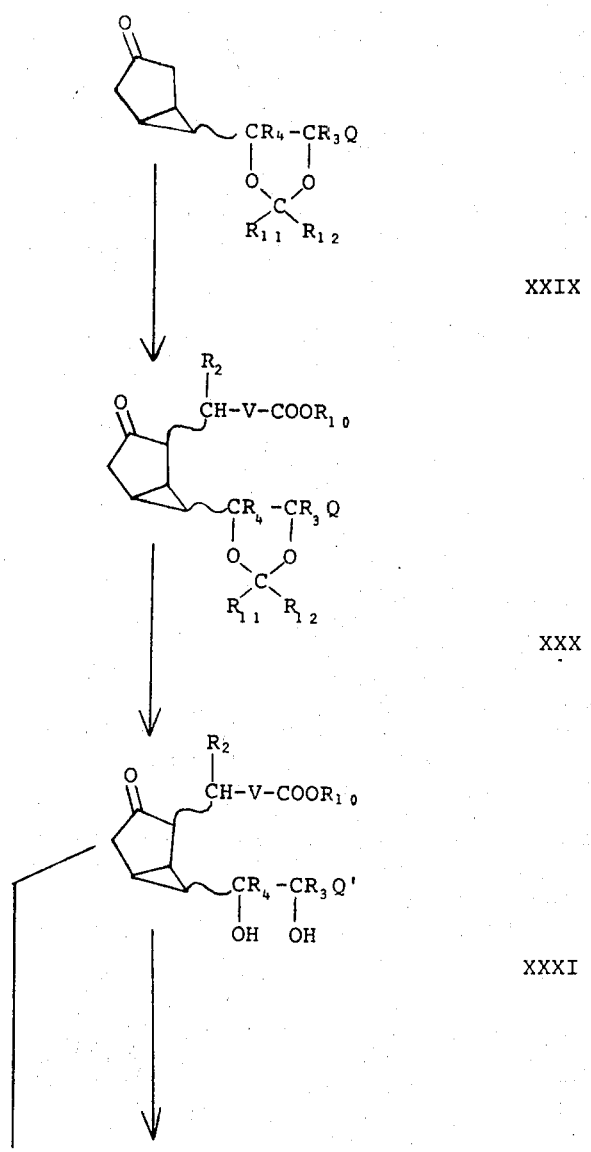

CHART C (Continued)

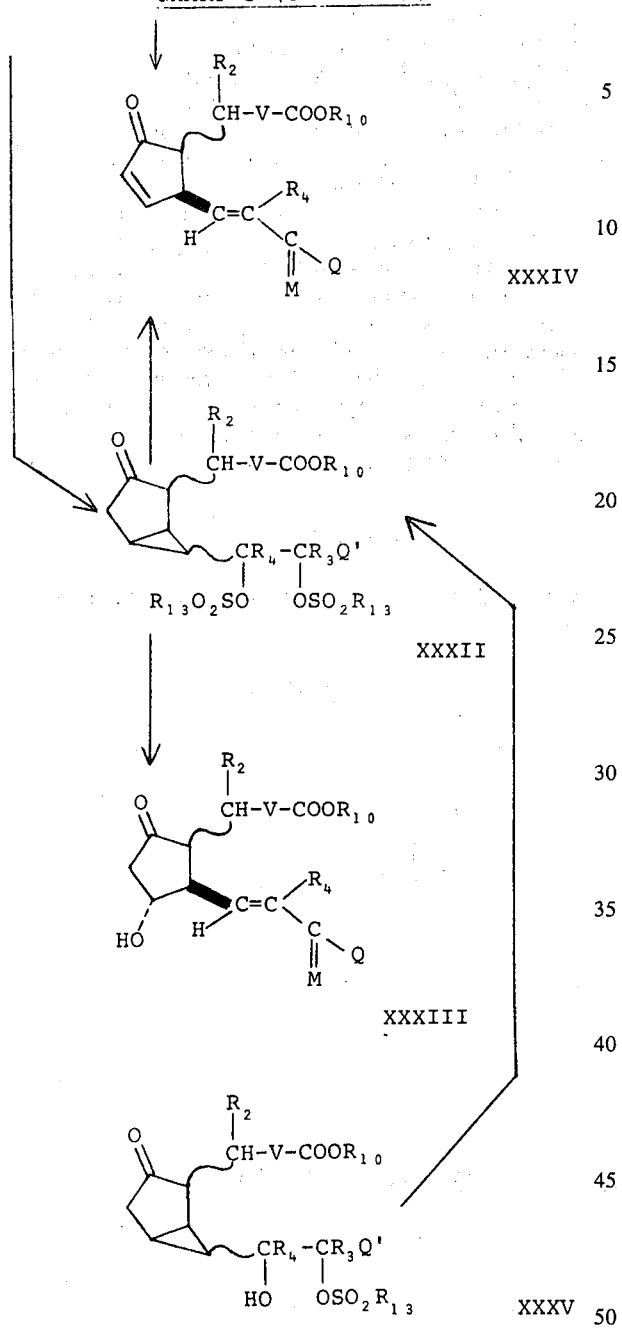

$R_{10}$ is the same as the above definition of $R_1$ except that $R_{10}$ does not include hydrogen, $R_{11}$ and $R_{12}$ are alkyl of one to 4 carbon atoms, inclusive, $R_{13}$ is alkyl of one to 5 carbon atoms, inclusive, and ~ indicates attachment of $-CHR_2-V-COOR_{10}$ to the cyclopentane ring in alpha or beta configuration, and attachment of the moiety to the cyclopropane ring in exo or endo configuration.

Chart D shows the series of reactions by which the phenyl-substituted PGE$_1$-type compounds of Formula XI, the phenyl-substituted 5,6-dehydro-PGE$_2$ type compounds of Formula XIII, the phenyl-substituted PGA$_1$ type compounds of Formula XIX, and the phenyl-substituted 5,6-dehydro-PGA$_2$ type compounds of Formula XXI are optionally prepared. Therein M, Q, Q', $R_2$, $R_3$, $R_4$, $R_{10}$, and $R_{13}$ are as defined above, Z is D or $-C \equiv C-A-$, and ~ indicates attachment of $-CHR_2-Z-COOR_{10}$ to the cyclopentane ring in alpha or beta configuration, and attachment of the moiety to the cyclopropane ring in exo or endo configuration.

It should be observed regarding the series of reactions shown in Charts C and D, that the reactions starting with glycol XXXI in Chart C are similar to the reactions starting with glycol XXXVII in Chart D. The only differences here are the definitions of the divalent moieties V (Chart C) and Z (Chart D). V includes saturated, cis and trans ethylenic, and acetylenic divalent moieties. Z is limited to the saturated and acetylenic divalent moieties encompassed by V. In other words, final phenyl-substituted PGE type compounds of Formula XXXIII (Chart C) encompass compounds of Formulas XI to XIII. Final phenyl-substituted PGA type compounds of Formula XXXIV (Chart C) encompass compounds of Formulas XIX to XXI. On the other hand, final phenyl-substituted PGE type

CHART D

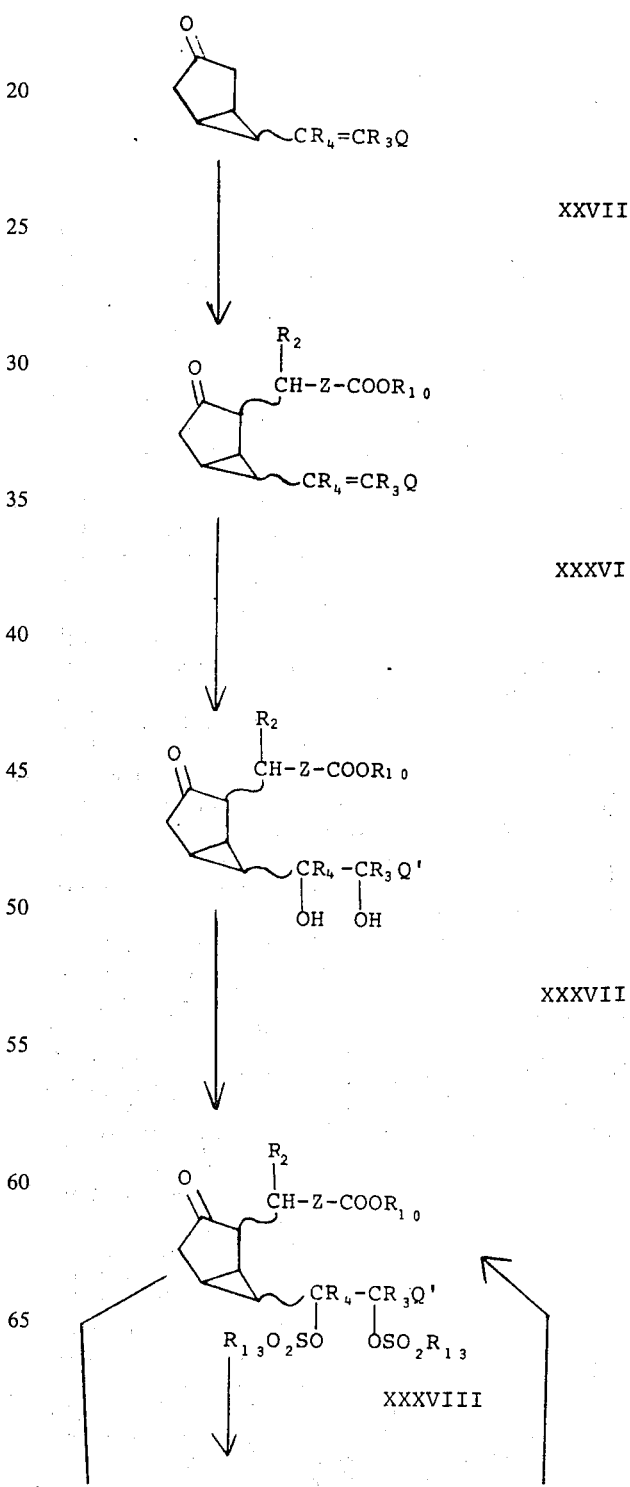

CHART D (Continued)

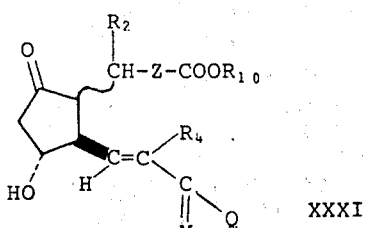

XXXIX

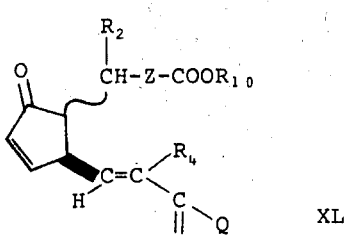

XL

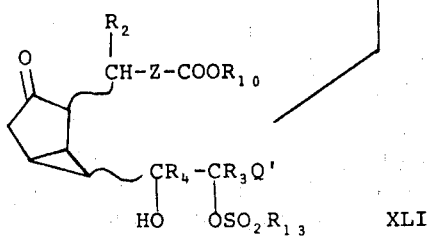

XLI compounds of Formula XXXIX (Chart D) encompass only compounds of Formulas XI and XIII; and final phenyl-substituted PGA type compounds of Formula XL (Chart D) encompass only compounds of Formulas XIX and XXI.

As will subsequently appear, an acetylenic intermediate of Formulas XXX, XXXI, or XXXVII is transformed by stepwise reduction to the corresponding cis or trans ethylenic intermediates of Formulas XXX or XXXI; and an acetylenic intermediate of Formulas XXX, XXXI, or XXXVII, or a cis or trans ethylenic intermediate of Formulas XXX or XXXI, is transformed by reduction to the corresponding saturated intermediate of Formulas XXX, XXXI, or XXXVII.

Chart E shows the series of reactions by which the Formula XXIX bicyclo-ketone cyclic ketal reactant of Chart C is obtained, and also the Formula XXVII bicyclo-ketone olefin reactant of Chart D. Therein Q, $R_3$, $R_4$, $R_{11}$, $R_{12}$, and ~ are as defined above, $\phi$ is phenyl, and J is a blocking group, such as tetrahydropyranyl.

Bicyclo-ketone olefin XXVII exists in four isomeric forms, exo and endo with respect to the attachment of the -CR$_4$=CR$_3$Q moiety, and cis and trans with respect to the double bond in that same moiety. Each of those isomers separately or various mixtures thereof are used as reactants according to this invention to produce substantially the same final phenyl-substituted PGE or PGA type product mixture.

The process for preparing either the exo or endo configuration of bicyclo-ketone olefin XXVII is known to the art. As to the exo compound, see Belgian Pat. No. 702,477; reprinted in Farmdoc Complete Specifications, Book 714, No. 30,905, page 313, March 12, 1968. As to the endo compound, see West Germany Offenlegungsschrift No. 1,937,912; reprinted in Farmdoc Complete Specifications, Book No. 14, No. 6869 R, Week R5, March 18, 1970.

In said Belgian patent No. 702,477, a reaction sequence capable of forming exo ketone XXVII is as follows: The hydroxy of 3-cyclopentenol is protected with a blocking group J, for example, with a tetrahydropyranyl group. Then a diazoacetic acid ester is added to the double bond to give an exoendo mixture of a bicyclo[3.1.0] hexane substituted at 3 with the protected hydroxy and at 6 with an esterified carboxyl. The exo-endo mixture is treated with a base to isomerize the endo isomer in the mixture to more of the exo isomer. Next, the carboxylate ester group at 6 is transformed to an aldehyde group or ketone group, -CHO or

wherein $R_4$ is as defined above. Then, said aldehyde group or said keto group is transformed by the Wittig reaction, in this case to a moiety of the formula -CR$_4$=CR$_3$Q which is in exo configuration relative to

CHART E

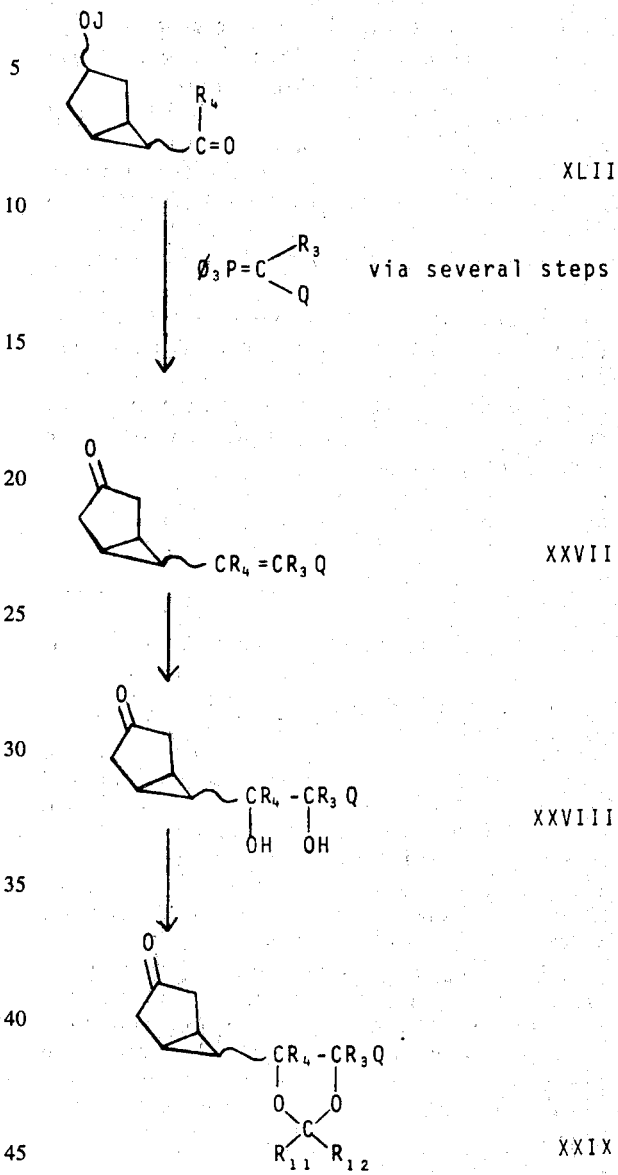

XLII via several steps

XXVII

XXVIII

XXIX the bicyclo ring structure. Next, the blocking group J is removed to regenerate the 3-hydroxy which is then oxidized, for example, by the Jones reagent, i.e. chromic acid (see J. Chem. Soc. 39 (1946)), to give said exo ketone XXVII.

The blocking group, J, is any group which replaces hydrogen of the hydroxyl groups, which is not attacked by nor is reactive to the reagents used in the respective transformations to the extent that the hydroxyl group is, and which is subsequently replaceable by hydrogen at a later stage in the preparation of the prostaglandin-like products.

Several blocking groups are known in the art, e.g. tetrahydropyranyl, acetyl, and p-phenylbenzoyl (see Corey et al., J. Am. Chem. Soc. 93, 1491 (1971)).

Those which have been found useful include (a) tetrahydropyranyl; (b) tetrahydrofuranyl; or (c) a group of the formula

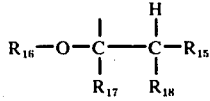

wherein $R_{16}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{17}$ and $R_{18}$ are the same or different, being hydrogen, alkyl of one to 4 carbon atoms, inclusive, phenyl or phenyl substituted with one, 2, or 3 alkyl of one to 4 carbon atoms, inclusive, or, when $R_{17}$ and $R_{18}$ are taken together, $-(CH_2)_h$- or $-(CH_2)_i-O-(CH_2)_j$- wherein h is 3, 4, or 5, i is one, 2, 3, and j is one, 2, or 3 with the proviso that i plus j is 2, 3, or 4, and wherein $R_{15}$ is hydrogen or phenyl.

When the blocking group is tetrahydropyranyl or tetrahydrofuranyl, the appropriate reagent, e.g. 2,3-dihydropyran or 2,3-dihydrofuran, is used in an inert solvent such as dichloromethane, in the presence of an acid condensing agent such as p-toluenesulfonic acid or pyridine hydrochloride. The reagent is used in slight excess, preferably 1.0 to 1.2 times theory. The reaction is carried out at about 20°–50° C.

When the blocking group is of the formula

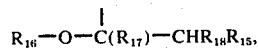

as defined above, the appropriate reagent is a vinyl ether, e.g. isobutyl vinyl ether or any vinyl ether of the formula $R_{16}-O-C(R_{17})=CR_{18}R_{15}$ wherein $R_{16}$, $R_{17}$, $R_{18}$, and $R_{15}$ are as defined above; or an unsaturated cyclic or heterocyclic compound, e.g. 1-cyclohex-1yl methyl ether

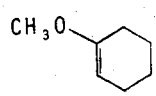

or 5,6-dihydro-4-methoxy-2H-pyran

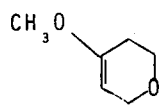

See C. B. Reese et al., J. Am. Chem. Soc. 89, 3366 (1967). The reaction conditions for such vinyl ethers and unsaturates are similar to those for dihydropyran above.

Especially preferred for the blocking group J are tetrahydropyranyl and (α-ethoxy) ethyl.

Separation of the cis-exo and trans-exo isomers of XXVII is described in said Belgian patent No. 702,477. However, as mentioned above, that separation is usually not necessary since the cis-trans mixture is useful as a reactant in the next process step.

The process decribed in said Belgian patent No. 702,477 for producing the exo form of bicyclo-ketone XXVII uses as an intermediate, the exo form of a bicyclo[3.1.0]hexane substituted at 3 with a protected hydroxy, e.g., tetrahydropyranyloxy, and at 6 with an esterified carboxyl. When the corresponding endo compound is substituted for that exo intermediate, the process in said Offenlegungsschrift No. 1,937,912 leads to the endo form of bicyclo-ketone XXVII. That endo compound to be used has the formula:

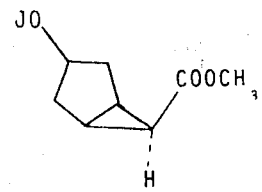

XLIII

Compound XLIII is prepared by reacting endo-bicyclo[3.1.0]hex-2-ene-6-carboxylic acid methyl ester with diborane in a mixture of tetrahydrofuran and diethyl ether, a reaction generally known in the art, to given endo bicyclo[3.1.0]hexan-3-ol-6-carboxylic acid methyl ester which is then reacted with the agent supplying the blocking group J, e.g., dihydropyran, in the presence of a catalytic amount of POCl₃ to give the desired compound. This is then used as described in said Offenlegungsschrift No. 1,937,912 to produce the endo form of bicyclo-ketone XXVII.

As with exo XXVII, this process produces a mixture of endo-cis and endo-trans compounds. These are separated as described for the separation of exo-cis and exo-trans XXVII, but this separation is usually not necessary since, as mentioned above, the cis-trans mixture is useful as a reactant in the next process step.

In the processes of said Belgian patent and said Offenlegungsschrift, certain organic halides, e.g., chlorides and bromides, are necessary to prepare the Wittig reagents used to generate the generic moiety $-CR_4=CR_3Q$ of bicyclo-ketone XXVII. The Wittig reagents are prepared by reacting these organic chlorides or bromides with triphenyl phosphine in known manner. These organic chlorides and bromides

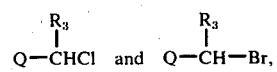

are known in the art or can be prepared by methods known in the art.

To illustrate the availability of these organic chlorides and bromides, consider the above-described phenyl-substituted PGE type compounds of Formulas XI to XIV, wherein $C_tH_{2t}$ represents a valence bond or alkylene of one to 10 carbon atoms, inclusive, substituted with zero, one, or 2 fluoro, with one to 7 carbon atoms, inclusive, between

and the phenyl ring; wherein T is alkyl of one to 4 carbon atoms, inclusive, fluoro, chloro, trifluoromethyl, or OR₉, wherein R₉ is hydrogen, alkyl of one to 4 carbon atoms, inclusive, and s is zero, one, 2, or 3, with the proviso that not more than two T's are other than alkyl; and wherein R₃ is hydrogen or alkyl of one to 4 carbon atoms, inclusive. The halides necessary to prepare those compounds, if not readily available, are advantageously prepared by reacting the corresponding primary alcohol,

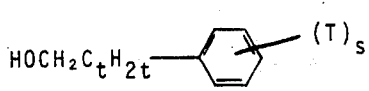

or secondary alcohol

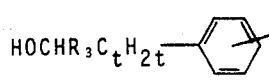

with PCl₃, PBr₃, HBr, or any of the other halogenating agents known in the art to be useful for this purpose.

In the case of R₃ being H, some of the readily available halides are shown in Table 1 wherein s, T, and t of the formula for the intermediate halides are as defined above, and Hal is chloro, bromo or iodo. Thus, compound No. 1 of Table 1 is represented by the formula wherein s and t are zero, and Hal is chloro, i.e.,

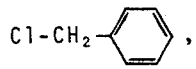

namely α-chlorotoluene or benzyl chloride; compound No. 8 of Table 1 is represented by the formula wherein s is zero, t is 2, and Hal is bromo, i.e.

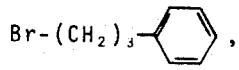

namely 1-bromo-3-phenylpropane or 3-bromopropylbenzene; and compound No. 63 of Table 1 is represented by the formula wherein s is 3, t is 2, T is methyl in the 2-, 4- and 5- positions with respect to the $C_tH_{2t}$ substitution, and Hal is bromo, i.e.

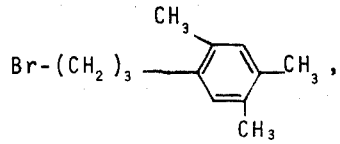

namely 1-(3-bromopropyl)-2,4,5-trimethylbenzene.

TABLE 1

Intermediate Halides represented by the formula

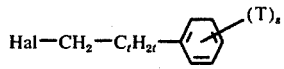

| No. | s | T | t | Hal |
|---|---|---|---|---|
| 1 | 0 | 10 — | 0 | Cl |
| 2 | 0 | — | 0 | Br |
| 3 | 0 | — | 0 | I |
| 4 | 0 | — | 1 | Cl |
| 5 | 0 | — | 1 | Br |
| 6 | 0 | — | 1 | I |
| 7 | 0 | — | 2 | Cl |
| 8 | 0 | — | 2 | Br |
| 9 | 0 | — | 2 | I |
| 10 | 0 | — | 3 | Cl |
| 11 | 0 | — | 3* | Cl |
| 12 | 0 | — | 3 | Br |

Note: * is branched  —CH—
                                          |
                                          Et

TABLE 1-continued

Intermediate Halides represented by the formula

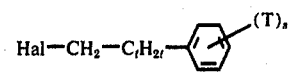

| No. | s | T | t | Hal |
|---|---|---|---|---|
| 13 | 0 | — | 4 | Cl |
| 14 | 1 | 2-CH₃ | 0 | Cl |
| 15 | 1 | 2-C₂H₅ | 0 | Cl |
| 16 | 1 | 4-C₂H₅ | 0 | Cl |
| 17 | 1 | 2-CF₃ | 0 | Cl |
| 18 | 1 | 4-OCH₃ | 0 | Cl |
| 19 | 1 | 3-CH₃ | 0 | Br |
| 20 | 1 | 4-CH₃ | 0 | Br |
| 21 | 1 | 4-C₅H₁₁ | 0 | Br |
| 22 | 1 | 4-Cl | 0 | Br |
| 23 | 1 | 2-CF₃ | 0 | Br |
| 24 | 1 | 3-CF₃ | 0 | Br |
| 25 | 1 | 4-CH₃ | 0 | I |
| 26 | 1 | 4-F | 1 | Cl |
| 27 | 1 | 3-Cl | 1 | Br |
| 28 | 1 | 4-Cl | 1 | Br |
| 29 | 1 | 4-F | 1 | Br |
| 30 | 1 | 2-Cl | 2 | Br |
| 31 | 1 | 3-Cl | 2 | Br |
| 32 | 1 | 4-Cl | 2 | Br |
| 33 | 1 | 4-F | 3* | Br |
| 34 | 1 | 2-Cl | 4 | Br |
| 35 | 2 | 2-CH₃, 4-CH₃ | 0 | Cl |
| 36 | 2 | 2-CH₃, 5-CH₃ | 0 | Cl |
| 37 | 2 | 2-CH₃, 6-CH₃ | 0 | Cl |
| 38 | 2 | 3-CH₃, 4-CH₃ | 0 | Cl |
| 39 | 2 | 2-CH₃, 4-Cl | 0 | Cl |
| 40 | 2 | 2-CH₃, 5-CH₃ | 0 | Br |
| 41 | 2 | 2-CH₃, 6-CH₃ | 0 | Br |
| 42 | 2 | 3-CH₃, 5-t-butyl | 0 | Br |
| 43 | 2 | 3-CH₃, 4-Cl | 0 | Br |
| 44 | 2 | 2-CH₃, 3-Br | 0 | Br |
| 45 | 2 | 3-OCH₃, 4-OCH₃ | 0 | Cl |
| 46 | 2 | 3-OCH₃, 5-OCH₃ | 0 | Cl |
| 47 | 2 | 3-OCH₃, 5-OCH₃ | 0 | Br |
| 48 | 2 | 2-CH₃, 4-CH₃ | 1 | Cl |
| 49 | 2 | 2-CH₃, 4-CH₃ | 1 | Br |
| 50 | 2 | 3-CH₃, 4-CH₃ | 1 | Br |
| 51 | 2 | 3-OCH₃, 4-OCH₃ | 1 | Br |
| 52 | 2 | 3-OCH₃, 5-OCH₃ | 1 | Br |
| 53 | 2 | 3-OCH₃, 4-OCH₃ | 1 | I |
| 54 | 2 | 3-OCH₃, 4-OCH₃ | 2 | Br |
| 55 | 2 | 3-OCH₃, 5-OCH₃ | 2 | Br |
| 56 | 2 | 3-OCH₃, 5-OCH₃ | 4 | Br |
| 57 | 3 | 2-CH₃, 4-CH₃, 5-CH₃ | 0 | Cl |
| 58 | 3 | 2-CH₃, 4-CH₃, 6-CH₃ | 0 | Cl |
| 59 | 3 | 4-CH₃, 2-OCH₃, 5-OCH₃ | 0 | Cl |
| 60 | 3 | 2-CH₃, 3-CH₃, 6-CH₃ | 0 | Br |
| 61 | 3 | 2-CH₃, 4-CH₃, 6-CH₃ | 0 | Br |
| 62 | 3 | 2-CH₃, 3-OCH₃, 6-OCH₃ | 0 | Br |

TABLE 1-continued

Intermediate Halides represented by the formula

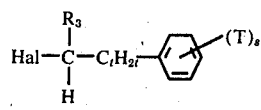

| No. | s | T | t | Hal |
|---|---|---|---|---|
| 63 | 3 | 2-CH$_3$<br>4-CH$_3$<br>5-CH$_3$ | 2 | Br |

In the case of R$_3$ being alkyl, some of the readily available halides are shown in Table II. Thus, compound No. 1 of Table II is represented by the formula wherein R$_3$ is methyl, s and t are zero, and Hal is chloro, i.e.

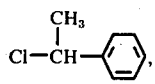

namely (1-chloroethyl)benzene; and compound No. 13 of Table II is represented by the formula wherein R$_3$ is methyl, s is 2, t is one, T is methyl, and Hal is bromo, i.e.

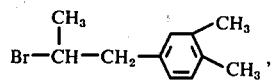

namely 4-(2-bromopropyl)-o-xylene or 1-(2-bromopropyl)-3-methyl-4-methylbenzene.

TABLE II

Intermediate Halides represented by the formula

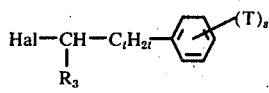

| No. | s | T | R | t | Hal |
|---|---|---|---|---|---|
| 1 | 0 | — | CH$_3$ | 0 | Cl |
| 2 | 0 | — | C$_2$H$_5$ | 0 | Cl |
| 3 | 0 | — | C$_2$H$_5$ | 0 | Br |
| 4 | 0 | — | CH$_3$ | 0 | I |
| 5 | 0 | — | CH$_3$ | 1 | Cl |
| 6 | 0 | — | n-C$_3$H$_7$ | 1 | Cl |
| 7 | 0 | — | CH$_3$ | 1 | Br |
| 8 | 0 | — | C$_2$H$_5$ | 2 | Cl |
| 9 | 1 | 4-C$_2$H$_5$ | CH$_3$ | 0 | Cl |
| 10 | 1 | 4-F | CH$_3$ | 0 | Cl |
| 11 | 1 | 4-Cl | C$_2$H$_5$ | 0 | Br |
| 12 | 1 | 4-F | C$_2$H$_5$ | 0 | Br |

| No. | s | T | R$_3$ | t | Hal |
|---|---|---|---|---|---|
| 13 | 2 | 3-CH$_3$<br>4-CH$_3$ | CH$_3$ | 1 | Br |
| 14 | 2 | 3-OCH$_3$<br>4-OCH$_3$ | CH$_3$ | 1 | Br |
| 15 | 2 | 2-OCH$_3$<br>6-OCH$_3$ | CH$_3$ | 1 | Br |

Other intermediate halides of the general formula

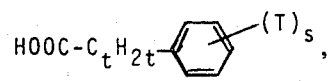

may be obtained from the primary or secondary alcohols as discussed above. These alcohols are in general prepared from corresponding carboxylic acids. Thus, the substituted benzoic acids are selectively reduced to the corresponding benzyl alcohols using any of several hydride reagents, e.g., sodium borohydride/aluminum chloride in diglyme, diborane in tetrahydrofuran, aluminum hydride in tetrahydrofuran, and the like. The secondary alcohols, wherein R$_3$ is alkyl, are prepared by transforming the -COOH of the corresponding carboxylic acid

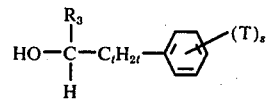

to a ketone by known procedures, e.g. by way of the acyl chloride and a dialkylcadmium. Reduction of the ketone with sodium borohydride then yields the secondary alcohol,

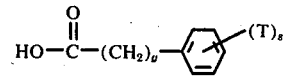

Hydroxyl groups on the aromatic ring are suitably protected during these reactions by first forming the corresponding blocking groups, e.g. tetrahydropyranyl ethers with dihydropyran; the hydroxyl groups are restored by mild acid hydrolysis as is well known in the art.

In the case of C$_t$H$_{2t}$ substituted with one or 2 fluoro atoms, there are a number of routes to the intermediate halides. The corresponding alcohols, for example β-fluorophenethyl alcohol, β-fluoro-α-methyl-phenethyl alcohol, β-fluoro-α,β-dimethyl-phenethyl alcohol and the like, are reacted with PCl$_3$, PBr or HBr to form the halide. Alternatively, the carboxylic acid having one less carbon atom in the chain than the desired intermediate halide, i.e.

$$HO-\overset{O}{\overset{\|}{C}}-(CH_2)_g-\underset{}{\bigcirc}-(T)_s$$

wherein g is t-1, is converted by a series of known methods to the 2,2-difluorohalide. Thus, the free carboxyl group is transformed first to the acid chloride with thionyl chloride and thence by way of the nitrile to the α-keto-acid. The carboxyl group is reduced to the alcohol with diborane and then converted to the α-keto halide. Finally, by reaction of the keto group with sulfur tetrafluoride, there is obtained

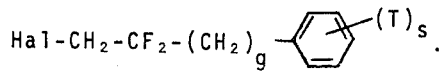

For reactions of SF₄ see U.S. Pat. No. 3,211,723 and J. Org. Chem. 27, 3164 (1962).

As mentioned above, Formula XI-to-XXVI compounds with an alpha-fluoro substituent on the carbon adjacent to the hydroxy-substituted carbon (C-15 in PGE₁) represent preferred embodiments among the novel phenyl-substituted compounds of this invention. The Formula XXVII bicyclo-ketones necessary to produce those mono-fluoro compounds are advantageously prepared by reacting either of the above-mentioned bicycloaldehydes, exo or endo, with a Wittig reagent prepared from

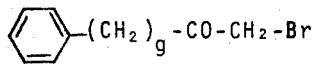

and triphenylphosphine. The aldehyde group is thereby transformed to

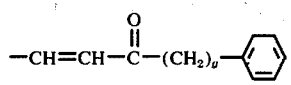

The resulting unsaturated ketone is reduced to the corresponding

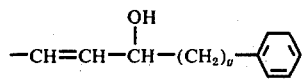

compound. Then -OH in that group is replaced with fluoro by known methods, for example, directly by reaction with 2-chloro-1,1,2-trifluorotriethylamine or indirectly for example, by transforming the hydroxy to tosyloxy or mesyloxy, and reacting the resulting compound with anhydrous potassium fluoride in diethylene glycol.

The transformation of bicyclo-ketone-olefin XXVII to glycol XXVIII is carried out by reacting olefin XXVII with a hydroxylation reagent. Hydroxylation reagents and procedures for this purpose are known in the art. See, for example, Gunstone, Advances in Organic Chemistry, Vol. 1, pp. 103–147, Interscience Publishers, New York, N.Y. (1960). Various isomeric glycols are obtained depending on such factors as whether olefin XXVII is cis or trans and endo or exo, and whether a cis or a trans hydroxylation reagent is used. Thus endo-cis olefin XXVII gives a mixture of two isomeric erythro glycols of Formula XXVIII with a cis hydroxylation agent, e.g., osmium tetroxide. Similarly, the endo-trans olefin XXVII gives a similar mixture of the same two erythro glycols with a trans hydroxylation agent, e.g., hydrogen peroxide. The endo-cis olefins and the endo-trans olefins XXVII give similar mixtures of two threo glycol isomers with trans and cis hydroxylation reagents, respectively. These various glycol mixtures are separated into individual isomers by silica gel chromatography. However, this separation is usually not necessary, since each isomeric erythro glycol and each isomeric threo glycol is useful as an intermediate according to this invention and the processes outlined in Chart C to produce final products of Formulas XXXIII and XXXIV, and then, according to Charts A and B, to produce the other final products of this invention. Thus, the various isomeric glycol mixtures encompassed by Formula XXVIII produced from the various isomeric olefins encompassed by Formula XXVII are all useful for these same purposes.

The transformation of glycol XXVIII to the cyclic ketal of Formula XXIX (Chart C) is carried out by reacting said glycol with a dialkyl ketone of the formula

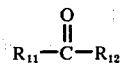

wherein $R_{11}$ and $R_{12}$ are alkyl of one to 4 carbon atoms, inclusive, in the presence of an acid catalyst, for example potassium bisulfate or 70% aqueous perchloric acid. A large excess of the ketone and the absence of water is desirable for this reaction. Examples of suitable dialkyl ketones are acetone, methyl ethyl ketone, diethyl ketone, methyl propyl ketone, and the like. Acetone is preferred as a reactant in this process.

Referring again to Chart C, cyclic ketal XXIX is transformed to cyclic ketal XXX by alkylating with an alkylation agent of the formula

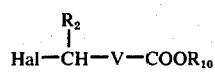

wherein $R_2$, $R_{10}$, and V are as defined above, and Hal is chloro, bromo, or iodo. Similarly, referring to Chart D, olefin XXVII is transformed to olefin XXXVI by alkylating with an alkylation agent of the formula

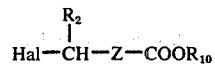

wherein $R_2$, $R_{10}$, Z, and Hal are as defined above.

Any of the alkylation procedures known in the art to be useful for alkylating cyclic ketones with alkyl halides and haloalkanoic esters are used for the transformations of XXIX to XXX and XXVII to XXXVI. See, for example, the above-mentioned Belgian patent No. 702,477 for procedures useful here are used there to carry out similar alkylations.

For these alkylations, it is preferred that Hal be bromo or iodo. Any of the usual alkylation bases, e.g., alkali metal alkoxides, alkali metal amides, and alkali metal hydrides, are useful for this alkylation. Alkali metal alkoxides are preferred, especially tert-alkoxides. Sodium and potassium are preferred alkali metals. Especially preferred is potassium tert-butoxide. Preferred diluents for this alkylation are tetrahydrofuran and 1,2-dimethoxyethane. Otherwise, procedures for producing and isolating the desired Formula XXX and XXXVI compounds are within the skill of the art.

These alkylation procedures produce mixtures of alpha and beta alkylation products, i.e., a mixture of Formula XXX products wherein part has the -CHR₂-V-COOR₁₀ moiety attached in alpha configuration, and wherein part has that moiety attached in beta configuration, or a mixture of Formula XXXVI products with the -CHR₂-Z-COOR₁₀ moiety in both alpha and beta configurations. When about one equivalent of base per equivalent of Formula XXVII or XXIX ketone is used, the alpha configuration usually predominates. Use of an excess of base and longer reaction times usually result in production of larger amounts of beta products. These alpha-beta isomer mixtures are separated at this stage or at any subsequent stage in the multi-step processes shown in Charts C and D. Silica gel chromatography is preferred for this separation.

The necessary alkylating agents for the above-described alkylations, i.e., compounds of the formulas $$Hal-\overset{R_2}{\underset{|}{C}H}-V-COOR_{10}$$

and $$Hal-\overset{R_2}{\underset{|}{C}H}-Z-COOR_{10},$$

are prepared by methods known in the art.

These are four groups of compounds encompassed by these two genera of alkylating agents. Alkylating agents of the formula $$Hal-\overset{R_2}{\underset{|}{C}H}-Z-COOR_{10}$$

include compounds of the following formulas:

$$Hal-\overset{R_2}{\underset{|}{C}H}-D-COOR_{10} \qquad \text{XLIV}$$

$$Hal-\overset{R_2}{\underset{|}{C}H}-C\equiv C-A-COOR_{10} \qquad \text{XLV}$$

Alkylating agents of the formula $$Hal-\overset{R_2}{\underset{|}{C}H}-V-COOR_{10}$$

include the above-listed compounds of Formulas XLIV and XLV, and also compounds of the following formulas:

$$\underset{Hal-\overset{|}{C}H}{\overset{R_2}{\underset{|}{}}}\diagdown_{\!\!\!\!\!/}\overset{H}{\underset{A-COOR_{10}}{C=C}}\diagup^{H} \qquad \text{XLVI}$$

$$\underset{Hal-\overset{|}{C}H}{\overset{R_2}{\underset{|}{}}}\diagdown_{\!\!\!\!\!/}\overset{H}{\underset{H}{C=C}}\diagup^{A-COOR_{10}} \qquad \text{XLVII}$$

These alkylating agents of Formulas XLIV to XLVII are accessible to those of ordinary skill in the art. As an example, there are available methyl ω-iodoheptanoate and methyl ω-iodohexanoate. Those of Formula XLIV are prepared by reacting a hydroxy ester of the formula $$HO-\overset{R_2}{\underset{|}{C}H}-D-COOR_{10}$$

with a reagent such as $PBr_3$, $PCl_3$, HBr or HI. Alternatively a compound of the formula $$Hal-\overset{R_2}{\underset{|}{C}H}-D-CH_2OH$$

is oxidized to the carboxylic acid with the Jones oxidizing reagent, and the acid esterified to the $R_{10}$ ester. Similarly, those of Formula XLV are prepared from a compound of the formula $$Hal-\overset{R_2}{\underset{|}{C}H}-C\equiv C-A-CH_2\,OH$$

by oxidation to the acid, and esterification to the $R_{10}$ ester.

The cis and trans ethylenic alkylating agents of Formulas XLVI and XLVII respectively are prepared by cis or trans reduction of an acetylenic intermediate in which both ends of the acetylenic bond are substituted, e.g.

$$Hal-\overset{R_2}{\underset{|}{C}H}-C\equiv C-A-CH_2OH,$$

followed by conversion to the acid and thence to the ester.

For these cis reductions of the acetylenic bonds, it is advantageous to use hydrogen plus a catalyst which catalyzes hydrogenation of -C≡C- only to cis-CH=CH-. Such catalysts and procedures are well known to the art. See, for example, Fieser et al., "Reagents for Organic Syntheses", pp. 566–567; John Wiley & Sons, Inc., New York, N.Y. (1967). Palladium (5%) on barium sulfate, especially in the presence of pyridine as a diluent, is a suitable catalyst for this purpose. Alternative reagents useful to transform these acetylenic compounds to cis-ethylenic compounds are bis-3-methyl-2-butylborane (disiamylborane) and diisobutylaluminum hydride.

For trans reductions of the acetylenic bond, it is advantageous to use sodium or lithium in liquid ammonia or a liquid alkylamide, e.g., ethylamine. When the moiety $HO-CH_2-C\equiv C-$ is present in the acetylenic compound being reduced, the use of lithium aluminum hydride gives trans reduction of the triple bond. Procedures for these trans reductions are known in the art. See, for example, Fieser et al., above cited, pp. 577, 592–594, and 603, and J. Am. Chem. Soc. 85, 622 (1963).

Referring again to Chart C, after alkylation as discussed above, cyclic ketal XXX is transformed to glycol XXXI by reacting the cyclic ketal with an acid with pK less than 5. Suitable acids and procedures for hydrolyzing cyclic ketals to glycols are known in the art. Suitable acids are formic acid, hydrochloric acid, and boric acid. Especially preferred as diluents for this reaction are tetrahydrofuran and β-methoxyethanol.

Referring again to Chart D, after alkylation as discussed above, olefin XXXVI is hydroxylated to glycol XXXVII. As discussed above, the divalent moiety -Z- includes the moieties -D- and -C≡C-A-, wherein A and D are as defined above. When Z is -D-, for example alkylene of 3 to 12 carbon atoms, this hydroxylation of XXXVI is carried out as described above for the hydroxylation of olefin XXVII to glycol XXVIII, i.e., with any of the known reagents and procedures described in Gunstone, above cited. When Z is -C≡C-A-, some of the reagents and procedures described by Gunstone tend to attack the acetylenic linkage as well as the ethylenic linkage of olefin XXXVI. Therefore it is preferred to use a hydroxylation reagent and procedure which attacks the ethylenic linkage preferentially. For this, it is preferred to carry out hydroxylation of these acetylenic Formula XXXVI olefins with organic peracids, e.g., performic acid, peracetic acid, perbenzoic acid, and m-chloroperbenzoic acid, as described by Gunstone, above cited, pp. 124–130.

As discussed above regarding the hydroxylation of unalkylated olefin XXVII to unalkylated glycol XXVIII various isomeric glycols are obtained by hydroxylation of the Formula XXXVI alkylated olefin. The particular Formula XXXVII glycol or glycol mixture obtained depends on such factors as whether the olefin XXXVI is cis or trans and endo or exo, and whether a cis or a trans hydroxylation takes place. however, all of the isomeric Formula XXXVI erythro and threo glycols and the various glycol mixtures each are useful as an intermediate according to this invention and the processes of Chart D to produce final products of Formulas XXXIX and XL, and then according to Charts A and B, to produce the other final products of this invention. Therefore, it is usually not necessary to separate individual glycol XXXVI isomers before proceeding further in the synthesis, although that separation is accomplished by silica gel chromatography.

Referring again to Charts C and D, bis-alkanesulfonic acid esters XXXII and XXXVII are prepared by reacting glycols XXXI and XXXVII, respectively, with an alkanesulfonyl chloride or bromide, or with an alkanesulfonic acid anhydride, the alkyl in each containing one to 5 carbon atoms, inclusive. Alkanesulfonyl chlorides are preferred for this reaction. The reaction is carried out in the presence of a base to neutralize the byproduct acid. Especially suitable bases are tertiary amines, e.g., dimethylaniline or pyridine. It is usually sufficient merely to mix the two reactants and the base, and maintain the mixture in the range 0° to 25° C. for several hours. The Formula XXXII and XXXVIII bis-sulfonic acid esters are then isolated by procedures known to the art.

Referring now to Chart C, bis-sulfonic acid esters XXXII are transformed either to phenyl-substituted PGE type compounds XXXIII, or to phenyl-substituted PGA type compounds XXXIV. Referring to Chart D, bis-sulfonic acid esters XXXVIII are transformed either to phenyl-substituted PGE type compounds XXXIX, or to phenyl-substituted PGA type compounds XL.

The transformations of XXXII and XXXVIII to the PGE type compounds XXXIII and XXXIX, respectively, are carried out by reacting bis-esters XXXII and XXXVIII with water in the range about 0° to about 60° C. In making the phenyl-substituted PGE$_1$ compounds, 25° C. is a suitable reaction temperature, the reaction then proceeding to completion in about 5 to 20 hours. It is advantageous to have a homogenous reaction mixture. This is accomplished by adding sufficient of a water-soluble organic diluent which does not enter into the reaction. Acetone is a suitable diluent. The desired product is isolated by evaporation of excess water and diluent if one is used. The residue contains a mixture of Formula XXXIII or Formula XXXIX isomers which differ in the configuration of the side chain hydroxy, that being either alpha (S) or beta (R). These are separated from byproducts and from each other by silica gel chromatography. A usual byproduct is the mono-sulfonic acid ester of Formula XXXV (Chart C) or Formula XLI (Chart D). These mono-sulfonic acid esters are esterified to the Formula XXXII or XXXVIII bis-sulfonic acid esters, respectively, in the same manner described above for the transformation of glycol XXXI or XXXVII to bis-ester XXXII or XXXVIII and thus are recycled back to additional Formula XXXIII or XXXIX final product.

The transformations of XXXII and XXXVIII to the PGA type compounds XXXIV and XL, respectively, are carried out by heating bis-esters XXXII and XXXVIII in the range 40° to 100° C. with a combination of water, a base characterized by its water solution having a pH 8 to 12, and sufficient inert water-soluble organic diluent to form a basic and substantially homogenous reaction mixture. A reaction time of one to 10 hours is usually used. Preferred bases are the water-soluble salts of carbonic acid, especially alkali metal bicarbonates, e.g., sodium bicarbonate. A suitable diluent is acetone. The products are isolated and separated as described above for the transformation of bis-esters XXXII and XXXVIII to PGE type products XXXIII and XXXIX. The same mono-sulfonic acid esters XXXV and XLI observed as byproducts in those transformations are also observed during preparation of PGA type products XXXIV and XL.

For the transformations of bis-sulfonic acid esters XXXII and XXXVIII to final products XXXIII, XXXIV, XXXIX, and XL, it is preferred to use the bis-mesyl esters, i.e., compounds XXXII and XXXVIII wherein R$_{13}$ is methyl.

Referring again to Charts C and D, the configuration of the

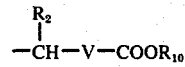

moiety in the Formula XXXII bis-esters or the configuration of the

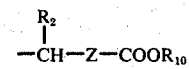

moiety in the Formula XXXVIII bis-esters does not change during these transformations of XXXII to XXXIII, XXXIV, and XXXV, and of XXXVIII to XXXIX, XL, and XLI. Therefore, when in Formula XXXII, for example, V is -(CH$_2$)$_5$-,

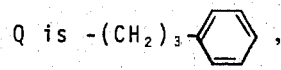

and R$_2$, R$_3$ and R$_4$ are hydrogen, R and S 18-phenyl-19,20-dinor-PGE$_1$ esters (XXXIII) are obtained when

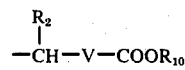

is attached initially (XXXII) in alpha configuration, and R and S 8-iso-18-phenyl-19,20-dinor-PGE$_2$ esters (XXXIII) are obtained when that moiety is attached in beta configuration. Similarly, when in Formula XXXII, V is cis-$CH=CH(CH_2)_3$- or -$C\equiv C(CH_2)_3$-, Q is

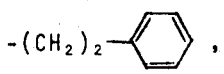

and $R_2$, $R_3$, and $R_4$ are hydrogen, R and S 17-phenyl-18,19,20-trinor-$PGE_2$ esters and R and S 5,6-dehydro-17-phenyl-18,19,20-trinor-$PGE_2$ esters are obtained when

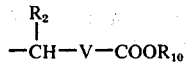

is attached initially in alpha configuration, and the corresponding 8-iso compounds are obtained when that moiety is attached in beta configuration. The same retention of

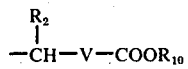

configuration occurs when Formula XXXIV and XXXV compounds are produced, and a similar retention of

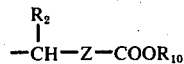

configuration occurs when Formula XXXIX, XL, and XLI compounds are produced from Formula XXXVIII bis-esters.

The Formula XXXIII and XXXIX phenyl-substituted PGE type compounds and the Formula XXXIV and XL phenyl-substituted PGA type compounds shown in Charts C and D are all $R_{10}$ carboxylic acid esters, wherein $R_{10}$ is as defined above. Moreover, when those PGE-type and PGA-type $R_{10}$ esters are used to prepare the other phenyl-substituted prostaglandinlike compounds according to Charts A and B, corresponding $R_{10}$ esters are likely to be produced, especially in the case of the phenyl-substituted PGF type compounds. For some of the uses described above, it is preferred that the novel Formula XI-to-XXVI phenyl-substituted prostaglandin-like compounds of this invention be in free acid form, or in salt form which requires the free acid as a starting material. The PGF-type esters of Formulas XV to XVIII and the PGB-type compounds of Formulas XXIII to XXVI are easily hydrolyzed or saponified to the free acids by the usual known procedures, especially when $R_1$ ($R_{10}$) is alkyl of one to 4 carbons, inclusive, preferably methyl or ethyl.

On the other hand, the PGE-type and PGA-type esters are difficult to hydrolyze or saponify without causing unwanted structural changes in the desired acids. There are two other procedures to make the free acid forms of these Formula XI-to-XIV and XIX-to-XXII compounds.

One of those procedures is applicable mainly in preparing the free acids from the corresponding alkyl esters wherein the alkyl group contains one to 8 carbon atoms, inclusive. That procedure comprises subjecting the PG-type alkyl ester to the acylase enzyme system of a microorganism species of Subphylum 2 of Phylum III, and thereafter isolating the acid. See West Germany Offenlegungsschrift No. 1,937,678; reprinted in Farmdoc Complete Specifications, Book No. 13, No. 6863 R, Week R5, March 18, 1970.

Another procedure for making the free acids of Formula XI-to-XIV PGE-type compounds and Formula XIX-to-XXII PGA-type compounds involves treatment of certain haloethyl esters of those acids with zinc metal and an alkanoic acid of 2 to 6 carbon atoms, preferably acetic acid. Those haloethyl esters are the esters wherein $R_1$ is ethyl substituted in the $\beta$-position with 3 chloro, 2 or 3 bromo, or one, 2, or 3 iodo. Of those haloethyl moieties, $\beta,\beta,\beta$-trichloroethyl is preferred. Zinc dust is preferred as the physical form of the zinc. Mixing the haloethyl ester with the zinc dust at about 25° C. for several hours usually causes substantially complete replacement of the haloethyl moiety of the Formula XI-to-XIV or XIX-to-XXII ester with hydrogen. The free acid is then isolated from the reaction mixture by procedures known to the art. This procedure is also applicable to the production of Formula XV-to-XVIII PGF-type free acids and Formula XXIII-to-XXVI PGB-type free acids.

Formula XXX cyclic ketals and Formula XXXVII olefins wherein $R_{10}$ is haloethyl as above defined are necessary as intermediates for this route to the final PGE, PGF, PGA, and PGB type free acids. These Formula XXX and XXXVI haloethyl ester intermediates can be prepared by alkylation of cyclic ketal XXIX (Chart C) or olefin XXVII (Chart D), respectively, with the appropriate Formula XLIII-to-XLVII alkylating agent wherein $R_{10}$ is haloethyl as above defined.

Alternate routes to the Formula XXX and XXXVII haloethyl ester intermediates of Charts C and D respectively comprise (a) reducing the corresponding alkyl, cycloaklyl, aralkyl, phenyl, or substituted-phenyl esters within the scope of Formulas XXX and XXXVI with a carbonyl reducing agent, (b) saponifying the resulting hydroxy esters, and (c) obtaining the desired keto haloethyl esters by oxidation of the hydroxy group to keto and esterification of the carboxyl group to -COO-haloethyl. See Belgian Pat. No. 754,114, reprinted in Farmdoc Complete Specifications as No. 10044S, Week S5, Jan. 31, 1971. Haloethyl esters are prepared by reacting the appropriate acids with an haloethanol, e.g., $\beta,\beta,\beta$-trichloroethanol, in the presence of a carbodiimide, e.g., dicyclohexylcarbodiimide, and a base, e.g., pyridine, preferably in the presence of an inert liquid diluent, e.g., dichloromethane, for several hours at about 25° C. See, for example, Fieser et al., "Reagents for Organic Synthesis", page 231.

As described above, the alkylations of cyclic ketal XXIX to XXX (Chart C) and olefin XXVII to XXXVI (Chart D) usually produce mixtures of alpha and beta alkylation products with respect to the

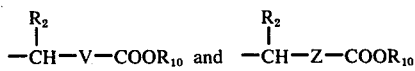

moieties. Also as described above, those two isomers lead to different final products, alpha leading to the PG type series, and beta leading to the 8-iso-PG type series. If a compound in one or the other of those two series is preferred, there are two methods for favoring production of the preferred final product.

One of these methods involves isomerization of the final product of Formulas XI to XIV. Either the alpha isomer of a Formula XI-to-XIV compound, ester or free acid, or the corresponding beta isomer is maintained in an inert liquid diluent in the range 0° to 80° C. and in the presence of a base characterized by its water solution having a pH below 10 until a substantial amount of the isomer has been isomerized to the other isomer, i.e., alpha to beta or beta to alpha. Preferred bases for this purpose are the alkali metal salts of carboxylic acids, especially alkanoic acids of 2 to 4 carbon atoms, e.g., sodium acetate. Examples of useful inert liquid diluents are alkanols of one to 4 carbon atoms, e.g., ethanol. This reaction at about 25° C. takes one to about 20 days. Apparently an equilibrium is established. The mixtures of the two isomers, alpha and beta, are separated from the reaction mixture by known procedures, and then the two isomers are separated from each other by known procedures, for example, chromatography, recrystallization, or a combination of those. The less preferred isomer is then subjected to the same isomerization to produce more of the preferred isomer. In this manner, by repeated isomerizations and separations, substantially all of the less preferred isomer of the Formula XI-to-XIV compound is transformed to more preferred isomer.

The second method for favoring production of a preferred Formula XI-to-XIV isomer involves any one of the keto intermediates of Formulas XXX, XXXI, XXXVI, or XXXVII (Charts C and D). Either the alpha form or the beta form of one of those intermediates is transformed to a mixture of both isomers by maintaining one or the other isomer, alpha or beta, in an inert liquid diluent in the presence of a base and in the range 0° to 100° C. until a substantial amount of the starting isomer has been isomerized to the other isomer. Preferred bases for this isomerization are alkali metal amides, alkali metal alkoxides, alkali metal hydrides, and triarylmethyl alkali metals. Especially preferred are alkali metal tertalkoxides of 4 to 8 carbon atoms, e.g., potassium tertbutoxide. This reaction at about 25° C. proceeds rapidly (one minute to several hours). Apparently an equilibrium mixture of both isomers is formed, starting with either isomer. The isomer mixtures in the equilibrium mixture thus obtained are isolated by known procedures, and then the two isomers are separated from each other by known procedures, for example, chromatography. The less preferred isomer is then subjected to the same isomerization to produce more of the preferred isomer. In this manner, by repeated isomerizations and separations, substantially all of the less preferred isomer of any of these intermediates is transformed to the more preferred isomer. Cyclic acetal-ketone intermediates of Formula XXX are preferred over the other intermediates for this isomerization procedure.

Certain 15-alkyl phenyl-substituted PGE, PGF, PGA and PGB type compounds of Formula XI to XXVI wherein $R_3$ is alkyl of one to 4 carbon atoms, inclusive, preferably methyl or ethyl, are preferred over the corresponding phenyl-substituted PGE, PGF, PGA and PGB type compounds in which $R_3$ is hydrogen for the above-described pharmacological purposes.

These 15-alkyl prostaglandin analogs are surprisingly and unexpectedly more useful than the corresponding 15-hydrogen compounds for the reason that they are substantially more specific with regard to potency in causing prostaglandin-like biological responses, and have a substantially longer duration of biological activity. For that reason, fewer and smaller doses of these 15-alkyl prostaglandin analogs are needed to attain the desired pharmacological results.

Although the above-mentioned 15-alkyl compounds are produced by the methods outlined above in Charts A–D, the preferred methods are set forth in Chart F as follows.

In Chart F, $R_{19}$ is alkyl of one to 4 carbon atoms, inclusive, and E, Hal, Q, $R_1$, $R_2$, and V are as heretofore

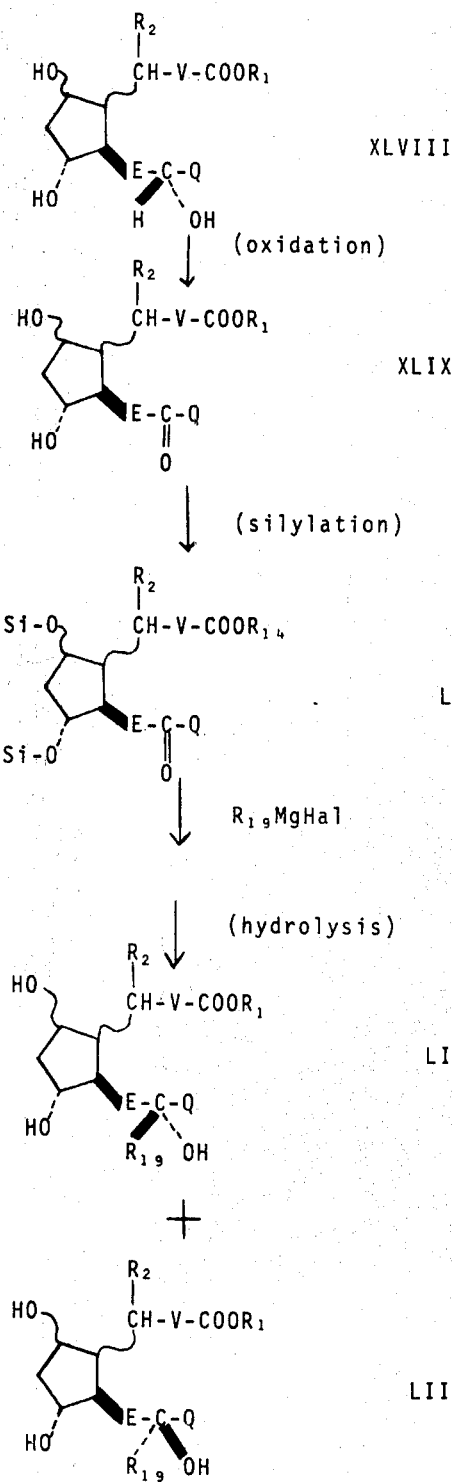

defined. Also in Chart F, G is alkyl of one to 4 carbon atoms, inclusive, aralkyl of 7 to 12 carbon atoms, inclusive, phenyl, or phenyl substituted with one or 2 fluoro, chloro, or alkyl of one to 4 carbon atoms, inclusive, and $R_{14}$ is $R_1$ as defined above or silyl of the formula -Si-$(G)_3$ wherein G is as defined above. The various G's of a -Si$(G)_3$ moiety are alike or different. For example, a -Si$(G)_3$ can be trimethylsilyl, dimethylphenylsilyl, or methylphenylbenzylsilyl. Examples of alkyl of one to 4 carbon atoms, inclusive, are methyl, ethyl, propyl, iospropyl, butyl, isobutyl, sec-butyl, and tert-butyl. Examples of aralkyl of 7 to 12 carbon atoms, inclusive, are benzyl, phenethyl, α-phenylethyl, 3-phenylpropyl, α-naphthylmethyl, and 2-(β-naphthyl)ethyl. Examples of phenyl substituted with one or 2 fluoro, chloro, or alkyl of one to 4 carbon atoms, inclusive, are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

In Chart F, the final PGF$_\alpha$ and PGF$_\beta$ -type products are those encompassed by Formulas LI and LII.

The initial optically active or racemic reactants of Formula XLVIII in Chart F, i.e., the phenyl-substituted PGF$_1$-, PGF$_2$-, dehydro-PGF$_2$-, and dihydro-PGF$_1$-type compounds in their α and β forms, and their esters, are prepared by methods described herein. Thus, racemic phenyl-substituted dihydro-PGF$_{1\alpha}$ -and -PGF$_{1\beta}$ -type compounds, and their esters are prepared by catalytic hydrogenation of the corresonding racemic phenyl-substituted PGF$_{1\alpha}$ or PGF$_{2\alpha}$, and PGF$_{1\beta}$ or PGF$_{2\beta}$ type compounds, respectively, e.g. in the presence of 5% palladiumon-charcoal catalyst in ethyl acetate solution at 25° C. and one atmosphere pressure of hydrogen.

The heretofore-described acids and esters of Formula XLVIII are transformed to the corresponding intermediate 15-oxo acids and esters of Formula XLIX by oxidation with reagents such as 2,3-dichloro-5,6-dicyano-1,4-benzoquinone, activated manganese dioxide, or nickel peroxide (see Fieser et al., "Reagents for Organic Syntheses," pp. 215, 637, and 731). Alternatively, and especially for the Formula XLVIII reactants wherein E and V are -CH$_2$CH$_2$-, these oxidations are carried out by oxygenation in the presence of the 15-hydroxyprostaglandin dehydrogenase of swine lung (see Arkiv för Kemi 25, 293 (1966)). These reagents are used according to procedures known in the art. See, for example, J. Biol. Chem. 239, 4097 (1964).

Referring again to Chart F, intermediate compounds XLIX are transformed to silyl derivatives L by procedures known in the art. See, for example, Pierce, "Silylation of Organic Compounds," Pierce Chemical Co., Rockford, Ill. (1968). Both hydroxy groups of the Formula XLIX reactants are thereby transformed to -O-Si-$(G)_3$ moieties wherein G is as defined above, and sufficient of the silylating agent is used for that purpose according to known procedures. When $R_1$ in intermediate XLIX is hydrogen, the -COOH moiety thereby defined is simultaneously transformed to -COO-Si-$(G)_3$, additional silylating agent being used for this purpose. This latter transformation is aided by excess silylating agent and prolonged treatment. When $R_1$ in Formula XLIX is alkyl, then $R_{14}$ in Formula L will also be alkyl. The necessary silylating agents for these transformations are known in the art or are prepared by methods known in the art. See, for example, Post, "Silicones and Other Organic Silicon Compounds," Reinhold Publishing Corp., New York, N.Y. (1949).

Referring again to Chart F, intermediate silyl compounds L are transformed to the final compounds of Formulas LI and LII by first reacting the silyl compound with a Grignard reagent of the formula $R_{19}$MgHal wherein $R_{19}$ is as defined above, and Hal is chloro, bromo, or iodo. For this purpose, it is preferred that Hal be bromo. This reaction is carried out by the usual procedure for Grignard reactions, using diethyl ether as a reaction solvent and saturated aqueous ammonium chloride solution to hydrolyze the Grignard complex. The resulting disilyl or trisilyl tertiary alcohol is then hydrolyzed with water to remove the silyl groups. For this purpose, it is advantageous to use a mixture of water and sufficient of a water-miscible solvent, e.g., ethanol to give a homogenous reaction mixture. The hydrolysis is usually complete in 2 to 6 hours at 25° C., and is preferably carried out in an atmosphere of an inert gas, e.g., nitrogen or argon.

The mixture of 15-α and 15-β isomers obtained by this Grignard reaction and hydrolysis is separated by procedures known in the art for separating mixtures of prostanoic acid derivatives, for example, by chromatography on neutral silica gel. In some instances, the lower alkyl esters, especially the methyl esters of a pair of 15-α and 15-β isomers are more readily separated by silica gel chromatography than are the corresponding acids. In those cases, it is advantageous to esterify the mixture of acids as described below, separate the two esters, and then, if desired, saponify the esters by procedures known in the art for saponification of prostaglandins F.

Although Formula LI and LII compounds wherein E is -CH$_2$CHR$_4$- and V is D as defined above may be produced according to the processes of Chart F, it is preferred to produce those novel dihydro-PGF$_1$ analogs by hydrogenation of one of the corresponding unsaturated compounds, i.e., a compound of Formula LI or LII wherein E is trans -CH=CR$_4$- and V is either D, -CH=CH-A, or -C≡C-A-, A being defined above. This hydrogenation is advantageously carried out catalytically, for example, in the presence of a 5% palladium-on-charcoal catalyst in ethyl acetate solution at 25° C. and one atmosphere pressure of hydrogen.

The novel 15-alkyl phenyl-substituted PGE-type acids and esters of Formula XI to XIV are prepared from the corresponding PGF compounds, heretofore described, by oxidation. For this purpose, an oxidizing agent is used which selectively oxidizes secondary hydroxy groups to carbonyl groups in the presence of carbon-carbon double bonds. The PGF$_\beta$ isomers are preferred starting materials when the carboxyl side chain is alpha, although the corresponding α-hydroxy isomers are also useful for this purpose.

Oxidation reagents useful for this transformation are known to the art. An especially useful reagent for this purpose is the Jones reagent, i.e., acidified chromic acid. See J. Chem. Soc. 39 (1946). Acetone is a suitable diluent for this purpose, and a slight excess beyond the amount necessary to oxidize one of the secondary hydroxy groups of the 15-alkyl PGF reactant is used. Reaction temperatures at least as low as about 0° C. should be used. Preferred reaction temperatures are in the range −10° to −50° C. The oxidation proceeds rapidly and is usually complete in about 5 to 20 minutes. The excess oxidant is destroyed, for example by addition of a lower alkanol, advantageously, isopropyl alcohol, and the PGE-type product is isolated by conventional methods.

Examples of other oxidation reagents useful for this purpose are silver carbonate on Celite (Chem. Commun. 1102 (1969)), mixtures of chromium trioxide and pyridine (Tetrahedron Letters 3363 (1968), J. Am. Chem. Soc. 75, 422 (1953), and Tetrahedron, 18, 1351 (1962)), mixtures of sulfur trioxide in pyridine and dimethyl sulfoxide (J. Am. Chem. Soc. 89, 5505 (1967)), and mixtures of dicyclohexyl-carbodiimide and dimethyl sulfoxide (J. Am. Chem. Soc. 87, 5661 (1965)).

The novel 15-alkyl phenyl-substituted PGA-type acids and esters of Formulas XIX to XXII are prepared from the 15-alkyl phenyl-substituted PGE compounds, heretofore described, by dehydration. For this purpose, a dehydrating agent is used which removes the hydroxy group from the alicyclic ring in the presence of a hydroxy group on a tertiary carbon atom.

Dehydration agents useful for this transformation are known in the art. Any of the known substantially neutral dehydrating agents is used for these reactions. See Fieser et al., "Reagents for Organic Syntheses", John Wiley & Sons, Inc., New York, 1967. Preferred dehydrating agents are mixtures of at least an equivalent amount of a carbodiimide and a catalytic amount of a copper (II) salt. Especially preferred are mixtures of at least an equivalent amount of dicyclohexylcarbdiimide and a catalytic amount of copper (II) chloride. An equivalent amount of a carbodiimide means one mole of the carbodiimide for each mole of the PGE-type reactant. To ensure completeness of the reaction, it is advantageous to use an excess of the carbondiimide, i.e., 1.5 to 5 or even more equivalents of the carbodiimide.

The dehydration is advantageously carried out in the presence of an inert organic diluent which gives a homogeneous reaction mixture with respect to the PGE-type reactant and the carbodiimide. Diethyl ether is a suitable diluent. It is advantageous to carry out the dehydration in an atmosphere of an inert gas, e.g., nitrogen, helium or argon. The time required for the dehydration will depend in part on the reaction temperature. With the reaction temperature in the range 20° to 30° C., the dehydration usually takes place in about 40 to 60 hours. The PGA-type product is isolated by methods known in the art, e.g., filtration of the reaction mixture and evaporation of the filtrate. If desired, the product is purified by methods known in the art, advantageously by chromatography on silica gel.

The phenyl-substituted PGE, PGF$_\alpha$ and PGF$_\beta$ compounds encompassed by Formulas XI to XVIII, wherein R$_1$ is H, are also prepared by an alternate reaction sequence.

Chart G depicts the series of reactions by which tricyclic lactone aldehyde LVIII is prepared by a procedure known in the art. See U.S. Pat. No. 3,711,515. In said U.S. patent, a reaction sequence for preparing tricyclic lactone aldehyde LVIII is as follows:

a. an optically active or racemic [3.1.0] hex-2-ene-6-carboxaldehyde of Formula LIII is converted to an optically active acetal of the Formula LIV or the mirror image thereof, or a racemic compound of that formula and the mirror image thereof, wherein R$_{21}$ and R$_{22}$ are alkyl of one to 4 carbon atoms, inclusive, or, when taken together,

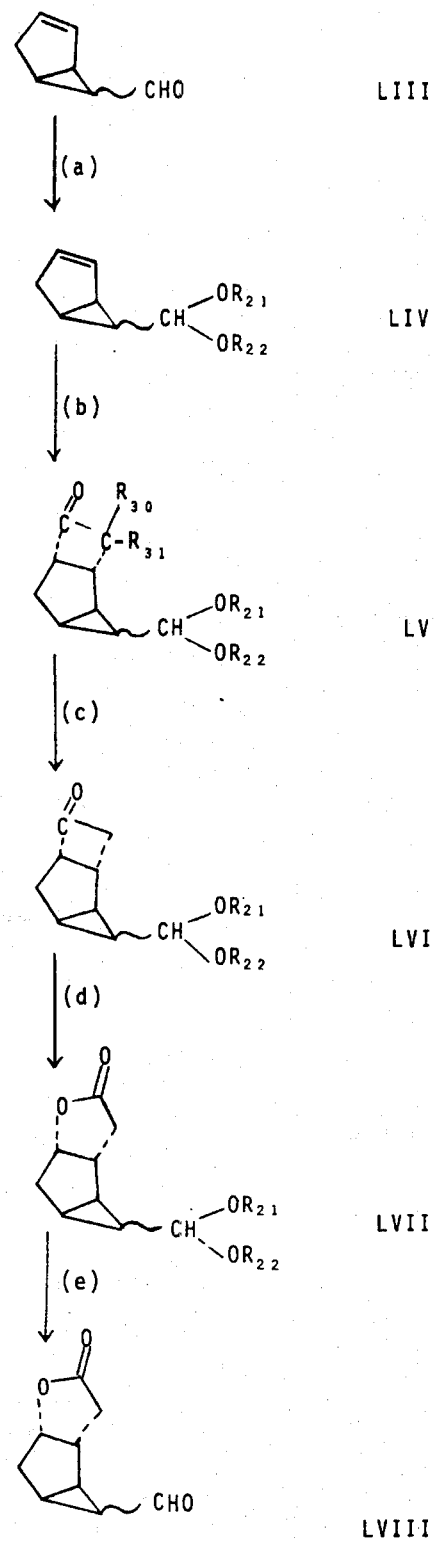

CHART G

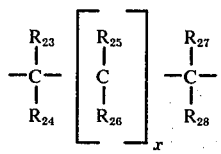

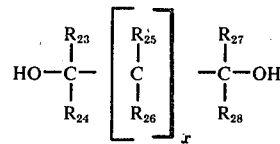

wherein $R_{23}$, $R_{24}$, $R_{25}$, $R_{26}$, $R_{27}$, and $R_{28}$ are hydrogen, alkyl of one to 4 carbon atoms, inclusive, or phenyl, with the proviso that not more than one of the R's is phenyl and the total number of carbon atoms is from 2 to 10, inclusive; $x$ is zero or one; and $\sim$ is as defined above;

b. transforming said optically active or racemic acetal LIV to an optically active tricyclic mono or dihaloketone of the Formula LV or the mirror image thereof, or a racemic compound of that formula and the mirror image thereof, wherein $R_{21}$, $R_{22}$, and $\sim$ are as defined above, and wherein $R_{30}$ is bromo or chloro, and $R_{31}$ is hydrogen, bromo, or chloro;

c. transforming said optically active or racemic tricyclic mono or dihaloketone LV to an optically active tricyclic ketone of the Formula LVI or the mirror image thereof, or a racemic compound of that formula and the mirror image thereof, wherein $R_{21}$, $R_{22}$, and $\sim$ are as defined above;

d. oxidizing said optically active or racemic tricyclic ketone LVI to an optically active tricyclic lactone acetal LVII or the mirror image thereof, or a racemic compound of that formula and the mirror image thereof, wherein $R_{21}$, $R_{22}$, and $\sim$ are as defined above; and e. hydrolyzing said optically active or racemic tricyclic lactone acetal LVII to an optically active tricyclic lactone aldehyde of the Formula LVIII, or the mirror image thereof, or a racemic compound of that formula and the mirror image thereof, wherein $\sim$ is as defined above.

The bicyclic aldehyde of Formula LIII in Chart G exists in a number of isomeric forms. With respect to the attachment of the -CHO group, it exists in two isomeric forms, exo and endo. Also, with respect to the position of the cyclopentene double bond relative to the -CHO group, each of the exo and endo forms exists in two optically active (d- or l-) forms, making in all four isomers. Each of those isomers separately or mixtures thereof undergo the reactions herein for producing prostaglandin intermediates and products. For racemic products the unresolved isomers are used. For the optically active prostaglandins, the aldehyde or subsequent intermediate isomers are resolved by the process disclosed in U.S. Pat. No. 3,711,515 and are used for preparing the optically active products.

In carrying out step a, bicyclic aldehyde LIII is transformed to acetal LIV by methods known in the art. Thus, aldehyde LIII is reacted with either an alcohol of one to 4 carbon atoms, e.g., methanol, ethanol, propanol, or butanol or their isomeric forms, or mixture of such alcohols, or, preferably, a glycol having the formula wherein $R_{23}$, $R_{24}$, $R_{25}$, $R_{26}$, $R_{27}$, and $R_{28}$ are hydrogen, alkyl of one to 4 carbon atoms, inclusive, or phenyl, with the proviso that not more than one of the R's is phenyl and the total number of carbon atoms is from 2 to 10, inclusive; and x is zero or one. Examples of suitable glycols are ethylene glycol, 1,2-propanediol, 1,2-hexanediol, 1,3-butanediol, 2,3-pentanediol, 2,4-hexanediol, 3,4-octanediol, 3,5-nonanediol, 2,2-dimethyl-1,3-propanediol, 3,3-dimethyl-2,4-heptanediol, 4-ethyl-4-methyl-3,5-heptanediol, phenyl-1,2-ethanediol, and 1-phenyl-1,2-propanediol.

The step-a reaction is carried out under a variety of conditions using procedures generally known in the art. Thus, the reactants are dissolved in benzene and the mixture heated to remove the water formed azeotropically. To accelerate the reaction, there may be added an acid catalyst such as p-toluenesulfonic acid, trichloroacetic acid, zinc chloride, and the like. Alternatively, the reactants, together with the acid catalyst and a water scavenger such as trimethyl orthoformate are warmed to 40°–100° C. in an inert solvent such as benzene, toluene, chloroform, or carbon tetrachloride. The ratio of the aldehyde to the glycol is preferably between 1:1 and 1:4.

In transforming acetal LIV to ketone LVI, reactions known in the art for analogous compounds are employed. In carrying out step b, acetal LIV is reacted with ketene $R_{30}R_{31}C=C=O$, for example HBrC=C=O, HClC=C=O, $Br_2C=C=O$, or $Cl_2C=C=O$. For convenience, ketene $Cl_2C=C=O$ is preferred. It is preferably generated in situ by the reaction of a 0.5-to-2.0-fold excess of dichloroacetyl chloride in the presence of tertiary amine, e.g., triethylamine, tributylamine, pyridine, or 1,4-diazabicyclo[2.2.2]octane, in a solvent such as n-hexane. cyclohexane, or mixture of isomeric hexanes (Skellysolve B) at a temperature of from 0° to 70° C. (See, for example, Corey et al., Tetrahedron Letters No. 4, pp. 307–310, 1970). Alternatively, the ketene $Cl_2C=C=O$ is generated by adding a trichloroacyl halide to zinc dust suspended in the reaction vessel, omitting the tertiary amine.

In carrying out step c, mono- or dihaloketone LV is reduced with a 2-to-5-fold excess of zinc dust over the stoichiometric ratio of Zn:2 Cl in methanol, ethanol, ethylene, glycol, and the like, in the presence of acetic acid, ammonium chloride, sodium bicarbonate or sodium dihydrogen phosphate. Alternatively, the reaction is carried out with aluminum amalgam in a water-containing solvent such as methanol-diethyl ether-water, tetrahydrofuran-water or dioxane-water, at about 0°–50° C.

In carrying out step d, tricyclic acetal ketone LVI is converted to a lactone by methods known in the art, for example by reaction with hydrogen peroxide, peracetic acid, perbenzoic acid, m-chloroperbenzoic acid, and the like, in the presence of a base such as alkali hydroxide, bicarbonate, or orthophosphate, using a preferred molar ratio of oxidizer to ketone of 1:1.

In carrying out step e, lactone acetal LVII is converted to aldehyde LVIII by acid hydrolysis, known in the art, using dilute mineral acids, acetic or formic acids, and the like. Solvents such as acetone, dioxane, and tetrahydrofuran are used.

Chart H depicts the series of reactions by which the tricyclic lactone aldehyde LVIII is converted to the bicyclic lactone diol LXIII. Therein, Q is as defined above. In carrying out step a, aldehyde LVIII is converted to the Formula LIX alkene, for example by means of an ylid as in the Wittig reaction.

Certain organic halides, e.g., chlorides and bromides, are necessary to prepare the Wittig reagents used to generate the generic moiety -CH=CHQ of tricycloketone LIX. These organic halides, e.g., $QCH_2CH_2Cl$ and $QCH_2CH_2Br$, are known in the art or can be prepared by methods known in the art. See Table 1 above. The Wittig reagents are prepared by reacting these organic halides with triphenyl phosphine in a known manner, for example 1-bromo-3-phenylpropane is reacted

CHART H

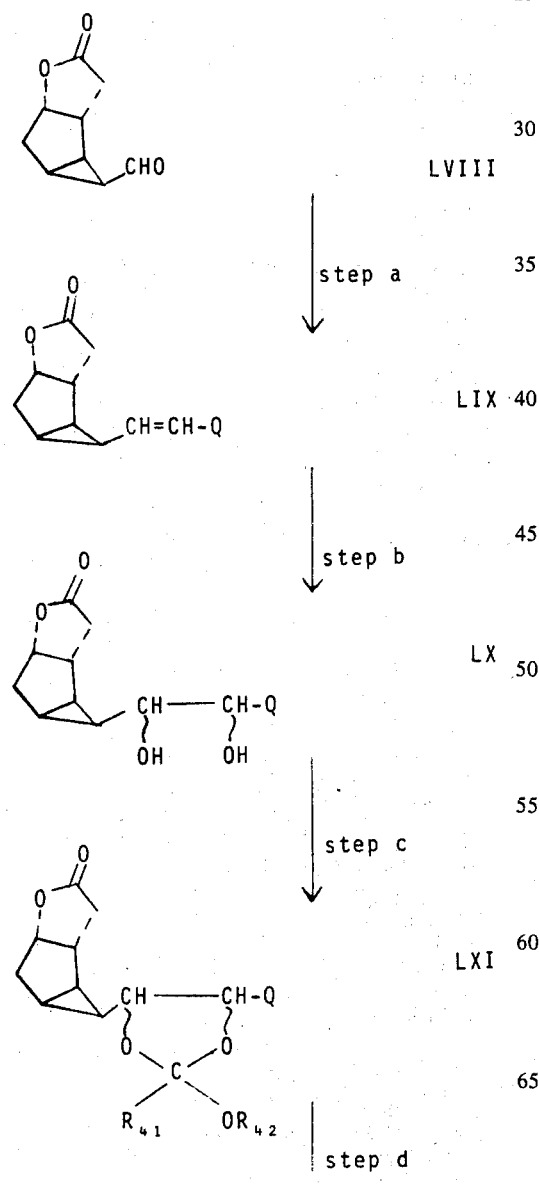

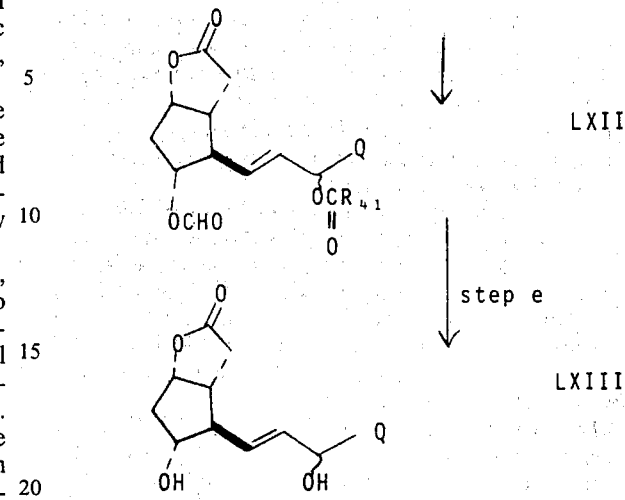

with triphenylphosphine to produce 3-phenylpropane triphenylphosphonium bromide.

In carrying out step b, the alkene LIX is hydroxylated to glycol LX by procedures known in the art. See South African Patent 69/4809 issued July 3, 1970. In the hydroxylation of the respective endo or exo alkenes, various isomeric glycols are obtained depending on such factors as whether the -CH=CH- moiety in LIX is cis or trans, and whether a cis or a trans hydroxylation reagent is used. Thus, endo-cis olefin gives a mixture of two isomeric erythro glycols of Formula LX with a cis hydroxylation agent, e.g., osmium tetroxide. Similarly, the endo-trans olefin gives a similar mixture of the same two erythro glycols with a trans hydroxylation agent, e.g., hydrogen peroxide. The endo-cis olefins and the endo-trans olefins give similar mixtures of two threo glycol isomers with trans and cis hydroxylation reagents, respectively. These various glycol mixtures are separated into individual isomers by silica gel chromatography. However, this separation is usually not necessary, since each isomeric erythro glycol and each isomeric threo glycol is useful as an intermediate according to this invention and the processes outlined in Chart H to produce intermediate products of Formula LXIII and then, according to Chart I hereinafter to produce the other final products of this invention. Thus, the various isomeric glycol mixtures encompassed by Formula LX produced from the various isomeric olefins encompassed by Formula LIX are all useful for these same purposes.

In carrying out step c the optically active tricyclic lactone glycol LX or a racemic compound of that formula and the mirror image thereof, is reacted with an ortho ester of the formula

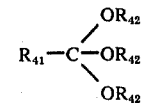

wherein $R_{41}$ is hydrogen, alkyl of one to 19 carbon atoms, inclusive, or aralkyl of 7 to 12 carbon atoms, inclusive, substituted with zero to 3 halo atoms; and $R_{42}$ is methyl or ethyl, to form an optically active cyclic ortho ester of the Formula LXI or a racemic compound of that formula and the mirror image thereof.

In carrying out step d, the cyclic ortho ester LXI is reacted with formic acid to form an optically active diol diester of the Formula LXII or a racemic compound of that formula and the mirror image thereof.

In carrying out step e, the acyl groups of said diol diester LXII are replaced with hydrogen to form the bicyclic lactone diol LXIII.

Previously, steps by which glycol LX is transformed to diol LXIII were disclosed in U.S. Pat. No. 3,711,515, issued Jan. 16, 1973. For example, the glycol hydrogen atoms of glycol LX are replaced by an alkylsulfonyl group and the product subjected to hydrolysis. Alternatively the mixed isomeric glycols LX are transformed to the diformate of bicyclic lactone diol LXIII in 100% formic acid and thence to diol LXIII, e.g. with sodium bicarbonate in methanol.

The transformation of glycol LX to diol LXIII can be accomplished with stereo-specificity and consequently higher yield of the desired isomer by way of a cyclic ortho ester. Reference to Chart H, steps c, d, and e, will make clear the process by which this is accomplished.

In step c of Chart H, tricyclic lactone glycol LX is transformed to cyclic ortho ester LXI. Glycol LX exists in two erythro and two threo forms:

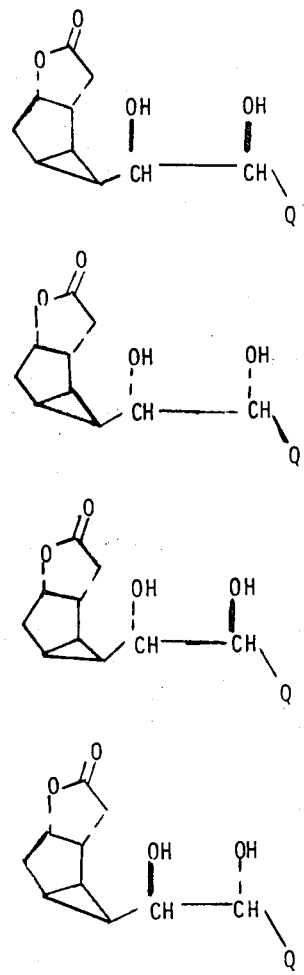

These various glycols are available, for example by hydroxylation of a corresponding alkene or alkenyne as disclosed in the above-referenced U.S. Pat. No. 3,711,515.

Referring to Chart H, the formula LXI cyclic ortho ester is obtained in step c by reaction of glycol LX with an ortho ester of the formula

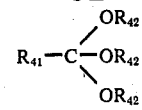

wherein $R_{41}$ and $R_{42}$ are as defined above. The reaction goes smoothly in a temperature range of $-50°$ C. to $+100°$ C., although for convenience $0°$ C. to $+50°$ C. is generally preferred. From 1.5 to 10 molar equivalents of the ortho ester are employed, together with an acid catalyst. The amount of the catalyst is usually a small fraction of the weight of the glycol, say 1% and typical catalysts include pyridine hydrochloride, formic acid, hydrogen chloride, p-toluenesulfonic acid, trichloroacetic acid, or trifluoroacetic acid. The reaction is preferably run in a solvent, for example benzene, dichloromethane, ethyl acetate, or diethyl ether. It is generally completed within a few minutes and is conveniently followed by TLC (thin layer chromatography on basic silica gel plates).

The ortho ester reagents are known in the art or readily available by methods known in the art. See for example S. M. McElvain et al., J. Am. Chem. Soc. 64, 1925 (1942), starting with an appropriate nitrile. Examples of useful ortho esters include:

Trimethyl orthoformate,
triethyl orthoacetate,
triethyl orthopropionate,
trimethyl orthobutyrate,
triethyl orthovalerate,
trimethyl orthooctanoate,
trimethyl orthophenylacetate, and
trimethyl ortho (2,4-dichlorophenyl) acetate.

Preferred are those ortho esters wherein $R_{41}$ is alkyl of one to 7 carbon atoms; especially preferred are those wherein $R_{41}$ is alkyl of one to 4 carbon atoms.

The Formula LXII diester is obtained in step d by reaction of the Formula LXI cyclic ortho ester with anhydrous formic acid. By "anhydrous formic acid" is meant that it contains not more than 0.5% water. The reaction is run with an excess of formic acid, which may itself serve as the solvent for the reaction. Solvents may be present, for example dichloromethane, benzene, or diethyl ether, usually not over 20% by volume of the formic acid. There may also be present organic acid anhydrides, for example acetic anhydride, or alkyl orthoesters, for example trimethyl orthoformate, which are useful as drying agents for the formic acid. Although the reaction proceeds over a wide range of temperatures, it is conveniently run at about $20°-30°$ C. and is usually completed within about 10 minutes. Thereafter the product is recovered and purified if desired by methods known in the art.

The Formula LXIII diol is obtained in step e by alcoholysis of the Formula LXII diester in the presence of a base. Examples of the base are sodium or potassium carbonate or sodium or potassium alkoxides including methoxides or ethoxides. The reaction is conveniently run in an excess of the solvolysis reagent, for example methanol or ethanol. The temperature range is from $-50°$ C. to $100°$ C. The time for completion of the reaction varies with the nature of $R_{41}$ and the base, proceeding in the case of alkali carbonates in a few minutes when $R_{41}$ is hydrogen but taking up to several hours when $R_{41}$ is ethyl, for example.

Referring to Chart I, there are shown alternate routes from diester LXII to diol LXIII. In step a, diester LXII is hydrolyzed to triol acid LXIV, opening the lactone.

The hydrolysis occurs in the presence of a base, such as sodium or potassium carbonate or hydroxide. With alkali carbonates, a solvent containing water, for example methanol-water or tetrahydrofuran-water, is used whereas with alkali hydroxides no water need be added.

Thereafter, triol acid LXIV is transformed to diol LXIII in step *d* by lactonization in the presence of an acid, for example pyridine hydrochloride, hydrogen chloride, p-toluenesulfonic acid, acetic acid, and the like in a solvent such as dichloromethane, benzene, toluene or chloroform at reflux temperature. At temperatures above 100° C., for example in refluxing toluene, the lactonization proceeds without an acid catalyst. The formation of the lactone is conveniently followed by TLC.

Alternatively, when $R_{41}$ is not hydrogen, a monoester of Formula LXV is obtained as in step *b* by preferential alcoholysis of the formyl group of diester LXII. For this purpose methanolysis with potassium bicarbonate or potassium carbonate is useful. This intermediate LXV is useful for either preparing the triol acid LXIV in step C, by alkaline hydrolysis discussed above, or by alkaline alcoholysis for a sufficient time to remove the $$-\underset{\underset{O}{\|}}{C}R_{41} \text{ moiety.}$$

The steps shown in Chart I are directed toward 3S diols of

CHART I

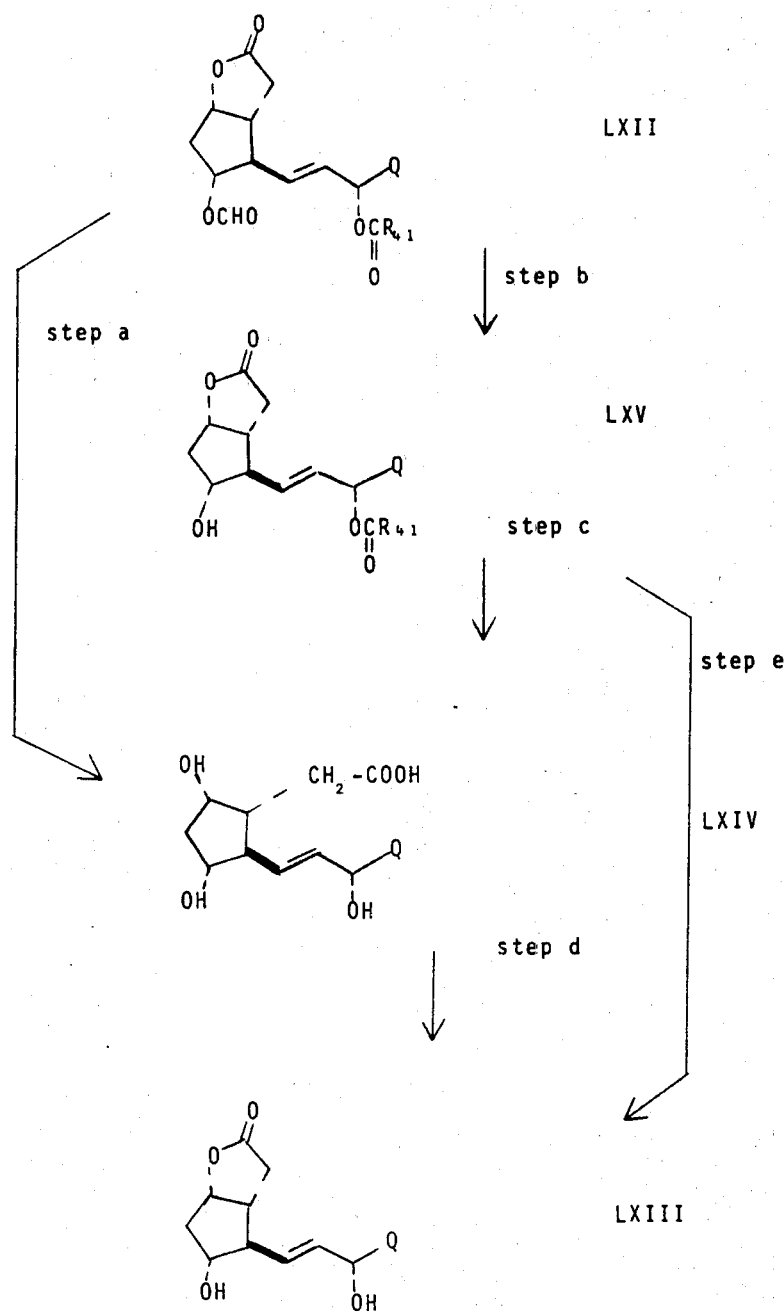

Formula LXIII. By starting with 3R diesters corresponding to Formula LXII, wherein the attachment to C-3 is in the beta configuration, the same chemical transformations yield 3R diols corresponding to Formula LXIII.

The 2R glycols of Formula LXb or LXd by steps of Chart H, yield the 3R formula LXIII diol. When the 3S Formula LXIII diol is desired, there is available a procedure for epimerizing either of the 2R glycols to 2S glycols.

For a discussion of the R and S nomenclature see, for example, R. S. Chan, J. Chem. Ed. 41, 116 (1964). Note that the designation 2S herein refers to the S configuration of C-2, the second carbon in the side chain counting from the ring.

In Chart J are shown the steps by which glycol LXVI is epimerized to glycol LXX. In glycol LXVi the 2-hydroxy is in the R configuration and the 1-hydroxy is in either R or S configuration. In glycol LXX the 2-hydroxy is in the S configuration and the 1-hydroxy is in the same configuration as in LXVI. Thus, in Chart J, ~ indicates attachment of the moiety to the side chain in either alpha or beta configuration. Further, in Chart J, $R_{43}$ and $R_{44}$ are alkyl of one to 10 carbon atoms, inclusive, aralkyl of 7 to 12 carbon atoms, inclusive, phenyl or phenyl substituted with one or 2 halo or alkyl groups of one to 4 carbon atoms, inclusive. If $R_{43}$ is alkyl, it is preferably of 3 or more carbon atoms. $R_{43}$ and $R_{44}$ may be the same or different. For example, $R_{43}$ may be n-butyl when $R_{44}$ is methyl. In Formula LXIX, one of E' and A' is hydrogen and the other is an acyl group of the formula $-C(O)-R_{44}$.

It will be recognized that Formula LXVI includes both glycol LXb and glycol LXd above, obtained by the processes disclosed in U.S. Pat. No. 3,711,515 and that Formula LXX includes

CHART J

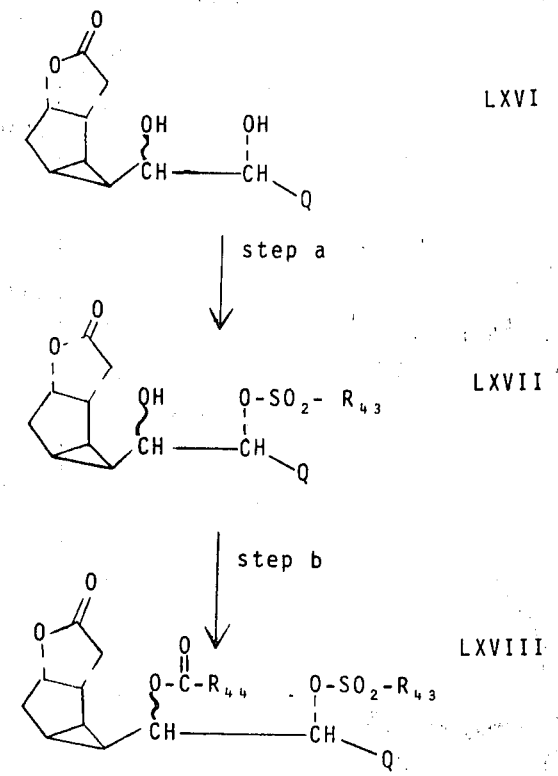

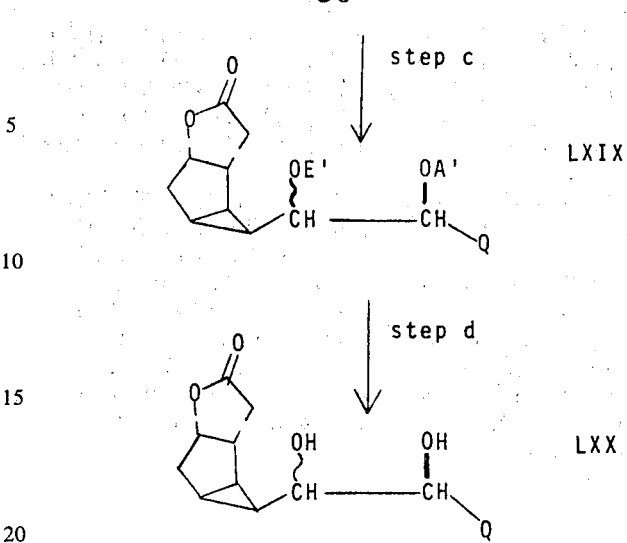

both glycol LSa and glycol LXc, useful for the preparation of diol LXIII by the steps of Charts H and I.

Continuing with Chart J, the formula LXVII sulfonate is obtained in step $a$ by reaction of glycol LXVI with a sulfonyl chloride of the formula $R_{43}-SO_2-Cl$ wherein $R_{43}$ is as above defined. To achieve selective activation of the C-2hydroxyl it is preferred that the $R_{43}$ group contains 3 or more carbon atoms, for example n-butyl, phenyl, or p-tolyl. The reaction is done with about 3 molar equivalents of the sulfonyl chloride in the presence of a tertiary amine. Preferably a solvent system of diethyl ether or dichloromethane containing the tertiary amine, for example pyridine in about 33% by volume, is used. The reaction is run preferably at about 0° C. and is generally complete within 5 days as shown by TLC.

Diester LXVIII is obtained in step $b$ by reaction of sulfonate LXVII with an acid anhydride of formula $(R_{44})_2O$ or acyl halide of the formula $R_{44}Hal$ where Hal is bromo or chloro. Particularly useful for this purpose are acylating agents in which $R_{44}$ is alkyl of one to 3 carbon atoms, inclusive, for example acetic anhydride or propionic anhydride.

Mixed monoesters LXIX are obtained in step $c$ by treatment of diester LXVIII with 90% aqueous acetic acid containing 4 molar equivalents of sodium acetate at 90° C. The reaction is generally completed in a few hours. See R. B. Woodward et al., J. Am. Chem. Soc. 80, 209 (1958).

Finally, glycol LXX is obtained in step $d$ by removal of the acyl group. This is preferably done in absolute methanol with sodium methoxide, followed by quenching in aqueous acetic acid. Alternatively, use of 2 N. sodium hydroxide in methanol-water results in simultaneous lactone-opening and hydrolysis of the acyl group. Acidification to pH 3 restores the lactone ring and permits recovery of glycol LXX.

The steps shown in Chart J are directed toward 2S glycols of Formula LXX. By starting instead, with 2S glycols corresponding to Formula LXVI but with S configuration at C-2, the same chemical transformations yield 2R glycols corresponding to Formula LXX but with R configuration at C-2.

The lactone diol LXIII is transformed to PGE$_2$ or PGF$_{2\alpha}$ by steps known in the art. See E. J. Corey et al., J. Am. Chem. Soc. 91, 5675 (1969). In Chart K are shown the steps leading from lactone diol LXIII to the Formula LXXIV PGF$_{2\alpha}$ compound and the Formula LXXXVI PGE$_2$ compound. In Chart K, J is a blocking group as defined above and M' is either

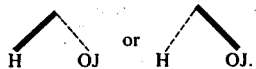 or

Referring to Chart K. compound LXXI is obtained from compound LXIII by introducing blocking groups J. When the blocking group is tetrahydropyranyl or tetrahydrofuranyl, the appropriate reagent, e.g. 2,3-dihydropyran or 2,3-dihydrofuran, is used in an inert solvent such as dichloromethane, in the presence of an acid condensing agent such as p-toluenesulfonic acid or pyridine hydrochloride. The reagent is used in slight excess, preferably 1.0 to 1.2 times theory. The reaction is carried out at about 20°–50° C.

When the blocking group is of the formula

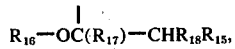

as defined above, the appropriate reagent is a vinyl ether, e.g. isobutyl vinyl ether or any vinyl ether of the formula R$_{16}$-O-C(R$_{17}$)=CR$_{18}$R$_{15}$ wherein R$_{16}$, R$_{17}$, R$_{18}$, and R$_{15}$ are as defined above; or an unsaturated cyclic or heterocyclic compound, e.g. 1-cyclohex-1-yl methyl ether or 5,6-dihydro-4-methoxy-2H pyran. See C. B. Reese et al., J. Am. Chem. Soc. 89,

CHART K

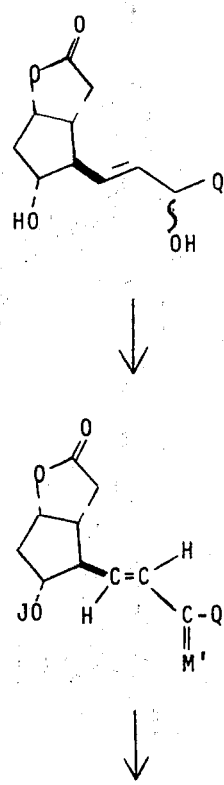

CHART K (Continued)

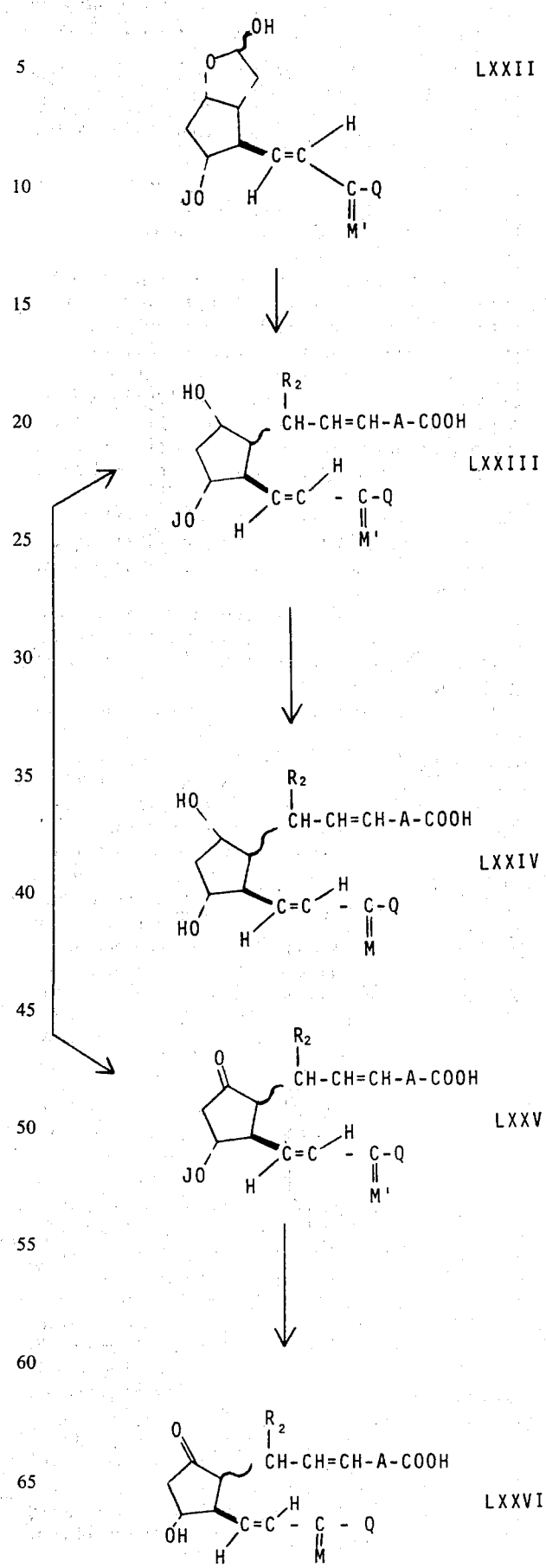

3366 (1967). The reaction conditions for such vinyl ethers and unsaturates are similar to those for dihydropyran above.

The lactol LXXII is obtained on reduction of the formula LXXI lactone without reducing the 13,14-ethylenic group. For this purpose, diisobutylaluminum hydride is used. The reduction is preferably done at −60° to −70° C.

The stereochemistry of the side chain is preserved in transforming LXIII to LXXI to LXXII. For example, a 3-alpha compound LXII yields a 3-alpha compound LXXII.

The Formula LXXIII compound is obtained from the formula LXXII lactol by the Wittig reaction, using a Wittig reagent derived from the appropriate ω-carboxyalkyltriphenyl phosphonium bromide, HOOC-A-CH$_2$-P(C$_6$H$_5$)$_3$Br and sodio dimethylsulfinylcarbanide. The reaction is conveniently carried out in dimethyl sulfoxide at about 25° C. The phosphonium compounds are known in the art or are readily available, e.g., by reaction of an ω-bromoaliphatic acid with triphenyl phosphine.

The Formula LXXIII compound can be converted to the corresponding PGF$_{2\alpha}$ compound LXXIV by removal of the blocking groups J by mild acid hydrolysis, for example using acetic acid.

The Formula LXXIII compound can be converted to the Formula LXXV compound by the Jones reagent, which in turn is converted to the PGE$_2$ compound LXXVI by mild acid hydrolysis.

The formation of PGF$_{2\beta}$ by carbonyl reduction of PGE$_2$ is known in the art. For this reduction, use is made of any of the known ketonic carbonyl reducing agents, which do not reduce ester or acid groups or carbon-carbon double bonds when the latter is undesirable. Examples of those are the metal borohydrides, especially sodium, potassium, and zinc borohydrides, lithium (tri-tert-butoxy) aluminum hydride, metal trialkoxy borohydrides, e.g., sodium trimethoxy borohydride, lithium borohydride, diisobutyl aluminum hydride, and when carbon-carbon double bond, especially cis, reduction is not a problem, the boranes, e.g., disiamylborane. As is known, this method gives a mixture of PGF$_{2\alpha}$ and PGF$_{2\beta}$, which are readily separated by chromatography. The formation of PGA$_2$ by acidic dehydration of PGE$_2$ is known in the art. See, for example, Pike et al., Proc. Nobel Symposium 11, Stockholm (1966), Interscience Publishers, New York, p. 162 (1967), and British Specification 1,097,533. Alkanoic acids of 2 to 6 carbon atoms, inclusive, especially acetic acid, are preferred acids for this acidic dehydration. Dilute aqueous solutions of mineral acids, e.g., hydrochloric acid, especially in the presence of a solubilizing diluent, e.g., tetrahydrofuran, are also useful as reagents for this acidic dehydration.

The phenyl-substituted PGE, PGF$_\alpha$ and PGF$_\beta$ compounds encompassed by Formulas XI to XVIII, wherein R$_1$ is H, are also prepared by yet another reaction sequence depicted in Chart L. This procedure is done by steps known in the art. See E. J. Corey et al., J. Am. Chem. Soc. 91, 5675 (1969). In Chart M, Q, M, M', R$_2$, A and J have the same meanings as defined above. R$_{51}$ is methyl or phenyl.

Subsequent to my invention, K. Mallion reported in South Africa Specification No. 724 372 the synthesis of aryl substituted prostanoic acid derivatives.

The Formula LXXVIII compound is obtained by Wittig alkylation of LXXVII. As the Wittig reagent, there can be used the sodio derivative of the appropriate 2-oxo-phenylalkylphosphonate. The trans enone lactone is obtained stereospecifically (see D. H. Wadsworth et al., J. Org. Chem. Vol. 30, p. 680 (1965)).

CHART L

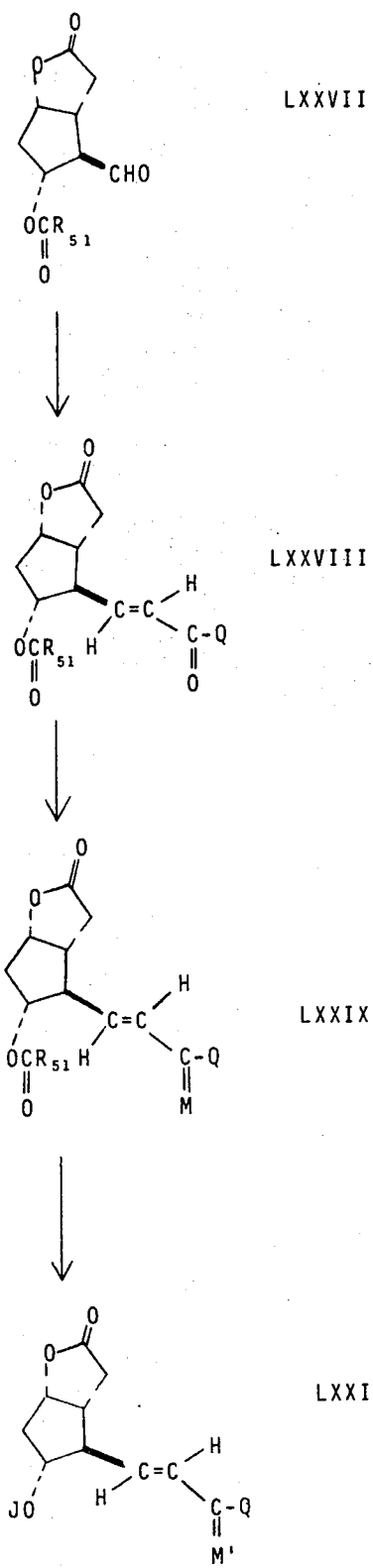

CHART L (Continued)

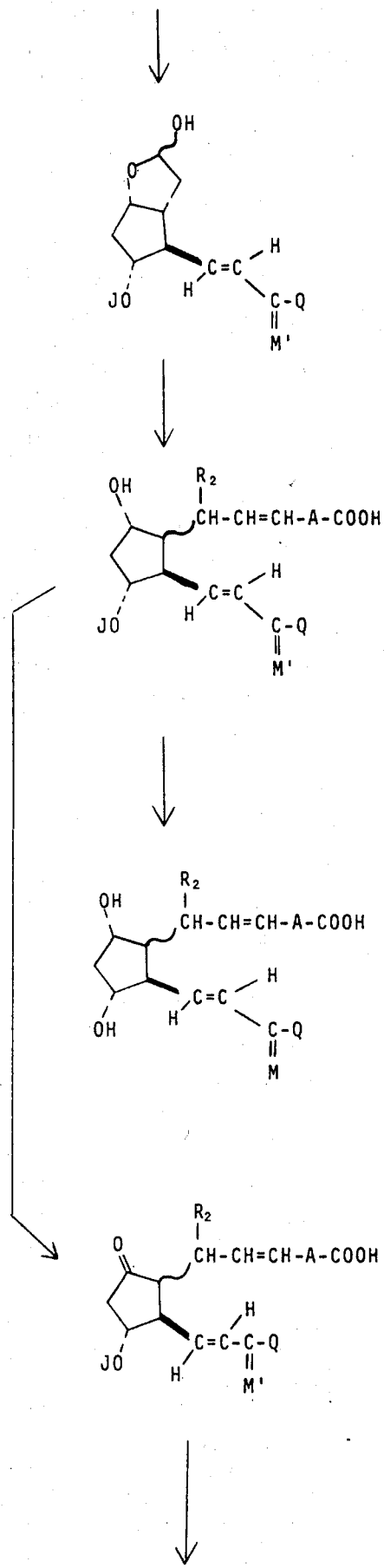

LXXII

LXXIII

LXXIV

LXXV

CHART L (Continued)

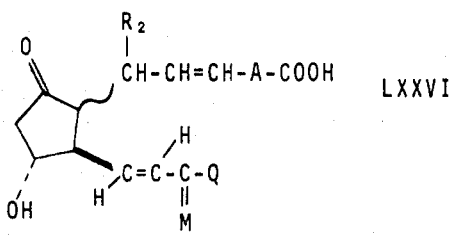

LXXVI

In preparing the Formula LXXVIII compounds of Chart L, certain phosphonates can be employed in the Wittig reaction. These are of the general formula

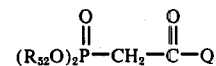

wherein Q is as defined above and $R_{52}$ is alkyl of one to 8 carbon atoms, especially methyl. The phosphonates are prepared and used by methods known in the art. See Wadsworth et al., reference cited above. Conveniently, the appropriate phenyl-substituted aliphatic acid ester is condensed with dimethyl methylphosphonate in the presence of n-butyllithium. For this purpose, acids of the general formula Q-COOH are used in the form of their lower alkyl esters, preferably methyl or ethyl. For this purpose methyl esters are readily formed from the acids by reaction with diazomethane. These aliphatic acids of various chain length, with phenyl substitution within the scope of Q as defined above, are known in the art or can be prepared by methods known in the art.

Alternatively, there can be employed in the reaction the sodio derivative of certain phosphoranes of the formula

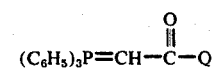

wherein Q is as defined above. These phosphoranes are prepared and used by methods known in the art. Conveniently, the appropriate ketone compound of the formula Q-CO-CH$_2$-Hal, wherein Hal is chloro, bromo or iodo, is condensed with triphenylphosphine and the condensation product is treated with alkali to produce the desired phosphorane compound. The halo-ketone starting compound is prepared in a known way. For example, an organic halide (see Tables 1 and 2) corresponding to Q minus a methylene group, is reacted with epihalohydrin to form

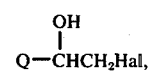

which is then oxidized with Jones reagent to form the starting halo-ketone compound.

Continuing with Chart L, the Formula LXXIX compound is obtained as a mixture of alpha and beta isomers by reduction of LXXVIII. For this reduction, use is made of any of the known ketonic carbonyl reducing agents which do not reduce ester or acid groups or carbon-carbon double bonds when the latter is undesirable. Examples of those are the metal borohydrides, especially sodium, potassium, and zinc borohydrides, lithium (tri-tert-butoxy)aluminum hydride, metal trialkoxy borohydrides, e.g., sodium trimethoxyborohydride, lithium borohydride, diisobutyl aluminum hydride, and when carbon-carbon double bond reduction is not a problem, the boranes, e.g., disiamylborane.

For production of natural-configuration PG-type compounds, the desired 15-alpha form of the formula-LXXIX compound is separated from the 15-beta isomer by silica gel chromatography.

The Formula LXXI compound is then obtained by deacylation of LXXIX with an alkali metal carbonate, for example potassium carbonate in methanol at about 25° C., followed by introduction of blocking groups to form compound LXXI. For example, the bis(tetrahydropyranyl)ether LXXI is obtained by reaction with dihydropyran in an inert solvent, e.g. dichloromethane, in the presence of an acid condensing agent such as p-toluenesulfonic acid or pyridine hydrochloride. The dihydropyran is used in excess, preferably 4 to 10 times theory. The reaction is normally complete in 15–30 min. at 20°–30° C.

The lactol LXXII is obtained on reduction of the Formula LXXI lactone or its 15 $\beta$ epimer without reducing the 13,14-ethylenic group. For this purpose, diisobutyl-aluminum hydride is used. The reduction is preferably done at −60° to −70° C. The 15 $\beta$ -epimer of the Formula LXXI lactone is readily obtained by the steps of Chart L, using the 15 $\beta$ isomer of Formula LXXIX.

The Formula LXXIII compound is obtained from the Formula LXXII lactol by the Wittig reaction, using a Wittig reagent derived from the appropriate ω-carboxyalkyltriphenylphosphonium bromide, HOOC-A-CH$_2$-P(C$_6$H$_5$)Br, and sodio dimethylsulfinylcarbanide. The reaction is conveniently carried out at about 25° C. This Formula LXXIII compound serves as an intermediate for preparing either the PGF$_2\alpha$ -type or the PGE$_2$-type product (Chart K). The phosphonium compounds are known in the art or are readily available, e.g., by reaction of an ω-bromoaliphatic acid with triphenylphosphine.

The processes above for phenyl-substituted PG-type compounds lead either to acids or to esters. When an acid has been prepared and an alkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, for example, gives the ethyl, butyl, and 2-ethylhexyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley & Sons, Inc., New York, N.Y., Vol. 8, pp. 389–394 (1954)..

An alternative method for esterification of the carboxyl moiety of the PGF-type of PGE-type compounds comprises transformation of the free acid to the corresponding silver salts, followed by interaction of the salt with an alkyl iodide. Examples of suitable iodides are methyl iodide, ethyl iodide, butyl iodide, isobutyl iodide, tert-butyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

Pharmacologically acceptable salts of the phenyl-substituted PG-type compounds are prepared from the free acids by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the Formula XI-to-XXVI acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To product an amine salt, the Formula XI-to-XXVI acid is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the Formula XI-to-XXVI acid with the stoichiometric amount of the corresponding quaternary ammonium hydroxide in water solution, followed by evaporation of the water.

The final Formula XI-to-XXVI acids or esters prepared by the processes of this invention are transformed to lower alkanoates by interaction of the Formula XI-to-XXVI hydroxy compound with a carboxyacylating agent, preferably the anhydride of a lower alkanoic acid, i.e., an alkanoic acid of one to 8 carbon atoms, inclusive. For example, use of acetic anhydride gives the corresponding diacetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction diluent and solvent. An inert organic diluent, for example dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24-hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxylate is recovered from the diethyl ether extract by evaporation. The carboxylate is then purified by conventional methods, advantageously by chromatography.

By this procedure, the Formula XI-to-XIV PGE-type compounds are transformed to dialkanoates, the Formula XV-to-XVIII PGE-type compounds are transformed to trialkanoates, and the Formula XIX-to-XXVI PGA-type and PGB-type compounds are transformed to monoalkanoates.

When a PGE-type dialkanoate is transformed to a PGF-type compound by carbonyl reduction as shown in Chart A, a PGF-type dialkanoate is formed and is used for the above-described purposes as such or is transformed to a trialkanoate by the above-described procedure. In the latter case, the third alkanoyloxy group can be the same or different from the two alkanoyloxy groups present before the carbonyl reduction.

In Charts A–L above, the formulas as depicted represent optically active compounds having the same absolute configuration as naturally-occurring $PGE_1$. When the same process steps are applied to the enantiomers, i.e. the compounds represented by the mirror images of the depicted formulas, the enantiomeric products are obtained. Likewise, using racemic starting materials consisting of the optically active compounds as depicted and the mirror images thereof, those process steps yield the corresponding racemic intermediates or racemic PG-type products.

When an optically active final compound is desired, that is made by resolution of the racemic compound or by resolution of one of the asymmetric racemic intermediates. These resolutions are carried out by procedures known in the art. For example, when final compound XI to XXVI is a free acid, the racemic (d1) form thereof is resolved by reacting said free acid by known general procedures with an optically active base, e.g., brucine or strychnine, to give a mixture of two diastereoisomers which are separated by known general procedures, e.g., fractional crystallization. The separate diastereoisomeric salts are then treated with an acid by known methods to yield the optically active acid to Formula XI to XXVI. Alternatively, the free-acid form of olefin XXXVI, cyclic ketal XXX, or glycols XXXI or XXXVII is resolved into separate optically active forms and then esterified and transformed further to the corresponding optically active form of the final product XI to XXVI as described above.

Alternatively, glycol reactants XXXI or XXXVII, in exo or endo form, are transformed to ketals with an optically active 1,2-glycol, e.g., D-(—)-2,3-butanediol, by reaction of said 1,2-glycol with the Formula-XXXI or XXXVII compound in the presence of a strong acid, e.g., p-toluenesulfonic acid. The resulting ketal is a mixture of diastereoisomers which are separated, and then hydrolyzed with an acid, e.g., oxalic acid, to the original keto compound, now in optically active form. These reactions involving optically active glycols and ketals for resolution purposes are generally known in the art. See, for example, Chem. Ind. 1664 (1961) and J. Am. Chem. Soc. 84, 2938 (1962). Dithiols may be used instead of glycols.

DESCRIPTION OF THE PREFERRED EMBODIMENTS

The invention can be more fully understood by the following Preparations and Examples:

All temperatures are in degrees centigrade.

Infrared absorption spectra are recorded on a Perkin-Elmer Model 421 infrared spectrophotometer. Except when specified otherwise, undiluted (neat) samples are used.

NMR spectra are recorded on a Varian A-60 spectrophotometer on deuterochloroform solutions with tetramethylsilane as an internal standard (downfield).

Mass spectra are recorded on either an Atlas CH-4 mass spectrometer with a TO-4 source (ionization voltage 70 ev) or a CEC 110B High Resolution Mass Spectrometer, using the trimethylsilylated derivatives.

Collection of chromatographic eluate fractions starts when the eluant front reaches the bottom of the column.

"Brine", herein, refers to an aqueous saturated sodium chloride solution.

The A-IX solvent system used in thin layer chromatography (TLC) is made up from ethyl acetate-acetic acid-2,2,4-trimethylpentane-water (90:20:50:100) according to M. Hamberg and B. Samuelsson, J. Biol. Chem. 241, 257 (1966).

Ultraviolet spectra are recorded on a Cary Model 15 spectrophotometer.

"Skellysolve-B" refers to mixed isomeric hexanes.

Silica gel chromatography, as used herein, is understood to include elution, collection of fractions, and combination of those fractions shown by TLC (thin layer chromatography) to contain the desired product free of starting material and impurities.

Preparation 1 (3-Phenylpropyl)triphenylphosphonium Bromide

A solution of 597.3 g. of (3-bromopropyl) benzene and 786 g. of triphenylphosphine in 1500 ml. of toluene is heated at reflux under nitrogen for 16 hrs., then the mixture is cooled and the solid product is separated by filtration. The solid is then slurried with toluene in a Waring blender, separated by filtration, and dried for 18 hrs. at 70° C. under reduced pressure to give 1068 g. of (3-phenylpropyl)triphenylphosphonium bromide; m.p. 210.5°–211.5° C.

Preparation 2 (4-Phenylbutyl)triphenylphosphonium Bromide a. 4-Phenyl-1-butanol.- A solution of 200 g. of 4-phenylbutyric acid in 1500 ml. of anhydrous ether is added with stirring to a suspension of 46.3 g. of lithium aluminum hydride in 1800 ml. of anhydrous ether at a rate sufficient to maintain gentle reflux while the mixture is cooled in an ice bath. Fifteen minutes after the addition is complete the mixture is treated cautiously, under nitrogen, wit 93 ml. of water and then 74 ml. of 10% aqueous sodium hydroxide. The mixture is stirred about 18 hrs. at about 25° C. and dried over sodium sulfate, filtered, and concentrated under reduced pressure to give 171 g. of 4-phenyl-1-butanol; infrared absorption at 3250, 2980, 1610, 1060, 1030, 750 and 700 cm$^{-1}$; NMR peaks at 7.30 (singlet), 3.61 (triplet), 2.65 (multiplet) and 2.75 (singlet) δ.

b. (4-Bromobutyl)benzene.- Phosphorus tribromide (40.5 ml.) is added dropwise to 171 g. of 4-phenyl-1-butanol with cooling to keep the temperature between 0° C. and −5° C. This mixture is allowed to stand 16 hrs. at 25° C. and is poured into a mixture of ice and aqueous sodium bicarbonate. The mixture is extracted with hexane and the extract is washed with water, aqueous sodium bicarbonate, brine, dried over sodium sulfate and concentrated under reduced pressure to give 196 g. of (4-bromobutyl)-benzene. This is distilled to give 145.2 g., b.p. 103°–103.5°/16 mm; NMR peaks at 7.19 (multiplet), 3.14 (triplet) and 2.45 δ.

c. (4-Phenylbutyl)-triphenylphosphonium bromide.- A solution of 145 g. of (4-bromobutyl)benzene and 179 g. of triphenylphosphine in 350 ml. of toluene is heated at reflux under nitrogen for 16 hrs. The mixture is then cooled slowly and ether is added giving a precipitate of the title compound which is washed thoroughly with benzene/ether and dried 18 hrs. at 50° C. under reduced pressure, 268 g., m.p. 139°–140° C.

Preparation 3 (2-Phenylethyl)triphenylphosphonium Bromide

Following the procedure of Preparation 1 but replacing (3-bromopropyl)benzene with the equivalent amount of (2-bromoethyl)benzene, there is obtained the title compound.

Preparation 4
(2,2-Dimethyl-3-phenylpropyl)triphenylphosphonium Bromide a. (3-Bromo-2,2-dimethylpropyl)benzene.- Following the procedure of Preparation 2b but replacing 4-phenyl-1-butanol with the equivalent amount of 2,2-dimethyl-3-phenyl-1-propanol, there is obtained (3-bromo-2,2-dimethylpropyl)-benzene.

b. (2,2-Dimethyl-3-phenylpropyl)triphenylphosphonium bromide.- Following the procedure of Preparation 1 but replacing (3-bromopropyl)benzene with the equivalent amount of (3-bromo-2,2-dimethylpropyl)benzene, there is obtained the title compound.

Preparation 5 Ethyl cis-7-iodo-5-heptenoate a. Ethyl cis-7-chloro-5-heptenoate.- A solution of ethyl cis-7-chloro-5-heptynoate (Chemical Abstracts 55, 17485 d, 1961) (2.0 g.) in 10 ml. of pyridine is hydrogenated in the presence of a 5% palladium on barium sulfate catalyst (150 mg.) at 25° C. and one atmosphere. The resulting mixture is filtered and evaporated to about one-third the original volume. Four volumes of ethyl acetate is added, and the remaining pyridine is removed by addition of ice and one N hydrochloric acid. The ethyl acetate layer is separated, washed successively with one N hydrochloric acid and brine, dried and concentrated. The residue is chromatographed on silica gel which has previously been acid-washed to pH 4 (Silicar CC$_4$, 100–200 mesh, Mallincrodt Co.), eluting with a 25–75% ethyl acetate-Skellysolve B gradient, collecting fractions. The fractions shown to have the desired product free of starting material by TLC are combined and evaporated under reduced pressure to give ethyl cis-7-chloro-5-heptenoate.

b. Ethyl cis-7-iodo-5-heptenoate.- A solution of the ester from step a above (1.8 g.) in dry acetone (100 ml.) is mixed with sodium iodide (5 g.) and the mixture stirred and heated at reflux one hour, then kept at about 25° C. for 15 hrs. The solvent is removed under reduced pressure, and the residue is extract4d with diethyl ether. The extract is washed with water and brine, then dried and concentrated. The residue is chromatographed on silica gel, eluting with 10% ethyl acetate in Skellysolve B. Fractions shown by TLC to contain the product are combined and evaporated to give the title compound.

Preparation 6 2,2,2-Trichloroethyl cis-9-Bromo-7-nonenoate a. 1-Tetrahydropyranyloxy-6-bromohexane.- Concentrated hydrobromic acid (75 drops of 48%) is added with stirring to a mixture of 6-bromohexanol (250g.) and dihydropyran (300 ml.) at 0° C. This mixture is stirred and allowed to warm slowly to 25° C. during 15 hrs. Evaporation under reduced pressure gives a residue which is divided into two equal parts, each part being chromatographed on 1.5 kg. of silica gel, each column being eluted with 7.5 l. of 5% ethyl acetate in Skellysolve B, collecting 500 ml. fractions. Fractions containing the title compound are combined and concentrated.

b. 9-Tetrahydropyranyloxynon-2-yne-1-ol.- Lithium metal (7.7 g.) is added in small pieces with stirring to a solution of ferric nitrate (300 mg.) in 1 l. of liquid ammonia. The mixture is then stirred under reflux until the blue color is replaced by a pale grey color. Then, a solution of propargyl alcohol (28 g.) in 250 ml. of diethyl ether is added slowly with stirring. After stirring 2 hrs. under reflux, a solution of the product of step a above (about 110 g.) in 250 ml. of diethyl ether is added slowly with stirring. After stirring 4 hrs. under reflux, there is added 300 ml. of water and then 300 ml. of diethyl ether. The mixture is stirred about 15 hrs., the ammonia evaporating during that time. The ether layer is separated, washed with water and with brine, dried, and concentrated under reduced pressure to a residue. The residue is chromatographed on 4 kg. of silica gel, eluting with 8 l. 20%, 6 l. 40%, and 6 l. 60%, ethyl acetate-Skellysolve B mixtures, collecting 1.5 l. fractions. Those fractions containing the title compound are combined and concentrated.

c. 1-Bromo-9-tetrahydropyranyloxynon-2-yne.- Methanesulfonyl chloride (20.3 ml.) is added slowly with stirring to a solution of the product of step b above (about 50 g.) in 400 ml. of pyridine at −20° C. The mixture is stirred one hour at −20° C., and then is poured into a stirred mixture of 3 N. hydrochloric acid (1727 ml.) and 2540 ml. of ice water. This mixture is extracted with diethyl ether. The ether extract is washed with cold one normal hydrochloric acid and then with brine, dried, and concentrated at reduced pressure. The residue is dissolved in 500 ml. of dry acetone. Lithium bromide (26 g.) is added to the acetone solution, and the mixture is stirred and heated at reflux one hour, and then kept at 25° C. for 15 hrs. The acetone is evaporated under reduced pressure, and the residue is extracted with diethyl ether. The ether extract is washed with water and then three times with brine, dried, and concentrated. The residue is chromatographed on 3.5 kg. of silica gel, eluting with 24 l. of 10% ethyl acetate in Skellysolve B, collecting 1.5 l. fractions. Those fractions containing the title compound are combined and concentrated.

d. 9-Bromo-7-nonynoic acid and its 2,2,2-trichloroethyl ester.- The product of step c above is contacted with a mixture of acetic acid/water/tetrahydrofuran (20/10/3) at 40° C. for 2 hrs., thereafter removing solvents under reduced pressure. The resulting hydroxy compound is then oxidized to the acid in acetone solution, using a slight excess of Jones reagent (21 g. chromic anhydride/60 ml. water/17 ml. conc. sulfuric acid) while cooling to maintain a temperature of −5° to 0° C. After about 60 min., isopropyl alcohol is added, the mixture is stirred for 10 min., and then poured into ice water. The acid product is isolated by extraction with chloroform, drying over sodium sulfate, and concentration under reduced pressure.

The ester is prepared by contacting the acid with equivalent amounts of 2,2,2-trichloroethanol, pyridine, and dicyclohexylcarbodiimide in dichloromethane for about 3 hrs. at 25° C. under nitrogen. Water (16 ml.) is then added, and the mixture is stirred 10 minutes. The dichloromethane is evaporated under reduced pressure, and the residue is extracted repeatedly with ethyl acetate. The combined extracts are washed with ice-cold one normal hydrochloric acid and then filtered. The filtrate is washed with aqueous sodium bicarbonate solution and then with brine, dried, and evaporated under reduced pressure. The residue is chromatographed on silica gel, eluting with a 20–100% ethyl acetate-Skellysolve B gradient, collecting fractions. Those fractions containing the ester are combined and concentrated under reduced pressure.

e. 2,2,2-Trichloroethyl cis-9-bromo-7-nonenoate.- Following the procedure of step a of Preparation 5, but replacing ethyl cis-7-chloro-5-heptynoate with the ester of step d above, there is obtained the desired title compound.

EXAMPLE 1

Endo-6-(cis-4-phenyl-1-butenyl)-bicyclo[3.1.0]hexan-3-one (Formula XXVII: Q is

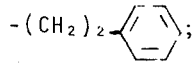

$R_3$ and $R_4$ are hydrogen; and ~ is endo).

Refer to Chart E. A suspension of 314 g. of (3-phenylpropyl)triphenylphosphonium bromide (Preparation 1) in 3 l. of benzene is stirred at about 25° C. under nitrogen, and 400 ml. of 1.6 M butyllithium in hexane is added over a 20 min. period. The mixture is heated at 35° C. for 30 min., then is cooled to −15° C. and a solution of 100 g. of endo-bicyclo[3.1.0]hexan-3-ol-6-carboxaldehyde 3-tetrahydropyranyl ether in 200 ml. of benzene is added over a 30-min. period. This mixture is heated at 70° C. for 2.5 hrs., cooled, and filtered. The filtrate is washed three times with water, dried over sodium sulfate, and evaporated to give 170 g. of crude endo-6-(cis-4-phenyl-1-butenyl)-bicyclo[3.1.0]hexan-3-ol 3-tetrahydropyranyl ether.

A solution of 340 g. (two runs) of this crude endo-6-(cis-4-phenyl-1-butenyl)-bicyclo[3.1.0]hexan-3-ol 3-tetrahydropyranyl ether and 20 g. of oxalic acid in 3600 ml. of methanol is heated at reflux for 3.5 hrs. The mixture is cooled and the methanol is evaporated under reduced pressure. The residue is mixed with dichloromethane, and the dichloromethane solution is washed with aqueous sodium bicarbonate, dried over sodium sulfate, and evaporated to give 272 g. of endo-6-(cis-4-phenyl-1-butenyl)-bicyclo[3.1.0]hexan-3-ol.

A solution of 93 g. of the above endo-6-(cis-4-phenyl-1-butenyl)bicyclo[3.1.0]hexan-3-ol in 2570 ml. of acetone is cooled to −5° C. and 160 ml. of Jones reagent (see J. Chem. Soc. 39 (1946)) is added over a period of 30 min. while cooling to maintain a temperature of −5° C. The mixture is left standing for 10 min. longer; then 100 ml. of isopropyl alcohol is added and the mixture is swirled for 5 min. The mixture is then diluted with 6 l. of water and extracted several times with dichloromethane. The organic layers are combined, washed with dilute hydrochloric acid, water, dilute aqueous sodium bicarbonate, and brine, then dried over sodium sulfate, and evaporated to give the title compound (83 g. of product).

The above product (162 g., two runs) is dissolved in isomeric hexanes (Skellysolve B) and chromatographed over 5 kg. of silica gel wet-packed with Skellysolve B, eluting successively with 11 l. of Skellysolve B, 62 l. of 2.5% ethyl acetate in Skellysolve B, and 32 l. of 5% ethyl acetate in Skellysolve B. The last 8 l. of the 2.5% ethyl acetate in Skellysolve B eluates and the 32 l. of 5% ethyl acetate in Skellysolve B eluates are combined and evaporated to give 75.8 g. of the title compound; infrared absorption at 3000, 1750, 1610, 1500, 1455, 1405, 1265, 1150, 778, 750, and 702 $cm^{-1}$., NMR peaks at 7.18 (singlet) and 4.75–6.0 (broad multiplet) δ.

EXAMPLE 2

Endo-6-(cis-5-phenyl-1-pentenyl)-bicyclo[3.1.0]hexan-3-one. (Formula XXVII: Q is

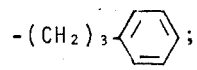

$R_3$ and $R_4$ are hydrogen; and ~ is endo.

Following the procedure of Example 1, but using (4-phenylbutyl)triphenylphosphonium bromide (Preparation 2) instead of (3-phenylpropyl)triphenylphosphonium bromide, there is obtained the corresponding title compound; infrared absorption at 2980, 1745, 1600, 1490, 1450, 1400, 1260, 1145, 770, 750 and 702 $cm^{-1}$., NMR peaks at 7.17 (singlet), 6.0–5.4 (mutliplet), and 5.2–4.7 (broad multiplet) δ.

Following the procedure of Example 1, but using intermediate quaternary phosphonium halides prepared following Preparation 1 from α-bromotoluene, (2-bromoethyl)benzene (see Preparation 3 above), (5-chloropentyl)benzene, (6-bromohexyl)benzene, and (7-iodoheptyl)benzene in place of (3-bromopropyl)benzene, there are obtained the 2-phenyl-1-ethenyl, 3-phenyl-1-propenyl, 6-phenyl-1-hexenyl, 7-phenyl-1-heptenyl, and 8-phenyl-1-octenyl compounds corresponding to the products of Examples 1 and 2.

Also following the procedure of Example 1, but using intermediate quaternary phosphonium halides prepared following Preparation 1 from (1-chloroethyl)benzene, (1-bromo-propyl)-benzene, (2-bromopropyl)benzene, (3-bromo-2,2-dimethylpropyl)-benzene (see Preparation 4), (3-chloropentyl)benzene, (4-bromopentyl)benzene, (6-bromononyl)benzene and (7-bromononyl)-benzene in place of (3-bromopropyl)benzene, there are obtained the 2-methyl-2-phenyl-1-ethenyl, 2-ethyl-2-phenyl-1-ethenyl, 2-methyl-3-phenyl-1-propenyl, 3,3-dimethyl-4-phenyl-1-butenyl, 2-ethyl-4-phenyl-1-butenyl, 2-methyl-5-phenyl-1-pentenyl, 2-propyl-7-phenyl-1-heptenyl, and 2-ethyl-8-phenyl-1-octenyl compounds corresponding to the products of Examples 1 and 2.

Also following the procedure of Example 1, but using intermediate quaternary phosphonium halides prepared as in Preparation 1 from (2-bromo-1-fluoroethyl)benzene, (2-bromo-1-fluoropropyl)benzene, (2-chloro-1-fluoro-1-methylpropyl)-benzene, (5-bromo-4-fluoropentyl)benzene, (7-iodo-6-fluoroheptyl)benzene, (4-bromo-3,3-difluorobutyl)benzene, and (6-bromo-5,5-difluorohexyl)benzene in place of (3-bromopropyl)-benzene, there are obtained the 3-fluoro-3-phenyl-1-propenyl, 3-fluoro-1-methyl-3-phenyl-1-propenyl, 3-fluoro-2,3-dimethyl-3-phenyl-1-propenyl, 3-fluoro-6-phenyl-1-hexenyl, 3-fluoro-8-phenyl-1-octenyl, 3,3-difluoro-5-phenyl-1-pentenyl, and 3,3-difluoro-7-phenyl-1-heptenyl compounds corresponding to the products of Examples 1 and 2.

Also following the procedure of Example 1, but using intermediate quaternary phosphonium halides prepared as in Preparation 1 from α-bromo-m-xylene, α-chloro-p-ethyl-toluene, α-bromo-p-chlorotoluene, α'-chloro-α,α,α-trifluoro-m-xylene, 1-(2-bromoethyl)-4-fluorobenzene, 1-(5-bromopentyl)2-chlorobenzene, 4-(3-iodopropyl)-1,2-dimethoxybenzene, and 1-(3-bromohexyl)-2,4,6-trimethylbenzene in place of (3-bromopropyl)-benzene, there are obtained the 2-(3-methylphenyl)-1-ethenyl, 2-(4-ethylphenyl)-1-ethenyl, 2-(4-chlorophenyl)-1-ethenyl, 2-[3-(trifluoromethyl)-phenyl]-1-ethenyl, 3-(4-fluoro-phenyl)-1-propenyl, 6-(2-chlorophenyl)-1-hexenyl, 4-(3,4-dimethoxyphenyl)-1-butenyl, and 7-(2,4,6-trimethylphenyl)-1-heptenyl compounds corresponding to the products of Examples 1 and 2.

Also following the procedures of Example 1, but using quaternary triphenyl phosphonium halides prepared from other primary and secondary halides of the formula

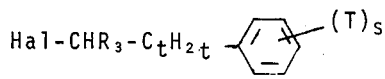

wherein in Hal, $R_3$, -$C_tH_{2t}$-, T and s are as defined above in place of (3-bromopropyl)benzene, there are obtained compounds corresponding to the products of Example 1 with

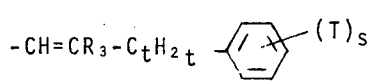

in place of the 4-phenyl-1-butenyl moiety.

Also following the procedure of Example 1, but using bicyclo[3.1.0]hexane reactants with

in place of

wherein $R_4$ is as defined above, there are obtained compounds corresponding to the products of Example 1 with

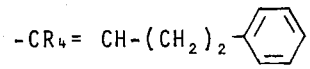

in place of the 4-phenyl-1-butenyl moiety.

Also following the procedure of Example 1, but using exobicyclo[3.1.0]hexane reactants in place of each of the endo reactants defined in Example 1 and above, the exo products are obtained corresponding to the endo products of Examples 1 and 2 and above.

By the above-described procedures, each of the reactants encompassed by Formula XXVII, above, is prepared.

EXAMPLE 3 dl-Methyl 7-[endo-6-(cis-4-phenyl-1-butenyl)-3-oxobicyclo[3.1.0]hex-2αyl)heptanoate. (Formula XXXVI:

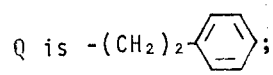

$R_2$, $R_3$, and $R_4$ are hydrogen; $R_{10}$ is methyl; Z is -(CH$_2$)$_5$-; and ~ is endo and alpha).

Refer to Chart D. Two procedures are used.

A. A solution of 17.4 g. of endo-6-(cis-4-phenyl-1-butenyl)-bicyclo[3.1.0]hexan-3-one (Example 1) and 62.5 g. of methyl ω-iodoheptanoate in 375 ml. of tetrahydrofuran (THF) is stirred at about 25° C. under a nitrogen atmosphere and a solution of 13.1 g. of potassium t-butoxide and 13.1 g. of dicyclohexyl-18-crown-6 [J. Chem. Soc. 39 (1946) and J. Org. Chem. 21, 1547 (1956)] in 750 ml. of THF is added over a period of 40 min. After 10 min. longer, the mixture is treated with 130 ml. of 1M hydrochloric acid and poured into cold brine, then extracted with ether. The organic layer is separated, washed with aqueous sodium thiosulfate, aqueous sodium bicarbonate, and brine, dried with sodium sulfate, and evaporated under reduced pressure to give the title compound (88 g. of product). The above product is chromatographed over 5 kg. of silica gel wet-packed with Skellysolve B, eluting with 40 l. of 2.5% ethyl acetate in Skellysolve B, 8 l. of 3.75% ethyl acetate in Skellysolve B, 64 l. of 5% ethyl acetate in Skellysolve B, and 24 l. of 10% ethyl acetate in Skellysolve B. The last 9 l. of 5% ethyl acetate and the 24 l. of 10% ethyl acetate in Skellysolve B eluates are evaporated to give 11.8 g. of the title compound; infrared absorption at 3000, 1740, 1605, 1495, 1200, 1160 (broad) and 705 cm$^{-1}$.; NMR peaks at 7.17 (singlet), 4.75–4.60 (complex multiplet) and 3.62 (singlet) $\delta$.

B. A solution of 7.95 g. of potassium t-butoxide in 800 ml. of tetrahydrofuran is prepared, and 16.0 g. of endo-6-(cis-4-phenyl-1-butenyl)-bicyclo [3.1.0]hexan-3-one (Example 1) is added at about 25° C. This solution is stirred for 2 min., then is added to a solution of 28.7 g. of methyl $\omega$-iodoheptanoate in 400 ml. of THF at 25° C. and is stirred for 40 min. under a nitrogen atmosphere. Water (200 ml.) and 80 ml. of 5% hydrochloric acid are added. The mixture is concentrated under reduced pressure, heating with a water bath at 70° C., until the THF is removed. The aqueous residue is extracted with ether. The ether extract is washed with water, then with brine, and dried over sodium sulfate, then evaporated to leave a residue containing the title compound. This product is dissolved in methylene chloride and chromatographed over 2 kg. of silica gel wet-packed with 2% methanol in methylene chloride, and cleared with 800 ml. of methylene chloride. The column is eluted with 4.1 l. of methylene chloride, 4 l. of 1% methanol in methylene chloride, 4 l. of 2% methanol in methylene chloride, and 2 l. of 4% methanol in methylene chloride. The 4% methanol in methylene chloride and all but the first 200 ml. of the 2% methanol in methylene chloride eluates are evaporated to give 5.67 g. of the title compound having the same properties as that obtained in A above.

EXAMPLE 4 dl-Methyl
7-[endo-6-(cis-5-phenyl-1-pentenyl)-3-oxobicyclo[3.1.0]hex-2$\alpha$-yl]-heptanoate. (Formula XXXVI:

Z is -(CH$_2$)$_3$-C$_6$H$_5$;

R$_2$, R$_3$, and R$_4$ are hydrogen; R$_{10}$ is methyl; Z is -(CH$_2$)$_5$-; and ~ is endo and alpha)

Following the procedure of Example 3A, but using endo-6-(cis-5-phenyl-1-pentenyl)bicyclo[3.1.0]hexan-3-one Example 2 instead of endo-6-(cis-4-phenyl-1-butenyl)-bicyclo[3.1.0]-hexan-3-one, there is obtained the corresponding title compound; NMR peaks at 7.39 (singlet), 6.0-4.7 (two broad complex patterns) and 3.72 (singlet) $\delta$.

Following the procedures of Example 3, but using in place of the bicyclo[3.1.0]hexane reactant, each of endo and exo forms of the various Formula-XXVII bicyclo[3.1.0]hexane reactants whose preparation is described following Example 2, for example, Formula-XXVII bicyclo compounds wherein R$_3$ and/or R$_4$ are hydrogen, methyl, ethyl, propyl, or butyl, C$_t$H$_{2t}$ is a valence bond, methylene, ethylene, propylene, butylene, hexylene, octylene, or decalene, and s is zero, there are obtained alpha and beta exo and endo compounds corresponding to the products of Example 3 wherein R$_2$ is hydrogen, R$_{10}$ is methyl, and Z is -(CH$_2$)$_6$-. Accordingly, using the Formula-XXVII bicyclo compound wherein -C$_t$H$_{2t}$ represents alkylene substituted with one or 2 fluoro, for example the bicyclo compound prepared by the procedures of Preparation 1 and Example 1 from (2-bromo-1-fluoroethyl)benzene, (5-bromo-4-fluoropentyl)benzene, or (6-bromo-5,5-difluorohexyl)benzene there are obtained compounds corresponding to the products of Example 3 wherein -C$_t$H$_{2t}$- represents alkylene substituted with one or 2 fluoro. Accordingly, using the Formula-XXVII bicyclo compounds wherein (T)$_s$ on the phenyl ring is alkyl of one to 4 carbon atoms, inclusive, fluoro, chloro, trifluoromethyl, or OR$_9$ wherein R$_9$ is hydrogen, alkyl of one to 4 carbon atoms, inclusive, or tetrahydropyranyl, and s is one, 2, or 3, for example Formula-XXVII bicyclo compounds wherein (T)$_s$ is 2-methyl, 2,4,6-trimethyl, 2-chloro-3-trifluromethyl, or 3,4-dimethoxy, there are obtained compounds corresponding to the products of Example 3.

Also following the procedure of Example 3, but using in place of the halo alkylation agent of that example, namely methyl $\omega$-iodoheptanoate, others of the formula Hal-CHR$_2$-Z-COOR$_{10}$, there are obtained alpha and beta, exo and endo compounds corresponding to the products of Example 3 with -CHR$_2$-Z-COOR$_{10}$ in place of the -CH$_2$-(CH$_2$)$_5$-COOCH$_3$ moiety. Accordingly, usng the alkylation agent wherein Z is (a) alkylene of 3 to 12 carbon atoms, inclusive, substituted with zero, one, 2, 3, or 4 fluoro, with 3 to 7 carbon atoms, inclusive, between -CHR$_2$- and -COOR$_{10}$, or (b) -C $\equiv$ C-A- wherein A is alkylene of one to 10 carbon atoms, inclusive, substituted with zero, one 2, 3, or 4 fluoro, with one to 5 carbon atoms, inclusive, between $\equiv$ C- and COOR$_{10}$, with the proviso that when 3 or 4 fluoro are present, they are all substituents of the carbon atoms alpha and beta to -COOR$_{10}$, there are obtained compounds corresponding to the products of Example 3 with -CHR$_2$-Z-COOR$_{10}$ in place of the -CH$_2$-(CH$_2$)$_5$-COOCH$_3$ moiety. For example, using as alkylating agents in the Example 3 procedure;

I(CH$_2$)$_5$CHFCOOCH$_2$CCl$_3$, I(CH$_2$)$_6$COOCH$_3$,

BrCH(C$_2$H$_5$)(CH$_2$)$_5$COOCH$_2$-C$_6$H$_5$, I CH(C$_4$H$_9$)(CH$_2$)$_7$COOCH$_2$CCl$_3$,

-continued

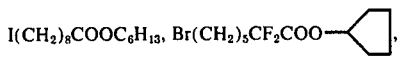

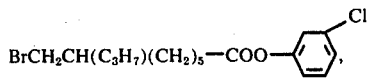

I CH(CH₃)(CH₂)₄CH(CH₃)CF₂CF₂COOC₂H₅, I CH₂C≡C(CH₂)₃COOCH₃,

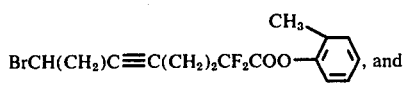, and

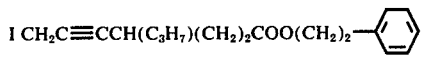

there are obtained exo and endo, alpha and beta alkylated bicyclo[3.1.0] hexanes each having a carboxylate-terminated side chain corresponding to one of the above specific alkylating agents.

In the same manner but using, according to Example 3, other esters of the Example 3 alkylation agent and of the other above-mentioned alkylation agents within the scope of $R_{10}$ as above-defined, e.g., the methyl, isopropyl, tert-butyl, octyl, cyclohexyl, benzyl, phenyl, and trichloroethyl esters, there are obtained the corresponding esters of the alpha and beta bicyclo[3.1.0-]hexane alkylation products.

Also following the procedure of Example 3, but using in combination each of the alternative alkylating agents within the scope of Hal-CHR₂-Z-COOR₁₀, including the specific examples above-mentioned, and each of the Formula-XXVII alternative bicyclo[3.1.0]hexane reactants produced following Example 2, there are obtained Formula-XXXVI exo and endo, alpha and beta compounds corresponding to the products of Example 3 but different therefrom with respect to both the carboxylate-terminated side chain and the

terminated side chain. With excess base and a longer reaction time, these alternative products contain substantial amounts of the correspondng beta isomer which is separated from the alpha isomer by method described herein, e.g., silica gel chromatography.

EXAMPLE 5 dl-Ethyl 7-[Endo-6-(1,2-dihydroxy-4-phenylbutyl)-3-oxobicyclo[1.3.0]hex-2α-yl]-cis-5-heptenoate Acetonide (Formula XXX: R₂, R₃, and R₄ are hydrogen, R₁₀ is ethyl, R₁₁ and R₁₂ are methyl,

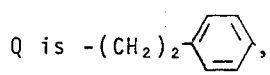

V is -CH = CH(CH₂)₃-, and ~ is endo and alpha)

Refer to Charts C and E. Glycol XXVIII is prepared prior to forming ketal XXIX.

A solution of potassium clorate (10.0 g.) and osmium tetroxide (0.65 g.) in 250 ml. of water is added with stirring to a solution of the Formula-XXVII bicyclo olefin endo-6-(cis-4-phenyl-1-butenyl)bicyclo[3.1.0-]hexan-3-one (Example 1, 10g.). The mixture is stirred vigorously for 5 hours at 50° C. Then the cooled mixture is concentrated under reduced pressure. The residue is extracted repeatedly with dichloromethane, and the combined extracts are dried and evaporated to a residue. This residue is chromatographed on silica gel, and eluted successively with a gradient of 10–50% ethyl acetate in a mixture of isomeric hexanes (Skellysolve B). Fractions containing the dihydroxy compound are combined and evaporated to dryness to give glycol XXVIII, endo-6-(1,2-dihydroxy-4-phenylbutyl)-bicyclo[3.1.0]hexan-3-one.

A solution of glycol XXVIII above (about 8.0 g.) and 700 mg. of potassium bisulfate in 140 ml. of acetone is stirred at 25° C. for 64 hrs. Then, sodium carbonate monohydrate (710 mg.) is added, and the mixture is stirred 10 minutes. The acetone is evaporated at reduced pressure, and water is added. The aqueous solution is extracted repeatedly with dichloromethane, and the extracts are combined, washed with water, dried and evaporated to a residue. This residue is chromatographed on silica gel and eluted with a gradient of 10–15% ethyl acetate in Skellysolve B. The 15% ethyl acetate eluates are evaporated to give ketal XXIX, endo-6-(1,2-dihydroxy-4-phenylbutyl)-bicyclo[3.1.0]-hexan-3-one acetonide.

Following the alkylation procedure of Example 3, but using ketal XXIX above instead of the endo-6-(cis-4-phenyl-1-butenyl)-bicyclo[3.1.0]hexan-3-one compound of that example, ketal XXIX is alkylated with ethyl cis-7-iodo-5-heptenoate (Preparation 5) to give the title compound.

EXAMPLE 6 dl-Ethyl 7-[endo-6-(1,2-dihydroxy-3-phenylpropyl)-3-oxobicyclo[3.1.0]hex-2α-yl]-cis-5-heptenoate Acetonide (Formula XXX: R₂, R₃, and R₄ are hydrogen, R₁₀ is ethyl, R₁₁ and R₁₂ are methyl,

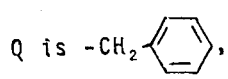

V is -CH=CH(CH₂)₃-, and ~ is endo and alpha)

Refer to Charts C and E. Following the procedure of Example 5, but replacing that bicyclo olefin XXVII with bicyclo olefin XXVII obtained following Example 1 from the quaternary phosphonium halide of (2-bromoethyl)benzene, namely endo-6-(cis-3-phenyl-1-propenyl)-bicyclo[3.1.0]hexan-3-one, there is obtained the corresponding glycol XXVIII and then ketal XXIX. Thereafter alkylation with ethyl cis-7-iodo-5-heptenoate (Preparation 5) yields the title compound.

EXAMPLE 7 dl-Ethyl 7-[endo-6-(1,2-dihydroxy-3,3-dimethyl-4-phenylbutyl)-3-oxobicyclo[3.1.0]hex-2β-yl]-cis-5-heptenoate Acetonide (Formula XXX: $R_2$, $R_3$, and $R_4$ are hydrogen, $R_{10}$ is ethyl, $R_{11}$ and $R_{12}$ are methyl, Q is

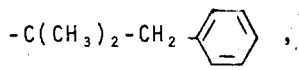

V is -CH=CH(CH$_2$)$_3$-, and ~ is endo and alpha)

Refer to Charts C and E. Following the procedure of Example 5, but replacing that bicyclo olefin XXVII with bicyclo olefin XXVII obtained following Example 1 from the quaternary phosphonium halide of Preparation 4, namely endo-6-(cis-3,3-dimethyl-4-phenyl-1-butenyl)-bicyclo[3.1.0]hexan-3-one, there is obtained the corresponding glycol XXVIII and then ketal XXIX. Thereafter alkylation with ethyl cis-7-iodo-5-heptenoate (Prepartion 5) yields the title compound.

EXAMPLE 8 dl-2,2,2-Trichloroethyl-9-[endo-6-(1,2-dihydroxy-4-phenylbutyl)-3-oxobicyclo[3.1.0]-hex-2α-yl]-cis-7-nonenoate Acetonide (Formula XXX: $R_2$, $R_3$, and $R_4$ are hydrogen, $R_{10}$ is CCl$_3$CH$_2$-, $R_{11}$ and $R_{12}$ are methyl, Q is

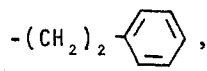

V is -CH=CH-(CH$_2$)$_5$-, and ~ is endo and alpha)

Refer to Chart C. Following the procedure of Example 5, but replacing the alkylation agent of that example with 2,2,2-trichloroethyl cis-9-bromo-7-nonenoate (Preparation 6), that ketal XXIX, namely endo-6-(1,2-dihydroxy-4-phenyl-butyl)-bicyclo[3.1.0]hexan-3-one acetonide, is alkylated to give the title compound.

Following the procedure of Example 5, but replacing that bicyclo olefin XXVII with the Formula-XXVII compound of Example 2, namely endo-6-(cis-5-phenyl-1-pentenyl)bicyclo [3.1.0]hexan-3-one, there is obtained the corresponding Formula-XXX alkylated ketal wherein Q is

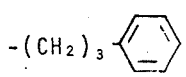

Also followng the procedure of Example 5, but using the bicyclo olefin XXVII compounds disclosed following Examples 1 and 2, there are obtained the corresponding Formula-XXIX bicyclo ketals and Formula-XXX alkylated ketals. For example, the 3-fluoro-3-phenyl-1-propenyl Formula-XXVII compound yields ethyl 7-[endo-6-(1,2-dihydroxy-3-fluoro-3-phenylpropyl)-3-oxobicyclo[3.1.0]hex-2α-yl-cis-5-heptenoate. Depending upon the reactants and the conditions employed, as disclosed hereinabove, there are obtained products in the alpha or beta, exo or endo configuration.

Also following the procedure of Example 5, but replacing ethyl cis-7-iodo-5-heptenoate as an alkylation agent with ethyl 3-fluoro-7-iodo-heptenoate, ethyl trans-7-iodo-5-heptenoate, and ethyl 7-iodo-5-heptynoate, there are obtained alpha and beta, exo and endo compounds corresponding to the product of Example 5 with -(CH$_2$)$_4$-CHF-CH$_2$COOEt, trans-CH$_2$CH=CH(CH$_2$)$_3$COOEt, and -CH$_2$C≡C(CH$_2$)$_3$COOEt, respectively, wherein Et is ethyl, in place of the cis-CH$_2$CH=CH(CH$_2$)$_3$COOEt moiety of the Example 5 product. In the same manner, but using, according to Example 5, other esters of the Prepn.-5 alkylating agent and of the other above-mentioned alkylating agents within the scope of $R_{10}$ as above-defined, e.g., the methyl, isopropyl, tert-butyl, octyl, β,β,β-trichloroethyl, cyclohexyl, benzyl, and phenyl esters, there are obtained corresponding esters of these alpha and beta, exo and endo Formula-XXX bicyclo-[3.1.0]hexane cyclic ketal alkylation products.

Also following the procedure of Example 5, but using in combination each of the above-described alternative Formula-XXIX bicyclo[3.1.0]hexane cyclic ketal reactants and each of the above-described omega-halo alkylation reactants within the scope of

there are obtained Formula-XXX compounds corresponding to the product of Example 5, but different therefrom with respect to both the carboxylate-terminated side chain and the side chain attached to the cyclopropane ring of the product, and in their respective alpha or beta and exo or endo configuration.

EXAMPLE 9

Resolution of Ethyl 7-[Endo-6-(1,2-dihydroxy-4-phenylbutyl)-3-oxobicyclo[3.2.0]hex-2α-yl]cis-5-heptenoate Acetonide The title ketal XXX is resolved as its optical isomers following the method of Corey et al., J. Am. Chem. Soc. 84, 2938 (1962). This keto compound is contacted with the equivalent amount of L(+)-2,3-butanedithiol in the presence of p-toluenesulfonic acid in benzene, and the mixture heated under reflux for about 20 hrs. with a Dean and Stark trap. The resulting mixture of diastereomeric ketals is resolved on a preparative chromatographic column. Therafter the separate ketals are hydrolyzed with hydrochloric acid (1:1) in THF to the corresponding pair of optically active glycols represented by Formula XXXI and its mirror image.

Following the procedures of Example 9, the Formula-XXX ketals of Examples 6, 7, and 8 and following Example 8 are resolved into their respective optical isomers in the form of diastereomeric ketals and thereafter hydrolyzed to the corresponding glycols. For example, ketal XXX of Example 6 yields the pair of optically active glycols represented by Formula XXXI and its mirror image wherein $R_2$, $R_3$, and $R_4$ are hydrogen, $R_{10}$ is ethyl,

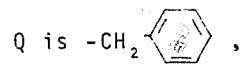

and V is -CH=CH(CH$_2$)$_3$-. These glycols are useful as intermediates for preparing 16-phenyl-17,18,19,20-tetranor-PGE$_2$ and its enantiomer of Example 28 below. Similarly, ketal XXX of Example 7 when resolved and hydrolyzed yields the pair of optically active glycols useful as intermediates for preparing 16,16dimethyl-17-phenyl-18,19,20-trinor-PGE$_2$ and its enantiomer of Example 30 below. Likewise, ketal XXX of Example 8 yields intermediates for preparing 1a, 1b-dihomo-17-phenyl-18,19,20-trinor-PGE$_2$ and its enantiomer of Example 29 below.

EXAMPLE 10 dl-17-Phenyl-18,19,20-trinor-PGE$_1$ Methyl Ester
(Formula XI: D is -(CH$_2$)$_5$-; R$_1$ is methyl; R$_2$, R$_3$, and R$_4$ are hydrogen; s is zero; C$_t$H$_{2t}$ is -(CH$_2$)$_2$-; -OH on -CR$_3$OH- is in alpha configuration; and ~ is alpha) and dl-15$\beta$-17-Phenyl-18,19,20-trinor PGE$_1$ Methyl Ester (wherein -OH on -CR$_3$OH- is in beta configuration).

Refer to Chart D.

A. Glycol XXXVII: dl-Methyl 7-[endo-6-(1,2-dihydroxy-4-phenylbutyl)-3-oxobicyclo[3.1.0]hex-2$\alpha$-yl]heptanoate.- A solution of Formula-XXXVI methyl 7-[endo-6-(cis-4-phenyl-1-butenyl)-2-oxobicyclo[3.1.0]hex-2$\alpha$-yl]heptanoate (Example 3, 11.8 g.) in 160 ml. of THF is stirred at 50° C. under nitrogen and 1.0 g. of osmium tetroxide is added followed by a solution of 6.5 g. of potassium chlorate in 75 ml. of water. Stirring is continued at 50° C. for 3 hrs.; then the THF is removed by evaporation under reduced pressure and the residue is extracted with dichloromethane. The organic layer is washed with water, dried over sodium sulfate, and concentrated to give 14.2 g. of glycols. This product is chromatographed over 2 kg. of silica gel wet-packed with 15% ethyl acetate in Skellysolve B, eluting successively with 8 l. of 15%, 12 l. of 25%, 16 l. of 35% and 8 l. of 60% ethyl acetate in Skellysolve B followed by gradient elution between 4 l. of 60% and 4 l. of 80% ethyl acetate in Skellysolve B, and then 8 l. of 80% ethyl acetate in Skellysolve B, taking 600 ml. fractions. The 45%, the 60%, the 60-80%, and the first 3 l. of the 80% ethyl acetate in Skellysolve B eluates are concentrated to give 7.1 g. of the racemic glycol XXXVII product as a mixture of isomeric glycols.

B. Bismesylate XXXVIII: dl-methyl 7-[endo-6-(1,2-dihydroxy-4-phenylbutyl)-3-oxobicyclo[3.1.0]hex-2$\alpha$-yl]-heptanoate bismethanesulfonate.- The above glycol mixture (7.1 g.) is dissolved in 90 ml. of pyridine and stirred at 0° C. under nitrogen while 8.5 ml. of methanesulfonyl chloride is added over a period of 15 min. The mixture is stirred at 0° C. for 2.5 hrs., then cooled to −15° C. and to it is slowly added 10 ml. of ice and water. After 5 min. additional stirring at −5° to 0° C., the mixture is poured into 500 ml. of ice and water. Cold 1:3 dichloromethane-ether (200 ml.) is added, followed by 360 ml. of cold 3 M hydrochloric acid, and the mixture is extracted rapidly with dichloromethane-ether. The organic extracts are washed with 2% sulfuric acid, water, aqueous sodium bicarbonate, and brine, then dried over sodium sulfate and concentrated to give 10.5 g. of the racemic bismesylate XXXVIII product; infrared absorption at 2990, 1740, 1610, 1495, 1350, 1180 and 703 cm$^{-1}$.

C. Title compounds.- This bismesylate of the mixed glycols (10.5 g.) is dissolved in 400 ml. of 2:1 acetone-water and left standing about 18 hrs. at 25° C., then is diluted with 400 ml. of water and the acetone is removed by evaporation under reduced pressure. The aqueous residue is extracted with ethyl acetate and the extracts are washed with aqueous sodium bicarbonate and brine, then dried over sodium sulfate and concentrated to an oil (6.5 g.). The oil is chromatographed over 1.6 kg. of silica gel wet-packed with 30% ethyl acetate in Skellysolve B, eluting with 8 l. of 30%, 4 l. of 40%, 13 l. of 60%, and 16 l. of 80% ethyl acetate in Skellysolve B, 10 l. of ethyl acetate, then gradient eluted with 5 l. of ethyl acetate, and 5 l. of 5% methanol in ethyl acetate, collecting 500 ml. fractions. The 80% ethyl acetate in Skellysolve B fractions are numbered 1–32, the ethyl acetate fractions are numbered 33–49 and the gradient elution fractions are numbered 50–66. Fractions 21–32 are concentrated to give 1.278 g. of dl-15$\beta$- 17-phenyl-18, 19, 20-trinor-PGE$_1$ methyl ester; infrared absorption at 3400, 1735, 1600, 1495, 1330, 1250, 1200, 1170, 1100, 1070, 1030, 970, 750, 725 and 700 cm$^{-1}$.; NMR peaks at 7.24 (singlet), 5.64–5.83 (multiplet), 3.8–4.6 (complex multiplet) and 3.65 (singlet) $\delta$; mass spectral peaks at 402 and 384.

Fractions 43–54 are evaporated to give 1.111 g. of dl-17-phenyl-18, 19, 20-trinor-PGE$_1$ methyl ester which is recrystallized from ether-Skellysolve B to give an analytical sample, m.p. 67°–69° C.; infrared absorption at 3370, 1740, 1710, 1600, 1495, 1330, 1310, 1285, 1245, 1220, 1175, 1155, 1095, 1070, 1000, 975, 720 and 700 cm$^{-1}$.; NMR peaks at 7.24 (singlet), 5.5–5.8 (complex multiplet), 3.64 (singlet), 3.85–4.30 and 3.23–3.45 (broad unresolved multiplets) $\delta$; mass spectral peaks at 402 and 384.

EXAMPLE 11 dl-18-Phenyl-19, 20-dinor-PGE$_1$ Methyl Ester
(Formula XI: D is -(CH$_2$)$_5$-; R$_1$ is methyl; R$_2$, R$_3$, and R$_4$ are hydrogen; s is zero; -OH on -CR$_3$OH- is alpha configuration; and ~ is alpha) and
dl-15$\beta$-18-Phenyl-19, 20-dinor-PGE$_1$ Methyl Ester (wherein -OH on -CR$_3$OH- is in beta configuration).

Refer to Chart D and Example 10. Following the procedures of Example 10, but replacing the alkylated olefin XXXVI of that example with methyl 7-[endo-6-(cis-5-phenyl-1-pentenyl)-3-oxobicyclo[3.1.0]hex-2$\alpha$-yl]heptanoate (Example 4, 16.8 g.) there is obtained the corresponding racemic bismesylate, 17 g.: infrared absorption at 3000, 1740, 1500, 1350, 1175, 910, and 704 cm$^{-1}$.

The above bismesylate (17 g.) is dissolved in 500 ml. of 2:1 acetone-water and left standing under nitrogen about 18 hrs. at 25° C. The acetone is removed by evaporation under reduced pressure and the residue is diluted with water and extracted with several portions of dichloromethane. The extracts are combined and washed with aqueous sodium bicarbonate and brine, dried over sodium sulfate, and concentrated under reduced pressure to give a residue (11.9 g.). This residue is chromatographed over 2 kg. of silica gel wet-packed with Skelly-solve B, eluting successively with 10 l. of 40%, 10 l. of 60%, and 20 l. of 80% ethyl acetate in Skellysolve B, 10 l. of ethyl acetate and 10 l. of 5% methanol in ethyl acetate, taking 680 ml. fractions. Fractions 27–32 are concentrated to give 1.4 g. of dl-15β-18-phenyl-19,20-dinor-PGE₁ methyl ester; infrared absorption at 3240, 1735, 1600, 1495, 1355, 1325, 1250, 1200, 1165, 1095, 1075, 1025, 970, 750 and 700 cm⁻¹.; NMR peaks at 7.21 (singlet), 5.66 (pseudo doublet), 4.5–3.8 (multiplet), 3.22 (broad singlet) and 3.53 (singlet) δ; mass spectral peaks at 416, 398, 380 and 297.

Fractions 50–61 are evaporated to give 1.38 g. of dl–18-phenyl-19,20-dinor PGE₁ methyl ester, which on two recrystallizations from ether-hexane gives an analytical sample, m.p. 55°–56° C., infrared absorption at 3300, 1735, 1600, 1495, 1325, 1310, 1290, 1275, 1255, 1225, 1155, 1105, 1065, 980, 750, 725 and 700 cm⁻¹.; NMR absorption at 7.21 (singlet), 5.57 (triplet), 4.43–3.6 (broad pattern), and 3.65 (singlet) δ; mass spectral peaks at 398, 380 and 349.

Following the procedure of Example 10A, but using the hex-2β-yl isomer in place of the hex-2α-yl isomer of the bicyclo reactant, methyl 7-[endo-6-(1,2-dihydroxy-4-phenylbutyl)-3-oxobicyclo[3.1.0]hex-2β-yl]heptanoate is obtained.

Also following the procedure of Example 10A, each of the specific Formula-XXXVI exo and endo, alpha and beta saturated and acetylenic bicylclo[3.1.0]hexane olefinic esters defined follownг Examples 3 and 4 is oxidized to mixtures of the corresponding isomeric dihydroxy compounds encompassed by Formula XXXVII above and its mirror image. For example, β,β,β-trichloroethyl 2-fluoro-7-[endo-6-(3-fluoro-3-phenyl-1-propenyl)3-oxo-bicyclo[3.1.0]hex-2α-yl]-heptanoate yields β,β,β-trichloroethyl 2-fluoro-7[endo-6-(3-fluoro-1,2-dihydroxy-3-phenylpropyl)3-oxo-bicyclo[3.1.0]-hex-2α-yl]heptanoate in its isomeric forms, as represented by the following formulas:

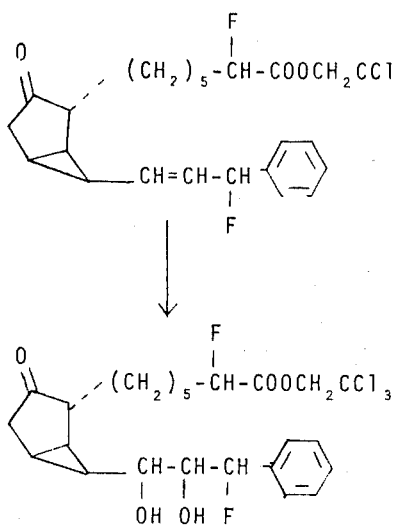

Likewise, 2-methylphenyl 2,2-difluoro-7-{endo-6-[1,2-dimethyl-4-(4-methoxyphenyl)-1-butenyl]-3-oxo-bicyclo[3.1.0]-hex-2β-yl}-7-methyl-5-heptynoate yields 2-methylphenyl 2,2-difluoro-7-{endo-6-[1,2-dihydroxy-1,2-dimethyl-4-(4-methoxyphenyl)butyl]-3-oxobicyclo[3.1.0]hex-2β-yl}-7-methyl-5-heptynoate, in its isomeric forms, as represented by the following formulas:

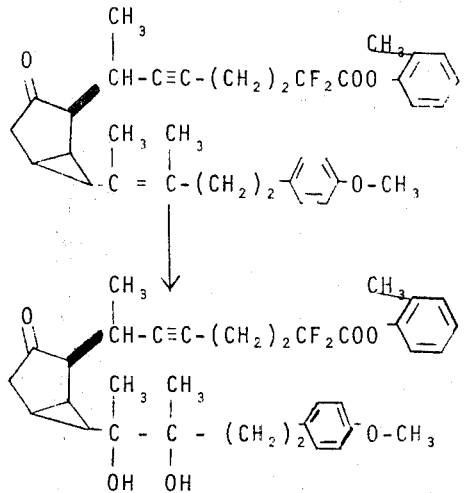

The various isomers are separated by methods described herein, e.g. silica gel chromatography.

Following the procedure of Example 10B, each of the above Formula-XXXVII dihydroxy compounds following Example 11 is transformed to the corresponding Formula-XXXVIII bis-mesyl ester. For example, β,β,β-trichloroethyl 2-fluoro-7-[endo-6-(3-fluoro-1,2-dihydroxy-3-phenylpropyl)-3-oxo-bicyclo[3.1.0]-hex-2α-yl]heptanoate yields β,β,β-trichloroethyl 2-fluoro-7-[endo-6-(3-fluoro-1,2-dimesyloxy-3-phenylpropyl)-3-oxo-bicyclo[3.1.0]hex-2α-yl]heptanoate.

Also following the procedure of Example 10B, but replacing methanesulfonyl chloride with an alkanesulfonyl chloride or bromide, or with an alkanesulfonic acid anhydride wherein the alkane moiety contains 2 to 5 carbon atoms, inclusive, there is obtained from each dihydroxy compound the corresponding bis-sulfonic acid esters encompassed by Formula XXXVIII above.

In each of the above transformations the monosulfonic acid ester is also obtained as a byproduct, which is reacted with additional alkanesulfonyl halide or alkanesulfonic acid anhydride to give the corresponding bis-sulfonic acid ester.

Following the procedure of Example 10C, each of the above bis-mesyl esters following Example 11 is transformed to the corresponding phenyl-substituted prostaglandin-like E ester within the scope of Formula XXXIX, i.e. wherein Z is -D- as in Formula XI for PGE₁-type compounds or where Z is -C ≡ C-A- as in Formula XIII for 5,6-didehydro-PGE₂-type compounds except that R₁ is not hydrogen. Likewise, the 15-beta epimers and the compounds represented by the mirror images of those formulas are prepared.

For example, β,β,β-trichloroethyl 2-fluoro-7-[endo-6-(3-fluoro-1,2-dimesyloxy-3-phenylpropyl)-3-oxo-bicyclo[3.1.0]hex-2α-yl]heptanoate yields dl-2,16-difluoro-16-phenyl-17,18,19,20-tetranor-PGE₁ β,β,β-trichloroethyl ester, as represented by the following formulas:

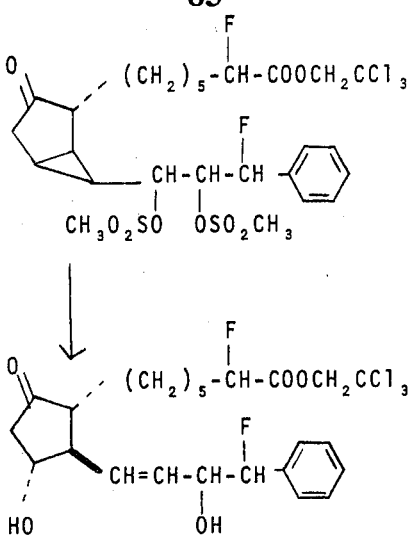

Likewise, 2-methylphenyl 2,2-difluoro-7- endo-6-[1,2-dimesyloxy-1,2-dimethyl-4-(4-methoxyphenyl)-1-butyl]-3-oxobicyclo[3.1.0]hex-2β-yl -7-methyl-5-heptynoate yields 2,2-difluoro-14,15-dimethyl 5,6-didehydro-17-(4-methoxyphenyl)-18,19,20-trinor-PGE$_2$ 2-methylphenyl ester, as represented by the following formulas:

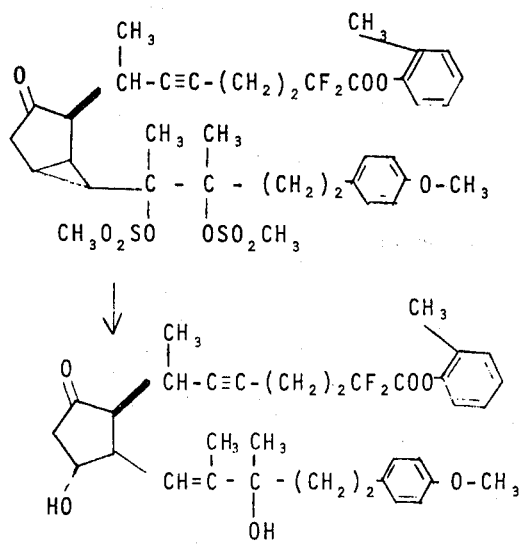

Following the procedure of Example 10, but using the β,β,β-trichloroethyl ester of the alkylated olefin XXXVI instead of the methyl ester of that example, there is obtained the corresponding phenyl-substituted PGE$_1$ ester, i.e. the β,β,β-trichloroethyl ester instead of the methyl ester of Example 10, in its various isomeric forms

EXAMPLE 12 dl-17-Phenyl-18,19,20-trinor-PGF$_{1\alpha}$ Methyl Ester and dl-17-phenyl-18,19,20-trinor-PGF$_{1\beta}$ Methyl Ester (Formula XV: D is -(CH$_2$)$_5$-; R$_1$ is methyl; R$_2$, R$_3$, and R$_4$ are hydrogen; $s$ is zero; C$_t$H$_{2t}$ is -(CH$_2$)$_2$-; -OH on -CR$_3$OH- is in alpha configuration; and ~ is alpha or beta)

Refer to Chart A. A solution of 600 mg. of sodium borohydride in 10 ml. of ice-cold methanol is added to a solution of 1.34 g. of dl-17-phenyl-18,19,20-trinor-PGE$_1$ methyl ester (Example 10) in 60 ml. of methanol and the reaction mixture is stirred at 0° C. for 30 min. Acetone (10 ml.) is added and the solution is made slightly acid with dilute acetic acid in methanol. The mixture is concentrated under reduced pressure and the residue is taken up in dichloromethane. The solution is washed with brine, dried over sodium sulfate, and evaporated under reduced pressure to give a residue which is chromatographed over 250 g. of silica gel wet-packed in 8% methanol in dichloromethane and rinsed with 300 ml. of dichloromethane, eluting with 250 ml. of 5%, 500 ml. of 6%, 1000 ml. of 8% and 250 ml. of 10% methanol in dichloromethane, taking 25 ml. fractions. Eluate fractions 44–53 are combined and concentrated to give 420 mg. of the PGF$_{1\alpha}$ -type title compound: NMR peaks at 7.15, 5.35–5.54 (broad peak), 3.77–4.17, 3.68 (singlet), 3.02–3.37 and 1.32 δ.

Eluate fractions 58–75 are concentrated to give 572 mg. of the PGF$_{1\beta}$ -type title compound: NMR peaks at 7.15, 5.35–5.54 (broad peak), 3.77–4.17, 3.68 (singlet), 3.33–3.53 (broad peak) and 1.32 δ.

EXAMPLE 13 dl-15β-17-Phenyl-18,19,20-trinor-PGF$_{1\alpha}$ Methyl Ester and dl-15β-17-phenyl-18,19,20-trinor-PGF$_{1\beta}$ Methyl Ester (Formula XV: D is -(CH$_2$)$_5$-; R$_1$ is methyl; R$_2$, R$_3$, and R$_4$ are hydrogen; s is zero; C$_t$H$_{2t}$ is -(CH$_2$)$_2$-; -OH on -CR$_3$OH- is in beta configuration; and ~ is alpha or beta)

Following the procedure of Example 12, dl-15β-17-phenyl-18,19,20-trinor-PGE$_1$ methyl ester (Example 10) is reduced to a mixture of the title compounds. The mixture is concentrated under reduced pressure and the residue is taken up in dichloromethane. The solution is washed with brine, dried over sodium sulfate and evaporated under reduced pressure to give a residue which is chromatographed over silica gel wet-packed in 8% methanol in methylene chloride and rinsed with 300 ml. of methylene chloride, eluting with 500 ml. of 2%, 500 ml. of 4%, 500 ml. of 6%, 1000 ml. of 8% and 250 ml. of 10% methanol in methylene chloride, taking 25 ml. eluate fractions. Fractions 71–79 are concentrated to give 350 mg. of the PGF$_{1\alpha}$ -type title compound: NMR peaks at 7.15, 5.42–5.62 (split multiplet), 3.77–4.17, 3.68 (singlet), 2.70–2.97 and 1.32 δ.

Fractions 86–106 are concentrated to give 640 mg. of the PGF$_{1\beta}$ -type title compound: NMR peaks at 7.15, 5.42–5.62 (split multiplet), 3.77–4.17, 3.68 (singlet), 2.47–3.05 and 1.32 δ.

EXAMPLE 14 dl-17-Phenyl-18,19,20-trinor-PGF$_{1\alpha}$ and dl-17-phenyl-18,19,20-trinor-PGF$_{1\beta}$ (Formula XV: D is -(CH$_2$)$_5$-; R$_1$, R$_2$, R$_3$, and R$_4$ are hydrogen; s is zero; C$_t$H$_{2t}$ is -(CH$_2$)$_2$-; -OH on -CR$_3$OH- is in alpha configuration and ~ is alpha or beta)

A solution of the methyl ester (Example 12) of the appropriate PGF$_1$-type ester (0.14 g.) in a mixture of 4.5 ml. of methanol and 1.5 ml. of water is cooled to 5° C. and 0.6 ml. of 45% aqueous potassium hydroxide is added. The mixture is left standing 3.5 hrs. at 25° C., then is diluted with 75 ml. of water and extracted once with ethyl acetate to remove any neutral material. The aqueous layer is separated, made acid with dilute hydrochloric acid and extracted 4 times with ethyl acetate. The extracts are combined and washed 3 times with water, once with brine, dried over sodium sulfate, and evaporated to give the title compound. dl-17-Phenyl-18,19,20-trinor-PGF$_{1\alpha}$ is obtained as crystals, m.p. 110°–111°; infrared absorption at 3290, 2700, 1705, 1600, 1585, 1500, 1325, 1260, 1215, 1035, 1005, 995, 970, 930, and 700 cm$^{-1}$.; mass spectral peaks at 372, 354, and 336. Similarly, dl-17-phenyl-18,19,20-trinor-PGF$_{1\beta}$ is obtained as crystals, m.p. 108°–110°; infrared absorption at 3420, 3280, 2700, 1710, 1670(sh), 1600, 1585, 1495, 1325, 1230, 1210, 1190, 1095, 1040, 1000, 970, and 700 cm$^{-1}$.; mass spectral peaks at 372, 354 and 336.

EXAMPLE 15 dl-15$\beta$-17-Phenyl-18,19,20-trinor-PGF$_{1\alpha}$ and dl-15$\beta$-17-Phenyl-18,19,20-trinor-PGF$_{1\beta}$ (Formula XV: wherein -OH on -CR$_3$OH- is in beta configuration)

Following the procedure of Example 14, the 15$\beta$-PGF$_1$-type esters of Example 13 are saponified to the respective free acid compounds. dl-15$\beta$-17-Phenyl-18,19,20-trinor-PGF$_{1\alpha}$ is obtained as crystals, m.p. 65°–67°; infrared absorption at 3400–3240, 2760–2600, 1695, 1600, 1495, 1340, 1290, 1275, 1235, 1200, 1190, 1100, 1075, 1035, 990, 970, 945, 750, 725 and 700 cm$^{-1}$.; mass spectra peaks at 372, 354, 336 and 300.

Similarly, dl-15$\beta$-17-Phenyl-18,19,20-trinor-PGF$_{1\beta}$ is obtained as crystals, m.p. 75°–77° C.; infrared absorption at 3320, 2700, 1710, 1600, 1495, 1305, 1245, 1225, 1100, 1030, 1015, 970, 745 and 700 cm$^{-1}$.; mass spectra peaks at 372, 354, 336, and 300.

EXAMPLE 16 dl-18-Phenyl-19,20-dinor-PGF$_{1\alpha}$ and dl-18-phenyl-19,20-dinor-PGF$_{1\beta}$. (Formula XV: D is -(CH$_2$)$_5$-; R$_1$, R$_2$, R$_3$, and R$_4$ are hydrogen; s is zero; C$_t$H$_{2t}$ is -(CH$_2$)$_3$-; and ~ is alpha or beta)

Following the procedures of Example 12, but replacing the dl-17-phenyl-18,19,20-trinor-PGE$_{1\alpha}$ methyl ester of that example with dl-18-phenyl-19,20-dinor-PGE$_1$ methyl ester (Example 11), there are obtained the methyl esters of dl-18-phenyl-19,20-dinor-PGF$_{1\alpha}$ and dl-18-phenyl-19,20-dinor-PGF$_{1\beta}$.

Following the procedures of Example 14, the above methyl esters are saponified to yield the title compounds. dl-18-Phenyl-19,20-dinor-PGF$_{1\alpha}$ has m.p. 90°–92°; infrared absorption at 3300, 2700, 1700, 1600, 1580, 1495, 1345, 1300, 1285, 1250, 1225, 1075, 1030, 1005, 975, 940, 745 and 700 cm$^{-1}$.; mass spectral peaks (tetra trimethylsilyl derivative) at 677, 602 and 512. dl-18-Phenyl-19,20-dinor-PGF$_{1\beta}$ has m.p. 112°–113°; infrared absorption at 3320, 2700, 1710, 1600, 1495, 1235, 1290, 1275, 1240, 1200, 1095, 1045, 1025, 995, 975, 750 and 700 cm$^{-1}$.; mass spectral peaks (tetra trimethylsilyl derivative) at 677 and 602.

Following the procedures of Examples 12 and 14, but employing dl-15$\beta$-18-phenyl-19,20-dinor-PGE$_1$ methyl ester (Example 11), there are obtained the corresponding dl-15$\beta$-PGF$_{1\alpha}$ and PGF$_{1\beta}$ type compounds.

Following the procedures of Examples 12 and 14, the following PGF$_1$-type and 5,6-didehydro-PGF$_2$-type compounds within the scope of Formulas XV and XVII are prepared from the corresponding PGE$_1$-type and 5,6-didehydro-PGE$_2$-type esters defined above in and after Examples 10 and 11, in their optically active and racemic forms: 8$\beta$-17-phenyl-18,19,20-trinor-PGF$_{1\alpha}$ and -PGF$_{1\beta}$, 8$\beta$, 15$\beta$-17-phenyl-18,19,20-trinor-PGF$_{1\alpha}$ and -PGF$_{1\beta}$, 5,6-didehydro-17-phenyl-18,19,20-trinor-PGF$_{2\alpha}$ and -PGF$_{2\beta}$, 5,6-didehydro-15$\beta$-17-phenyl-18,19,20-trinor-PGF$_{2\alpha}$ and -PGF$_{2\beta}$, 5,6-didehydro-8$\beta$,-17-phenyl-18,19,20-trinor-PGF$_{2\alpha}$ and -PGF$_{2\beta}$, 5,6-didehydro-8$\beta$,-15$\beta$-17-phenyl-18,19,20-trinor-PGF$_{2\alpha}$, and -PGF$_{2\beta}$, and their corresponding 18-phenyl-19,20-dinor-PGF-type compounds.

Also following the procedures of Examples 12 and 14, each of the other phenyl-substituted PGE-type esters defined above after Examples 10 and 11 is transformed to the corresponding phenyl-substituted PGF$_\alpha$ -type and PGF$_\beta$ -type ester and free acid.

EXAMPLE 17 dl-15-Methyl-17-phenyl-18,19,20-trinor-PGF$_{1\alpha}$ Methyl Ester (Formula XV: D is -(CH$_2$)$_5$-; R$_1$ and R$_3$ are methyl; R$_2$ and R$_4$ are hydrogen; s is zero; C$_t$H$_{2t}$ is -(CH$_2$)$_2$-; and _ is alpha)

Refer to Chart F.

A. dl-15-Oxo-17-phenyl-18,19,20-trinor-PGF$_{1\alpha}$ (Formula XLIX).- A solution of dl-17-phenyl-18,19,20-trinor-PGF$_{1\alpha}$ (340 mg.) in dioxane (14.5 ml.) is warmed to 45° C. and purged with nitrogen, and to it is added 2,3-dichloro-5,6-dicyano-1,4-benzoquinone (0.22 g.). The mixture is stirred at 45°–50° C. overnight under nitrogen, then cooled and filtered on Celite filter aid. The organic solvents are removed by evaporation under reduced pressure and the residue is taken up in dichloromethane and washed with brine. The organic extracts are dried over sodium sulfate and concentrated to an oil. The product is chromatographed on 50 g. of acid-washed silica gel wet-packed with 8% methanol in dichloromethane, eluting with 150 ml. each of 2, 5, and 10%, and 75 ml. of 20% methanol in dichloromethane, taking 15 ml. eluate fractions. The 10% methanol fractions are numbered 21–30; the 20% methanol fractions are numbered 31–35. Fractions 24–32 are concentrated to give the 15-oxo compound (320 mg.), NMR peaks at 6.58, 6.45, 6.21, and 5.95, 4.34–3.70 (broad) $\delta$.

B. Trimethylsilyl derivative (Formula L).- The above compound (650 mg.) is dissolved in THF (50 ml.) and treated with 1,1,1,3,3,3-hexamethyldisilazane (6 ml.) and trimethylchlorosilane (1 ml.) at about 25° C. for 20 hrs., meanwhile protected from atmospheric moisture. The mixture is filtered on Celite filter aid, and the filtrate is freed of organic solvents under reduced pressure. The residue is taken up in xylene and reconcentrated under reduced pressure to yield an oil whose NMR spectrum is in agreement with the expected structure for the trimethylsilyl derivative of dl-15-oxo-17-phenyl-18,19,20-trinor-PGF$_{1\alpha}$.

C. dl-15-Methyl-17-phenyl-18,19,20-trinor-PGF$_{1\alpha}$ and 15$\beta$-epimer.- A solution of the trimethylsilyl derivative from above (600 mg.) in anhydrous ether (30 ml.) is treated with methyl magnesium bromide (0.55 ml., 3 M in ether) for 10 min. at about 25° C., then with additional 0.6 ml., meanwhile following the progress of the reaction by TLC (thin layer chromatography). The reaction mixture is finally poured into 100 ml. of saturated aqueous ammonium chloride and the ether layer separated. The ether solution is washed with brine, dried over sodium sulfate, and free of organic solvents under reduced pressure. The residue is taken up in ethanol (50 ml.) and treated with dilute acetic acid (3 drops in 10 ml. water) overnight at room temperature. The mixture is diluted with 100 ml.

of water and is then extracted with ethyl acetate. The organic extracts are washed with water, dried over sodium sulfate, and concentrated to 420 mg. of a mixture of dl-15-methyl-17-phenyl-18,19,20-trinor-PGF$_{1\alpha}$ and its 15$\beta$-epimer.

D. Title compound.- The above product is converted to the methyl esters. A solution of the acids (420 mg.) in THF (10 ml.) and ether (20 ml.) is treated for 2 hrs. at about 25° C. with excess diazomethane in ether (from 5 g. of N-methyl-N'-nitro-N-nitrosoguanidine, 15 ml. of 45% potassium hydroxide and 50 ml. of ether). Excess diazomethane is decomposed by the addition of dilute (2%) acetic acid in ether. The mixture is washed immediately with ice cold dilute sodium bicarbonate and brine solutions, dried over sodium sulfate, and concentrated under reduced pressure. The product is chromatographed on 80 g. of silica gel wet-packed in ethyl acetate, eluting with 225 ml. of 2%, and 285 ml. of 4% methanol in ethyl acetate, taking 15 ml. eluate fractions. Fractions 17–35 are combined and concentrated to give the title compound (190 mg.) as pale yellow crystals, melting 55°–65° C., NMR peaks at 7.20 (singlet), 5.62–5.5 (multiplet), 3.62 (singlet), 3.80–4.28 (broad multiplet), 1.33 (singlet) $\delta$; ion peaks at m/e 418, 400, 382, 368, and 91. Other fractions yield the 15$\beta$-epimer.

EXAMPLE 18 dl-15-Methyl-17-phenyl-18,19,20-trinor-PGF$_{1\beta}$ Methyl Ester (Formula XV: wherein ~ is alpha for the carboxyl-terminated side chain and beta for the hydroxyl)

Following the procedure of Example 17, but using dl-17-phenyl-18,19,20-trinor-PGF$_{1\beta}$ in place of that PGF$_{1\alpha}$ compound, there is obtained first the 15-oxo PGF$_{1\alpha}$ compound, then the corresponding trimethylsilyl derivative, and finally the title compound: NMR peaks at 7.20 (singlet), 5.55–5.88 (multiplet), 3.61 (singlet), 3.83–4.13 (broad multiplet) and 1.33 (singlet) $\delta$; ion peaks at m/e 403, 400, 385, 382, 328, and 313.

EXAMPLE 19 dl-15-Methyl-17-phenyl-18,19,20-trinor-PGE$_1$ Methyl Ester (Formula XI: wherein D is -(CH$_2$)$_5$-; R$_1$ and R$_3$ are methyl; R$_2$ and R$_4$ are hydrogen; C$_t$H$_{2t}$ is -(CH$_2$)$_2$-; s is zero; and ~ is alpha)

The PGF-type compound is oxidized to the PGE-type compound as follows. A solution of dl-15-methyl-17-phenyl-18,19,20-trinor-PGF$_{1\alpha}$ methyl ester (Example 17, 95 mg.) in 40 ml. of acetone is cooled to −10° C. To it is added Jones reagent (0.1 ml. of a solution of 21 g. of chromic anhydride, 60 ml. of water, and 17 ml. of concentrated sulfuric acid), precooled to 0° C., with vigorous stirring. After 5 min. at −10° C., thin layer chromatography on silica gel (acetic acid:methanol:chloroform, 5:5:90) of a small portion of the reaction mixture indicates about 50% reaction completion. An additional 0.06 ml. of Jones reagent is added to the still cold reaction mixture with stirring, and the mixture is stirred an additional 5 min. at −10° C. Isopropyl alcohol (1 ml.) is added to the cold reaction mixture. After 5 min., the mixture is filtered through a layer of diatomaceous silica (Celite). The filtrate is concentrated at reduced pressure, and the residue is mixed with 5 ml. of brine. The mixture is extracted repeatedly with ethyl acetate, and the combined extracts are washed with brine, dried with anhydrous sodium sulfate, and concentrated at reduced pressure. The residue is chromatographed on 20 g. of neutral silica gel, eluting with 50% ethyl acetate in Skellysolve B. Evaporation of the eluates gives the product, dl-15-methyl-17-phenyl-18,19,20-trinor-PGE$_1$ methyl ester.

Following the procedure of Example 19, there is substituted for the 15-methyl-17-phenyl-18,19,20-trinor-PGF$_{1\alpha}$ methyl ester, the free acid, the propyl ester, the octyl ester, the cyclopentyl ester, the benzyl ester, the phenyl ester, the 2,4-dichlorophenyl ester, the 2-tolyl ester, or the $\beta,\beta,\beta$-trichloroethyl ester of 15-methyl-17-phenyl-18,19,20-trinor-PGF$_{1\alpha}$, there is obtained the corresponding dl-15-methyl-17-phenyl-18,19,20-trinor-PGE$_1$ compound.

Following the procedure of Example 19, but substituting for the 15-methyl-17-phenyl-18,19,20-trinor-PGF$_{1\alpha}$ methyl ester, the methyl ester of each of the 15-methyl-17-phenyl-18,19,20-trinor-PGF$_{1\beta}$, PGF$_{2\alpha}$, PFG$_{2\beta}$, 5,6-dehydro-PGF$_{2\alpha}$, 5,6-dehydro-PFG$_{2\beta}$, dihydro-PGF$_{1\alpha}$, and dihydro-PGF$_{1\beta}$ compounds in their various natural or 15$\beta$ configurations and optical isomers is transformed to the corresponding PGE compound.

Following the procedure of Example 19, each of the various 15-alkyl-17-phenyl-18,19,20-trinor-PGF$_{1\alpha}$ methyl ester compounds, including the 15-ethyl, 15-propyl, 15-butyl, and 15-substituted isomeric forms of propyl and butyl, is transformed to the corresponding PGE compound.

Also following the procedure of Example 19, each of the 15-alkyl PGF-type acids and esters within the scope of Formulas XV to XVIII inclusive is transformed to a 15-alkyl PGE-type acid or ester encompassed by Formulas XI to XIV inclusive.

EXAMPLE 20 dl-17-Phenyl-18,19,20-trinor-PGA$_1$ Methyl Ester and Free Acid (Formula XIX: D is -(CH$_2$)$_5$-; R$_1$ is methyl or hydrogen; R$_2$, R$_3$, and R$_4$ are hydrogen; C$_t$H$_{2t}$ is -(CH$_2$)$_2$-, s is zero, and ~ is alpha)

Refer to Chart A. I. Using hydrochloric acid. A solution of dl-17-phenyl-18,19,20-trinor-PGE$_1$ methyl ester (Example 10, 400 mg.) in a mixture of THF (5 ml.) and 0.5 N hydrochloric acid (5 ml.) is maintained under nitrogen at 25° C. for 5 days. The resulting mixture is diluted with one volume of brine and extracted with a mixture of diethyl ether and dichloromethane (3:1). The extract is washed with brine, dried, and evaporated. The residue is dissolved in diethyl ether, and the solution is extracted with cold 5% aqueous sodium bicarbonate solution to give an aqueous layer A and a diethyl ether layer B. Aqueous layer A is acidified with dilute hydrochloric acid and then extracted with dichloromethane. This extract is washed with brine, dried, and concentrated to give the product free acid. Diethyl ether layer B is evaporated to give the product methyl ester.

II. Using acetic acid. A solution of dl-17-phenyl-18,19,20-trinor-PGE$_1$ methyl ester in a mixture of a glacial acetic acid (9 ml.) and water (1 ml.) is heated under nitrogen at 60° C. for 18 hrs. Then, the acetic acid and water are evaporated under reduced pressure, and the residue is chromatographed on 50 g. of acid-washed silica gel, eluting with a 25–100% gradient of ethyl acetate in Skellysolve B. The fractions containing the desired product free of starting material as shown by TLC are combined and evaporated to give 17-phenyl-18,19,20-trinor-PGA$_1$ methyl ester.

Following the procedures of Example 20, dl-17-phenyl-18,19,20-trinor-PGE$_1$ free acid (Example XX) is transformed to dl-17-phenyl-18,19,20-trinor-PGA$_1$ free acid.

Also following the procedures of Example 20, the Formula XI-to-XIV PGE compounds in their various spatial configurations are transformed to the corresponding Formula XIX-to-XXII PGA compounds, either as esters or as free acids.

EXAMPLE 21 dl-17-Phenyl-18,19,20-trinor-PGA$_1$ Methyl Ester

Refer to Chart C.

A solution of dl-methyl 7-[endo-6-(1,2-dihydroxy-4-phenylbutyl)-3-oxobicyclo[3.1.0]hex-2α-yl]heptanoate bismethanesulfonate (Example 10B, Formula XXXII, about 10 g.) in 75 ml. of acetone is mixed with 10 ml. of water and 20 ml. of saturated aqueous sodium bicarbonate solution. The mixture is refluxed under nitrogen for 4 hours. Then, the mixture is cooled, acidified with 5% hydrochloric acid, and extracted with ethyl acetate. The extract is washed with brine, dried, and evaporated to give the title compound.

Following the procedure of Example 21, each of the bismesylates defined after Examples 10 and 11 is transformed to the corresponding PGA-type ester, including the β,β,β-trichloroethyl esters. Thereafter, each of the β,β,β-trichloroethyl esters is transformed to the corresponding PGA-type free acid by the procedure of Example 38 hereinafter.

EXAMPLE 22 dl-15-Methyl-17-phenyl-18,19,20-trinor-PGA$_1$ Methyl Ester (Formula XIX: D is -(CH$_2$)$_5$-; R$_1$ and R$_3$ are methyl, R$_2$ and R$_4$ are hydrogen, C$_t$H$_{2t}$ is (CH$_2$)$_2$-, s is zero, and ~ is alpha)

A mixture of dl-15-methyl-17-phenyl-18,19,20-trinor-PGE$_1$ methyl ester (Example 19, 6 mg.), dicyclohexylcarbodiimide (20 mg.), copper (II) chloride dihydrate (2 mg.), and diethyl ether (2 ml.) is stirred under nitrogen at 25° C. for 16 hrs. Then, additional dicyclohexylcarbodiimide (20 mg.) is added, and the mixture is stirred an additional 32 hrs. at 25° C. under nitrogen. The resulting mixture is filtered, and the filtrate is concentrated under reduced pressure. The residue is chromatographed by preparative thin layer chromatography with the A-IX system to give the title compound.

Following the procedure of Example 22, but substituting for the phenyl-substituted PGE$_1$ compound, the methyl esters of 15-methyl-17-phenyl-18,19,20-trinor-PGE$_2$, -5,6-dehydro-PGE$_2$, and -dihydro-PGE$_1$; there are obtained the corresponding methyl esters of 15-methyl-17-phenyl-18,19,20-trinor-PGA$_2$, -5,6-didehydro-PGA$_2$, and -dihydro-PGA$_1$.

Also following the procedure of Example 22, but substituting for the phenyl-substituted PGE$_1$ compound, the methyl esters of 15-methyl-18-phenyl-19,20-dinor-PGE$_1$, -PGE$_2$, -5,6-didehydro-PGE$_2$, and -dihydro-PGE$_1$, there are obtained the corresponding methyl esters of 15-methyl-18-phenyl-19,20-dinor-PGA$_1$, -PGA$_2$, -5,6-dehydro-PGA$_2$, and -dihydro-PGA$_1$.

Also following the procedure of Example 22, each of the Formula XI-through-XIV compounds wherein R$_3$ is lower alkyl as disclosed above in Example 19, or its isomers, is transformed to the corresponding Formula-LXVII compound or its isomers.

EXAMPLE 23 dl-17-Phenyl-18,19,20-trinor-PGB$_1$ (Formula XXIII: D is -(CH$_2$)$_5$-; R$_1$, R$_2$, R$_3$, and R$_4$ are hydrogen; C$_t$H$_{2t}$ is -(CH$_2$)$_2$-; and s is zero)

Refer to Chart A.

A solution of dl-17-phenyl-18,19,20-trinor-PGE$_1$ (Example XX below, 200 mg.) in 100 ml. of 50% aqueous ethanol containing 10 g. of potassium hydroxide is kept at 25° C. for 10 hrs. under nitrogen. Then, the solution is cooled to 10° C. and neutralized by addition of 3 N. hydrochloric acid at 10° C. The resulting solution is extracted repeatedly with ethyl acetate, and the combined ethyl acetate extracts are washed with water and then with brine, dried, and evaporated to give the title compound.

Following the procedure of Example 23, dl-17-phenyl-18,19,20-trinor-PGA$_1$ is also transformed to the title compound.

Following the procedure of Example 23, the Formula XI-to-XIV PGE compounds and the Formula XIX-to-XXII PGA compounds and their isomers are transformed to the corresponding PGB compounds.

EXAMPLE 24 dl-13,14-Dihydro-17-phenyl-18,19,20-trinor-PGE$_1$ (Formula XIV: D is -(CH$_2$)$_5$-; R$_1$, R$_2$, R$_3$, and R$_4$ are hydrogen; C$_t$H$_{2t}$ is -(CH$_2$)$_2$-; s is zero; and ~ is alpha)

Refer to Chart B.

A solution of dl-17-phenyl-18,19,20-trinor-PGE$_1$ (Example 38 below, 100 mg.) in 10 ml. of ethyl acetate is shaken with hydrogen at about one atmosphere pressure at 25° C. in the presence of 5% palladium on charcoal (15 mg.). One equivalent of hydrogen is absorbed in about 90 min. The hydrogenation is then stopped, and the catalyst is removed by filtration. The filtrate is evaporated, and the residue is chromatographed on 25 g. of silica gel, eluting with a 50–100% ethyl acetate gradient in Skellysolve B. Those fractions shown by TLC to contain the desired product free of the starting product and dehydration products are combined and concentrated to give the title compound.

Following the procedure of Example 24, 17-phenyl-18,19,20-trinor-PGE$_1$ ethyl ester is reduced to 13,14-dihydro-17-phenyl-18,19,20-trinor-PGE$_1$ ethyl ester.

Also following the procedure of Example 24, 17-phenyl-18,19,20-trinor-PGE$_2$, trans-5,6-dehydro-17-phenyl-18,19,20-trinor-PGE$_1$, and 5,6-dehydro-17-phenyl-18,19,20-trinor-PGE$_2$ are each reduced to 13,14-dihydro-17-phenyl-18,19,20-trinor-PGE$_1$, using two equivalents of hydrogen for the first two reactions, and three equivalents of hydrogen for the third.

Also following the procedure of Example 24, the ethyl ester and the free acid form of the Formula XI-to-XIII PGE compounds in their various spatial configurations are transformed to the corresponding 13,14-dihydro PGE$_1$ compound by catalytic hydrogenation, using equivalents of hydrogen appropriate to the degree of unsaturation of the reactant, i.e., one equivalent for the PGE$_1$ type, two equivalents for the PGE$_2$ type and trans-5,6-dehydro-PGE$_1$ type, and three equivalents for the 5,6-dehydro-PGE$_2$ type.

Also following the procedure of Example 24, 17-phenyl-18,19,20-trinor-PGF$_{1\alpha}$ and its ethyl ester are reduced to 13, -14-dihydro-17-phenyl-18,19,20-trinor-PGF$_{1\alpha}$ and its ethyl ester, respectively.

Also following the procedure of Example 24, the ethyl ester and the free acid form of the Formula XV-to-XVII PGF compounds in their various spatial configurations are transformed to the corresponding 13,14-dihydro PGF$_{1\alpha}$ or PGF$_{1\beta}$ compound by catalytic hydrogenation, using equivalents of hydrogen appropriate to the degree of unsaturation of the reactant.

EXAMPLE 25 dl-13,14-Dihydro-17-phenyl-18,19,20-trinor- PGA$_1$ (Formula XXII: D is -(CH$_2$)$_5$-; R$_1$, R$_2$, R$_3$, and R$_4$ are hydrogen; C$_t$H$_{2t}$ is -(CH$_2$)$_2$-; s is zero; and ~ is alpha)

Refer to Chart B. A suspension of disodium azodiformate (50 mg.) in 5 ml. of absolute ethanol is added to a stirred solution of 17-phenyl-18,19,20-trinor-PGA$_1$ (Example 20, 50 mg.) in 10 ml. of absolute ethanol under nitrogen at 25° C. The mixture is made acid with glacial acetic acid, and then is stirred under nitrogen at 25° C. for 8 hrs. The resulting mixture is concentrated under reduced pressure, and the residue is mixed with a mixture of diethyl ether and water (1:1). The diethyl ether layer is separated, dried, and evaporated to give the title compound.

Following the procedure of Example 25, 17-phenyl-18,19,-20-trinor- PGA$_1$ methyl ester is reduced to 13,14-dihydro-17-phenyl-18,19,20-trinor-trinor-PGA$_1$ methyl ester.

Also following the procedure of Example 25, 17-phenyl-18,19,20-trinor-PGA$_2$ and 5,6-dehydro-17-phenyl-18,19,20-trinor-PGA$_2$ are each reduced to 13,14-dihydro-17-phenyl-18, -19,20-trinor-PGA$_1$, using amounts of the disodium azodiformate reactant appropriate to the degree of unsaturation of the reactant.

Also following the procedure of Example 25, the methyl ester and the free acid form of the Formula XI-into-XIII PGE compounds, the Formula XV-to-XVII PGF compounds, the Formula XIX-to-XXI PGA compounds, and the Formula XXIII-to-XXV PGB compounds are transformed to the corresponding 13,14-dihydro PGE$_1$, PGF$_1$, PGA$_1$, or PGB$_1$ compound by dimide reduction, using amounts of disodium azodiformate reactant appropriate to the degree of unsaturation of the PGE, PGF, PGA, or PGB reactant.

EXAMPLE 26

Dl -17-Phenyl-18,19,20-trinor-PGE$_2$ Ethyl Ester (Formula XII: A is -(CH$_2$)$_3$-, R$_1$ is ethyl; R$_2$, R$_3$, and R$_4$ are hydrogen; C$_t$H$_{2t}$ is -(CH$_2$)$_2$-; s is zero; -OH on -CR$_3$OH- is in the alpha configuration; and ~is alpha)

Refer to Chart C.

A. Glycol XXXI: dl-ethyl 7-[endo-6-(1,2-dihydroxy-4-phenylbutyl)-3-oxobicyclo[3.1.0]hex-2α-yl)-cis-5-heptenoate.- A solution of ketal XXX (Example 5, about 2.0 g.) in a 50 ml. of THF and 2.5 ml. of water is mixed with concentrated hydrochloric acid (2.5 ml.) and stirred at 25° C. under nitrogen for 6 hours. The resulting mixture is then concentrated under reduced pressure, and the residue is extracted with ethyl acetate. The extract is washed with brine, dried, and concentrated to give the glycol.

B. Bismesylate XXXII.- Following the procedure of Example 10B but replacing the glycol of that example with glycol XXXI of step A above, the corresponding bismesylate is obtained.

C. Title compound.- Following the procedure of Example 10C, but employing the bismesylate from above, the title compound is obtained.

Following the procedure of Example 26 but using in place of that ketal XXX each of the specific Formula-XXX exo and endo, alpha and beta, saturated, cis and trans ethylenic, and acetylenic bicyclo[3.1.0]hexane cyclic ketal esters defined above following Example 5 there are obtained the corresponding Formula-XXXI dihydroxy compounds. R$_{10}$ persists unchanged during this transformation, e.g., the Formula-XXXI β,β,β-trichloroethyl dihydroxy ester is obtained from the Formula-XXX β,β,β-trichloroethyl cyclic ketal ester.

Thereafter, following steps B and C, each of the corresponding PG-type compounds is obtained.

EXAMPLE 27

17-Phenyl-18,19,20-trinor-PGE$_2$Ethyl Ester and Free Acid (Formula XII: A is -(CH$_2$)$_3$-, R$_1$ is methyl or hydrogen; R$_2$, R$_3$, and R$_4$ are hydrogen; C$_t$H$_{2t}$ is -(CH$_2$)$_2$-; s is zero; -OH on -CR$_3$OH- is in the alpha configuration; and ~ is alpha)

Refer to Chart C.

A. Bismesylate XXXII: ethyl 7-[endo-6-(1,2-dihydroxy-4-phenylbutyl)-3-oxobicyclo[3.1.0]hex-2α-yl]-cis-5-heptenoate bismethanesulfonate.- Following the procedure of Example 10B but replacing that glycol with each of the optically active glycols obtained in Example 9 by resolution of ketal XXX of Example 5, the title compound is obtained, and separately, its enantiomer.

B. Title ester compound.- Following the procedure of Example 10C, but employing each of the above bismesylates, there is obtained the title ester compound, its 15β-epimer, and their respective enantiomers.

C. Title Free Acid Compound.- The ethyl ester title compound is transformed to the free acid by enzymatic hydrolysis (see West Germany Offenlegungsschrift No. 1 937 678, cited above).

a. Enzyme preparation.- A medium is prepared consisting of 2% corn steep liquor (a mixture of equal parts of cerelose and glucose) in tap water. This is brought to pH 4.5 by adding hydrochloric acid, and 1% of methyl oleate is added. Four 500 ml. flasks each containing 100 ml. of the above medium are inoculated with Cladosporium resinae (C1-11, ATCC 11,274, and are placed on a shaker at about 28° C. for 4 days. The culture is then placed in 40 ml. centrifuge tubes and centrifuged at about 2000 r.p.m. in a clinical centrifuge. The liquid is decanted from the centrifuge tubes and the collected cells are washed with cold water. The washed cells from 2 centrifuge tubes are suspended in 50 ml. of ice cold 0.05 M pH 7.0 phosphate buffer and placed in a small Waring blender cup chilled with ice. Glass beads are added and the suspended cells are churned in the blender for 15 minutes. The resulting suspension of broken cells is centrifuged in a clinical centrifuge at about 2000 r.p.m. for 15 minutes at room temperature, then the supernatant liquid is collected. This supernatant liquid contains Cladosporium resinae acylase and is used directly for the hydrolysis of alkyl esters or is stored, preferably frozen, until needed.

b. Esterase hydrolysis.- Ten milliliters of the supernatant liquid containing Cladosporium resinae acylase, prepared as described in part a above and 50 mg. of 17-phenyl-18,19,20-trinor-PGE$_2$ ethyl ester (Step B above) are shaken at room temperature under nitrogen for about 19 hrs., then 70 ml. of acetone is added and the whole is concentrated under reduced pressure to a residue. This residue is chromatographed over 10 g. of acid-washed silica gel (Silicar CC-4, Mallinckrodt). Elution is with mixed hexanes (Skellysolve B) containing increasing amounts of ethyl acetate, collecting 50 ml. fractions. Those fractions containing 17-phenyl-18,19,20-trinor-$PGE_2$ are combined and concentrated to yield the product: mass spectral peaks at 602, 587, 512, 497, 422, and 407.

EXAMPLE 28

16-Phenyl-17,18,19,20-tetranor-$PGE_2$ (Formula XII: A is -$(CH_2)_3$-; $R_1$, $R_2$, $R_3$, and $R_4$ are hydrogen; $C_tH_{2t}$ is -$CH_2$-; s is zero; -OH on -$CR_3OH$- is in alpha configuration; and $\sim$ is alpha)

Following the procedures of Example 27, but replacing the glycol of that example with each of the optically active glycols obtained following Example 9 by resolution of ketal XXX of Example 6, there is obtained as one of the products, the title compound: mass spectral peaks at 588, 573, and 497.

EXAMPLE 29

2a,2b-Dihomo-17-phenyl-18,19,20-trinor-$PGE_2$ (Formula XII: A is $(CH_2)_5$; $R_1$, $R_2$, $R_3$, and $R_4$ are hydrogen; $C_tH_{2t}$ is -$(CH_2)_2$-; s is zero; -OH on -$CR_3OH$- is in alpha configuration; and $\sim$ is alpha)

Following the procedures of Example 27, but replacing the glycol of that example with each of the optically active glycols obtained following Example 9 by resolution of ketal XXX of Example 8, there is obtained as one of the products, the title compound: mass spectral peaks at 396, 378, 360, 263, 261 and 245; NMR peaks at 7.2–7.4, 5.5–5.9 (multiplet), 5.2–5.5 (multiplet), 3.9–4.4 (broad) and 1.1–3.0 (broad) δ.

EXAMPLE 30

16,16-Dimethyl-17-phenyl-18,19,20-$PGE_2$ (Formula XII: A is -$(CH_2)_3$-; $R_1$, $R_2$, $R_3$, and $R_4$ are hydrogen; $C_tH_{2t}$ is -$C(CH_3)_2$-$CH_2$-; -OH on -$CR_3OH$- is in alpha configuration; and $\sim$ is alpha).

Following the procedures of Example 27, but replacing the glycol of that example with each of the optically active glycols obtained following Example 9 by resolution of ketal XXX of Example 7, there is obtained, as one of the products, the title compound: mass spectral peaks at 615, 525, 497, and 407; NMR peaks at 7.1, 5.8 (broad), 5.2–5.7 (multiplet), 3.6–4.2 (multiplet), 1.88 and 1.78 δ.

EXAMPLE 31

17-Phenyl-18,19,20-trinor-$PGF_{2\alpha}$ Methyl Ester and Free Acid.

Following the procedure of Example 12, but employing optically active 17-phenyl-18,19,20-trinor-$PGE_2$ methyl ester in the natural configuration (Example 26), the title compound methyl ester is obtained: mass spectral peaks at 603, 528, 513, 477, 438, and 423.

Following the procedure of Example 14, the above methyl ester is saponified to the title compound free acid: mass spectral peaks at 676, 661, 586, 571, 545, 514, and 496.

EXAMPLE 32

16-Phenyl-17,18,19,20-tetranor-$PGF_{2\alpha}$

Following the procedure of Example 12, 16-phenyl-17,18-19,20-tetranor-$PGE_2$ (Example 27) is transformed to the title compound: mass spectral peaks at 662, 647, and 571.

EXAMPLE 33

2a,2b-Dihomo-17-phenyl-18,19,20-trinor-$PGF_{2\alpha}$

Following the procedure of Example 12, 2a,2b-dihomo-17-phenyl-18,19,20-trinor $PGE_2$ (Example 28) is transformed to the title compound: mass spectral peaks at 398, 380, 362, 354, 336, and 326; NMR peaks at 7.2–7.4, 5.3–5.8 (broad), 4.5–4.8 (broad), 4.0–4.4 (broad), 3.5–3.9 (multiplet), and 1.1–3.0 (broad) δ.

EXAMPLE 34

16,16-Dimethyl-17-phenyl-18,19,20-trinor-$PGF_{2\alpha}$

Following the procedure of Example 12, 16,16-dimethyl-17-phenyl-18,19,20-trinor $PGE_2$ (Example 30) is transformed to the title compound: mass spectral peaks at 689, 599, 571 and 481; NMR peaks at 7.1, 5.0–5.8 (multiplet), 3.5–4.3 (multiplet), 1.1–2.9 (broad), 1.88, and 1.78 δ.

EXAMPLE 35 dl-17-Phenyl-18,19,20-trinor-$PGF_{2\alpha}$ Methyl Ester dl-5,6-Didehydro-17-phenyl-18,19,20-trinor-$PGF_{2\alpha}$ methyl ester (following Example 16) (200 mg.) in pyridine (4 ml.) and methanol (10ml.) is hydrogenated in the presence of a 5%-palladium-on-barium sulfate catalyst (200 mg.) at 25° and atmospheric pressure. The reaction is terminated when one equivalent of hydrogen is absorbed. The mixture is filtered and concentrated. Ethyl acetate is added and residual pyridine is removed by addition of ice and 3 N hydrochloric acid. The ethyl acetate layer is washed with 1 N. hydrochloric acid and then with brine, dried, and concentrated to yield the title compound.

Following the procedure of Example 35, the specific 5,6-didehydro-PGF compounds disclosed following Example 16 are reduced to the corresponding $PGF_2$ compounds. Likewise, the 5,6-didehydro-PGE, -PGA, and -PGB compounds disclosed herein are reduced to the corresponding $PGE_2$, $PGA_2$, and $PGB_2$ compounds.

EXAMPLE 36 dl-13,14-Dihydro-17-phenyl-18,19,20-trinor-$PGF_{1\alpha}$ Methyl Ester and
dl-13,14-Dihydro-17-phenyl-18,19,20-trinor-$PGF_{1\beta}$
Methyl Ester (Formula XVIII: D is -$(CH_2)_5$-, $R_1$ is methyl, $R_2$, $R_3$, and $R_4$ are hydrogen, $C_tH_{2t}$ is -$(CH_2)_2$-, s is zero, -OH on -$CR_3OH$- is in the alpha configuration, and $\sim$ is alpha for the carboxy chain and alpha or beta for the hydroxy).

Following the procedures of Example 12, the title compounds are prepared from the methyl ester of dl-13,14-dihydro-17-phenyl-18,19,20-trinor-$PGE_1$ (Example 24). Following the procedures of Example 14, the free acid forms of the title compounds are prepared by saponification of the methyl esters.

Following the procedures of Examples 12 and 14, the following $PGF_2$-type and 13,14-dihydro-$PGF_1$-type compounds within the scope of Formulas XVI and XVIII are prepared from the corresponding $PGE_2$ and 13,14-dihydro-PGE$_1$-type esters defined above, for example in and after Examples 24 and 26, in their optically active and racemic forms: 15$\beta$-17-phenyl-18,19,20-trinor-PGF$_{2\alpha}$ and -PGF$_{2\beta}$, 8$\beta$-17-phenyl-18,19,20-trinor-PGF$_{2\alpha}$ and -PGF$_{2\beta}$, 8$\beta$,-15$\beta$-17-phenyl-18,19,20-trinor-PGF$_{2\alpha}$ and -PGF$_{2\beta}$, 5,6-trans-17-phenyl-18,19,20-PGF$_{2\alpha}$ and -PGF$_{2\beta}$, 5,6-trans-15$\beta$-17-phenyl-18,-19,20-trinor-PGF$_{2\alpha}$ and -PGF$_{2\beta}$, 5,6-trans-8$\beta$-17-phenyl-18,19,20-trinor-PGF$_{2\alpha}$ and -PGF$_{2\beta}$, 5,6-trans-8$\beta$-15$\beta$-17-phenyl-18,19,20-trinor-PGF$_{2\alpha}$ and -PGF$_{2\beta}$, 13,14-dihydro-17-phenyl-18,19,20-trinor-PGF$_{1\alpha}$ and -PGF$_{1\beta}$, 13,14-dihydro-15$\beta$-17-phenyl-18,19,20-trinor-PGF$_{1\alpha}$ and -PGF$_{1\beta}$, 13,14-dihydro-8$\beta$-17-phenyl-18,19,20-trinor-PGF$_{1\alpha}$ and -PGF$_{1\beta}$, 13,14-dihydro-8$\beta$, 15$\beta$-17-phenyl-18,-19,20-trinor-PGF$_{1\alpha}$ and -PGF$_{1\beta}$, and their corresponding 18-phenyl-19,20-dinor-PGF type compounds.

EXAMPLE 37

17-Phenyl-18,19,20-trinor-PGA$_2$ (Formula XX: A is -(CH$_2$)$_3$-, R$_1$, R$_2$, R$_3$, and R$_4$ are hydrogen, C$_t$H$_{2t}$ is -(CH$_2$)$_2$-, s is zero, -OH on -CR$_3$OH- is in alpha configuration, and $\sim$ is alpha).

Following the procedures of Example 20, 17-phenyl-18,-19,20-trinor-PGE$_2$ (Example 27) is transformed to the title compound: mass spectral peaks at 512, 422, 407 and 350.

EXAMPLE 38 dl-17-Phenyl-18,19,20-trinor-PGE$_1$ (Formula XI: D is -(CH$_2$)$_5$-; R$_1$, R$_2$, R$_3$, and R$_4$ are hydrogen; C$_t$H$_{2t}$ is -(CH$_2$)$_2$-; s is zero; -OH in -CR$_3$OH- is in alpha configuration; and $\sim$ is alpha).

Zinc dust (420 mg.) is added to a solution containing dl-17-phenyl-18,19,20-trinor-PGE$_1$ $\beta$,$\beta$,$\beta$-trichloroethyl ester (following Example 11, 100 mg.) in 5 ml. of a mixture of acetic acid and water (9:1 v/v). This mixture is stirred under nitrogen 2 hrs. at 25° C. Ethyl acetate (4 volumes) is then added, followed by addition of 1 N hydrochloric acid (one volume). The ethyl acetate later is separated, washed with water and then with brine, dried, and concentrated. The residue is chromatographed on 15 g. of acid-washed silica gel (Silicar CC$_4$), being eluted with 50 and 80% ethyl acetate in Skellysolve B, collecting finally 100% ethyl acetate fractions. The fractions containing dl-17-phenyl-18,19,20-trinor-PGE$_1$ and no starting material or dehydration products as shown by TLC are combined and concentrated to give the title compound.

Following the procedure of Example 38, each of the $\beta$,$\beta$,$\beta$-tribromoethyl, -triiodoethyl, $\beta$,$\beta$-dibromoethyl, -diiodoethyl, and the $\beta$-iodoethyl esters of dl-17-phenyl-18,19,20-trinor-PGE$_1$ is converted to the free acid of dl-17-phenyl-18,19,20-trinor-PGE$_1$ by reaction with zinc dust and acetic acid.

Following the procedure of Example 38, the $\beta$,$\beta$,$\beta$-trichloroethyl ester of 1$a$,1$b$-dihomo-17-phenyl-18,19,20-trinor PGE$_2$ (Example 29) is converted to the respective free acid compound using zinc dust with either propionic, butyric, pentanoic, or hexanoic acid instead of acetic acid.

Following the procedure of Example 38, the $\beta$,$\beta$,$\beta$-trichloroethyl ester of each of the PGE, PGF, PGA and PGB type compounds represented by Formulas XI-XXVI in their various structural configurations and optical isomers and racemic mixtures is treated with zinc dust and acetic acid to obtain the corresponding free acid form of the compound. The esters are prepared by the procedures disclosed herein, using as intermediates Formula-XXX cyclic ketals or Formula-XXXVI olefins wherein R$_{10}$ is haloethyl, e.g., $\beta$,$\beta$,$\beta$-trichloroethyl. These intermediates are prepared by alkylation of the respective Formula-XXIX cyclic ketal (Chart C) or Formula-XXVII olefin (Chart D) with the appropriate alkylating agent wherein R$_{10}$ is haloethyl.

EXAMPLE 39

17-Phenyl-18,19,20-trinor-PGB$_1$ Methyl Ester.

A solution of diazomethane (about 0.5 g.) in diethyl ether (25 ml.) is added to a solution of dl-17-phenyl-18,19,-20-trinor-PGB$_1$ (Example 23, 50 mg.) in 25 ml. of a mixture of methanol and diethyl ether (1:1). The mixture is allowed to stand at 25° C. for 5 min. Then, the mixture is concentrated to give the title compound.

Following the procedure of Example 39, each of the other phenyl-substituted PGB-type, PGA-type, PGE-type, and PGF-type free acids defined above is converted to the corresponding methyl ester.

Also following the procedure of Example 39, but using in place of the diazomethane, diazoethane, diazobutane, 1-diazo-2-ethylhexane, and diazocyclohexane, there are obtained the corresponding ethyl, butyl, 2-ethylhexyl, and cyclohexyl esters of 17-phenyl-18,19,20-trinor-PGB$_1$. In the same manner, each of the other phenyl-substituted PGB-type, PGA-type, PGE-type, and PGF-type free acids defined above is converted to the corresponding ethyl, butyl, 2-ethyl-hexyl, and cyclohexyl esters.

EXAMPLE 40 dl-17-Phenyl-18,19,20-trinor-PGE$_1$ Methyl Ester Diacetate.

Acetic anhydride (5 ml.) and pyridine (5 ml.) are mixed with dl-17-phenyl-18,19,20-trinor-PGE$_1$ methyl ester (Example 10, 20 mg.), and the mixture is allowed to stand at 25° C. for 18 hrs. The mixture is then cooled to 0° C., diluted with 50 ml. of water, and acidified with 5% hydrochloric acid to pH 1. That mixture is extracted with ethyl acetate. The extract is washed successively with 5% hydrochloric acid, 5% aqueous sodium bicarbonate solution, water, and brine, dried and concentrated to give dl-17-phenyl-18,19,20-trinor PGE$_1$ methyl ester diacetate.

Following the procedure of Example 40, but replacing the acetic anhydride with propionic anhydride, isobutyric anhydride, and hexanoic acid anhydride, there are obtained the corresponding dipropionate, diisobutyrate and dihexanoate derivatives of dl-17-phenyl-18,19,20-trinor-PGE$_1$ methyl ester.

Also following the procedure of Example 40, but replacing the dl-17-phenyl-18,19,20-trinor-PGE$_1$ compound with 17-phenyl-18,19,20-trinor-PGF$_{1\alpha}$ and -PGF$_{1\beta}$, and 15-methyl-17-phenyl-18,19,20-trinor-PGF$_{1\alpha}$ and -PGF$_{1\beta}$, there are obtained the corresponding triacetate derivatives of the 17-phenyl-18,19,20-trinor-PGF compounds.

Also following the procedure of Example 40, each of the phenyl-substituted PGE-type, PGF-type, PGA-type, and PGB-type esters and free acids defined above is transformed to the corresponding acetates, propionates, isobutyrates, and hexanoates, the PGE-type derivatives being dicarboxyacylates, the PGF-type derivatives being tricarboxyacylates, and the PGA-type and PGB-type derivatives being monocarboxyacylates.

EXAMPLE 41

16-Phenyl-17,18,19,20-tetranor-PGE$_2$ Sodium Salt

A solution of 16-phenyl-17,18,19,20-tetranor-PGE$_2$ (Example 28, 100 mg.) in 50 ml. of a water-ethanol mixture (1:1) is cooled to 5° C. and neutralized with an equivalent amount of 0.1 N aqueous sodium hydroxide solution. The neutral solution is evaporated to give 16-phenyl-17,18,19,20-tetranor-PGE$_1$ sodium salt.

Following the procedure of Example 41 but using potassium hydroxide, calcium hydroxide, tetramethylammonium hydroxide, and benzyltrimethylammonium hydroxide in place of sodium hydroxide, there are obtained the corresponding salts of 16-phenyl-17,18,19,20-tetranor-PGE$_2$.

Also following the procedure of Example 41 each of the phenyl-substituted PGE-type, PGF-type, PGA-type, and PGB-type acids defined above is transformed to the sodium, potassium, calcium, tetramethylammonium, and benzyltrimethylammonium salts.

The following Examples 42–53 illustrate the preparation of compounds appearing in Charts H, I, J and K.

EXAMPLE 42

Endo-6-(4-phenyl-cis-1-butenyl)-exo-3-hydroxy-bicyclo[3.1.0]-hexan-exo-2-acetic acid, γ-Lactone (Formula LIX; Q is -(CH$_2$)$_2$C$_6$H$_5$)

Refer to Chart H. In benzene (1.21 l.), there is dissolved 100 g. of the lactone aldehyde, endo-6-formyl-exo-3-hydroxy-bicyclo[3.1.0]-hexan-exo-2-acetic acid, γ-lactone, (Formula LVIII) (U.S. Pat. No. 3 711 515, Jan. 16, 1973, formula VI; R. C. Kelly et al., J. Am. Chem. Soc. 95, 2746 (1973).

Separately, (3-phenylpropyl)triphenylphosphonium bromide (555 g., Preparation 1) and benzene (3 l.) are placed in another flask and are stirred while adding thereto dropwise at a moderate rate 685 ml. of a 15% solution of n-butyl lithium in hexane. The orange colored mixture is stirred for 1.5 hrs. after the addition is complete. After stirring is stopped, the mixture is allowed to settle, the supernatant solution is syphoned and is added, with stirring, to the benzene solution of the lactone aldehyde at the rate of 800 ml. to 1000 ml. per hour until the red color persists. The progress of the reaction is monitored by TLC and after the reaction is complete, the solution is concentrated and is chromatographed on a silica gel column packed with 5% ethyl acetate in Skellysolve B (SSB). Elution is performed as follows: (1) 4 l. of 5% ethyl acetate in SSB, (2) 4 l. of 10% ethyl acetate in SSB, (3) 6 l. of 10% ethyl acetate in SSB, (4) 6 l. of 15% ethyl acetate in SSB, and (5) 8 l. of 25% ethyl acetate in SSB. The fractions (3), (4) and (5) containing the desired compound are pooled and concentrated to give 155 g. of oily title compound, having IR absorptions at 1775, 1600, 1495, 1230, 1175, 1045, 1030, 920, 745, 700 cm$^{-1}$ and NMR peaks (CDCl$_3$) at 7.08, 5.6, 4.8, 4.4, 2.2–2.7, 1.92, 1.2–1.58 δ.

Following the procedure of Example 42, but replacing that optically active tricyclic aldehyde lactone with a racemic mixture of that compound and the mirror image thereof, there is obtained the corresponding racemic mixture.

EXAMPLE 43 endo-6-[1(R),2(S)-dihydroxy-4-phenylbutyl]-exo-3-hydroxybicyclo[3.1.0]-hexan-exo-2-acetic acid, γ-Lactone (Formula LX; Q is —(CH$_2$)$_2$C$_6$H$_5$)

Refer to Chart H. To a solution of the Formula LIX product of Example 42 (155 g.) in acetone (500 ml.) and water (50 ml.) there is added osmium tetroxide (250 mg.) in 2.5 ml. of tetrahydrofuran. A solution of N-methyl morpholine oxide hydrate (94 g.) in acetone (200 ml.) and water (314 ml.) is added to the reaction mixture with stirring while keeping the reaction temperature at 25°, and the mixture is stirred at that temperature for 6.5 hours to complete the reaction as monitored by TLC. The mixture is concentrated under vacuum in a 40° bath to remove most of the acetone. The residue is acidified with 10% hydrochloric acid to a pH of 3 to 4 and then is extracted with ethyl acetate. The extract is washed with brine, dried and then is evaporated under reduced pressure. The residue is dissolved in methylene chloride and then is chromatographed on a silica gel column packed with 60% ethyl acetate in Skellysolve B (SSB). Elution is performed with ethyl acetate and SSB as follows: (1) 35 l. of 60% ethyl acetate in SSB, (2) 15 l. of 80% ethyl acetate in SSB, (3) 28 l. of 80% ethyl acetate in SSB, (4) 4 l. of 80% ethyl acetate in SSB, (5) 8 l. of 80% ethyl acetate in SSB and (6) 35 l. of 10% methanol in ethyl acetate. From fraction (3) there is recovered 88 g. of the title compound having IR absorptions at 3430, 1760, 1600, 1495, 1450, 1415, 1360, 1335, 1295, 1260, 1230, 1185, 1095, 1030, 925, 750, 705; NMR peaks (CDCl$_3$) at 7.2, 4.75, 3.65, 2.5–3.1, 1.0–2.5 δ and mass spectral peaks at 302, 180, 150, 149, 121, 108, 107, 93, 92, 91, 79.

Following the procedure of Example 43, but replacing the optically active tricyclic lactone with a racemic mixture of that compound and the mirror image thereof, there is obtained the corresponding racemic mixture.

EXAMPLE 44

Endo-6-[1(R),2(S)-dihydroxy-4-phenylbutyl ethyl orthopropionate]-exo-3-hydroxybicyclo[3.1.0]-hexan-exo-2-acetic acid, γ-Lactone (Formula LXI; Q is -(CH$_2$)$_2$C$_6$H$_5$; R$_{41}$ and R$_{42}$ are -C$_2$H$_5$)

Refer to Chart H. The β-glycol Formula LX product (88 g.) of Example 43 is dissolved in 1 l. of benzene and then is evaporated under vacuum. To the residue is added triethyl orthopropionate (87 ml.) and benzene (1 l.) and then about 250 ml. of benzene is removed by evaporation under vacuum. Pyridine hydrochloride (0.6 g.) is added and the mixture is allowed to stand for about 1 hr. at 25°. Triethylamine (3 drops) is added and then the reaction mixture is evaporated under vacuum to yield an oily title compound (110 g.). The title compound has an R$_f$ of 0.57 on silica gel prespotted with triethylamine and developed in 50% ethyl acetate-cyclohexane.

Following the procedure of Example 44, but replacing the optically active tricyclic lactone glycol with a racemic mixture of that compound and the mirror image thereof, there is obtained the corresponding racemic mixture.

EXAMPLE 45

3α-(Formyloxy)-5α-hydroxy-2β-[(3S)-3-propionyloxy-5-phenyl-trans-1-pentenyl]-1α-cyclopentaneacetic acid, γ-Lactone (Formula LXII; Q is -(CH₂)₂C₆H₅ and R₄₁ is -C₂H₅)

Refer to Chart H. Formic acid (440 ml.) is stirred with acetic anhydride (8.8 ml.) for 20 min. The flask is swept with dry nitrogen and cooled to about 10°. Then the crude cyclic orthopropionate Formula LXI product (110 g.) of Example 44 is rapidly poured into the vigorously stirred formic acid and is rinsed in with about 40 ml. of methylene chloride. Stirring is continued for 4 minutes and then sodium hydroxide (600 ml. of 1 N) is added. The mixture is diluted with brine (1.5 l.) and extracted with methylene chloride. The extract is washed with a saturated solution of sodium bicarbonate, and then with brine. The mixture is dried and concentrated to give an oil having NMR peaks (CDCl₃) at 7.87, 7.1, 5.5, 4.6–5.3, 2.2. and 1.1. This oil is used without purification in the following Example.

Following the procedure of Example 45, but replacing that optically active cyclic lactone orthopropionate with a racemic mixture of that compound and the mirror image thereof, there is obtained the corresponding racemic mixture.

EXAMPLE 46

3α,5α-Dihydroxy-2β-[(3S)-3-hydroxy-5-phenyl-trans-1-pentenyl]-1α-cyclopentaneacetic acid, triol acid (Formula LXIV; Q is -(CH₂)₂C₆H₅)

Refer to Charts H and I. The crude lactone product of Example 45 is mixed with 875 ml. of methanol, then 875 ml. of 1 N sodium hydroxide is added and the mixture is stirred for 1 hr. at 25°. The mixture is concentrated to about 900 ml. under reduced pressure on a 40° bath. The mixture is then saturated with sodium chloride and cooled to about 10°. The aqueous solution is covered with ethyl acetate and is slowly acidified with 10% phosphoric acid to pH 5 with continuous stirring and cooling. The phases are separated and extracted with ethyl acetate. The aqueous phase is again covered with ethyl acetate and is acidified to pH 4 with more 10% phosphoric acid. The phases are separated and are extracted again with ethyl acetate. The combined organic extracts are washed with brine, dried, filtered and concentrated on a rotary evaporator until crystallization is well started. The mixture is refrigerated for 16 hrs. at −10°. The crystals are filtered and washed with cold ethyl acetate-Skellysolve B (3:1) and dried under vacuum at 50° to give 57.5 g. of the title compound; m.p. 125°–127° C.; having IR absorptions (mull) at 3390, 3260, 2730, 2660, 2630, 1710, 1600, 1495, 1350, 1340, 1305, 1275, 1240, 1195, 1125, 1075, 1050, 1035, 995, 970, 965, 940, 750, 700 cm⁻¹.

Following the procedure of Example 46, but replacing the optically active lactone with a racemic mixture of that compound and the mirror image thereof, there is obtained the corresponding racemic mixture.

EXAMPLE 47

3α,5α-Dihydroxy-2β-[([3S)-3-hydroxy-5-phenyl-trans-1-pentenyl]-1α-cyclopentaneacetic acid γ-Lactone (Formula LXIII; Q is -(CH₂)₂C₆H₅)

Refer to Chart I. To a flask containing the crystalline triol acid (14.4 g.) obtained in Example 46 and 450 ml. of chloroform, there is added a solution (5 ml.) of a saturated solution of pyridine hydrochloride in methylene chloride. The mixture is stirred and refluxed with heat until TLC (acetic acid:methanol:chloroform-10:10:80) indicates lactone LXIII formation is complete. The mixture is then cooled to room temperature. The title compound is not isolated and the crude product is directly used in the following Example. Its m.p. is 51°–53° C. and the IR absorptions (mull) are 3320, 1765, 1665, 1625, 1600, 1495, 1160, 1085, 1060, 1040, 1000, 970, 700 cm⁻¹.

Following the procedure of Example 47, but replacing the optically active triol acid with a racemic mixture of that compound and the mirror image thereof, there is obtained the corresponding racemic mixture.

EXAMPLE 48

3α,5α-Dihydroxy-2β-[(3S)-3-hydroxy-5-phenyl-trans-1-pentenyl]-1α-cyclopentaneacetic acid, γ-Lactone, 4,3'-bis(tetrahydropyranyl) ether (Formula LXXI; Q is -(CH₂)₂C₆H₅, J is tetrahydropyranyl and

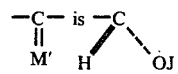

Refer to Chart K. To the product of Example 47 at 25°, there is added dihydropyran (50 ml.) and a saturated solution of pyridine hydrochloride in methylene chloride (5 ml.). The mixture is stirred at 25° until formation of the bistetrahydropyranyl ether is complete as monitored by TLC (50% ethyl acetate-Skellysolve B). The reaction mixture is washed with saturated sodium bicarbonate solution, then with brine, dried, filtered and the liquid is concentrated under vacuum. There is obtained an oil (34 g.) having IR absorptions of 1775, 1440, 1425, 1335, 1195, 1150, 1120, 1070, 1030, 1015, 970, 910, 900, 865, 815, 755 and 705 cm⁻¹.

Following the procedure of Example 48, but replacing the optically active lactone with a racemic mixture of that compound and the mirror image thereof, there is obtained the corresponding racemic mixture.

EXAMPLE 49

3α,5α-Dihydroxy-2β-[(3S)-3-hydroxy-5-phenyl-trans-1-pentenyl]-1α-cyclopentane-acetaldehyde-γ-Lactol,4,3'-bis(tetrahydropyranyl) ether (Formula LXII; Q is -(CH₂)₂C₆H₅, J is tetrahydropyranyl and

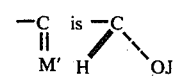

Refer to Chart K. To a solution of the product (34g.) of Example 48 in toluene (150 ml.) at −50° there is added di-isobutylaluminum hydride (150 ml. of 10% solution in toluene) over a period of 15 minutes. The reaction mixture is stirred for an additional period of pound and the mirror image thereof, there is obtained the corresponding racemic mixture.

EXAMPLE 52

17-Phenyl-18,19,20-trinor-PGE$_2$,11,15-bis(tetrahydropyranyl) ether (Formula LXXV; Q is -(CH$_2$)$_2$C$_6$H$_5$, J is tetrahydropyranyl,

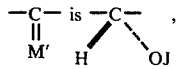

R$_2$ is H and A is -(CH$_2$)$_3$-.)

Refer to Chart K. The 17-phenyl PGF$_{2\alpha}$ bis(tetrahydropyranyl) ether product (5.7 g.) of Example 50 is dissolved in acetone (100 ml.) and the solution is cooled to $-10°$. While the solutin is stirred and is maintained at that temperature, there is added dropwise over a period of 5 minutes, Jones' reagent (5 ml., prepared by mixing 26.7 g. CrO$_3$ in 23 ml. of H$_2$SO$_4$, plus water to make 100 ml.). The reaction mixture is stirred for 10 minutes until the reaction is complete as monitored by TLC. Then isopropylalcohol (3 ml.) is added and the reaction mixture is stirred 5 minutes more. Then water (200 ml.) is added and the reaction mixture is extracted 3 times with methylene chloride. The combined extracts are washed with bine, dried, filtered and concentrated under reduced pressure. There is obtained 5.9 g. of yellow oil of the title compound. This is used without purification in the next Example.

Following the procedure of Example 52, but replacing the 17-phenyl PGF$_{2\alpha}$ bis(tetrahydropyranyl) ether with a racemic mixture of that compound and the mirror image thereof, there is obtained the corresponding racemic mixture.

EXAMPLE 53

17-Phenyl-18,19,20-trinor-PGE$_2$ (Formula LXXVI; Q is -(CH$_2$)$_2$C$_6$H$_5$,

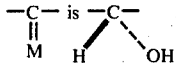

R$_2$ is H and A is -(CH$_2$)$_3$-

Refer to Chart K. The 17-phenyl PGE bis(tetrahydropyranyl) ether product (5.9 g.) of Example 52 is dissolved in acetic acid (60 ml.) and this solution is diluted with water (30 ml.) and tetrahydrofuran (3 ml.). The solution is heated to 40° and is allowed to stand at that temperature for 4 hours. The solution is then diluted with brine (350 ml.) and is extracted three times with 75 ml. portions of methylene chloride. The three extracts are combined and are washed three times with brine. The combined methylene chloride extract is dried, filtered and concentrated. The solution is chromatographed on 100 g. of acid washed silica gel packed with 50% ethyl acetate in SSB. Elution is performed as follows: (1) 500 ml. of 50% ethyl acetate in SSB, (2) 500 ml. of 60% ethyl acetate in SSB, (3) 500 ml. of 80% ethyl acetate in SSB, (4) 200 ml. of 100% ethyl acetate, (5) 100 ml. of 100% ethyl acetate, (6) 700 ml. of 100% ethyl acetate, (7) 300 ml. of ethyl acetate and 5% methanol, (8) 200 ml. ethyl acetate and 5% methanol and (9) 500 ml. of ethyl acetate and 10% methanol. Fractions (6) and (7) contain the 17-phenyl PGE$_2$ title compound. This is recrystallized from anhydrous ether to yield 1.23 g. Fractions (5), (8) and (9) rechromatographed to obtain an additional amount of the 17-phenyl PGE$_2$ title compound which is recrystallized from anhydrous ether to yield 0.26 g. The combined product (1.49 g.) is recrystallized from ethyl acetate-SSB using charcoal. It has a melting point of 95°–96° C., and has NMR peaks (CDCl$_3$) at 7.2, 6.3, 5.6, 5.35 and 4.1 δ.

EXAMPLE 54

(15R)-15-Methyl-17-phenyl-18,19,20-trinor-PGF$_{2\alpha}$, methylester
(15S)-15-Methyl-17-phenyl-18,19,20-trinor-PGF$_{2\alpha}$, methylester To a solution of 17-phenyl-PGF$_{2\alpha}$ (1.165 g.) in 1,4-dioxane (30 ml.) is added 2,3-dichloro-5,6-dicyano-1,4-benzoquinone (817 mg.) and the reaction mixture, under nitrogen atmosphere, is stirred for 72 hrs. at 25°. The mixture is filtered and the and the solids are washed with methylene chloride. The solution is concentrated and is chromatographed on 140 g. of acid-washed silica packed with ethyl acetate and Skellysolve B (50:50). Elution is performed with (1) 3 l. of ethyl acetate and Skellysolve B (50:50), (2) 3 l. ethyl acetate and (3) 3 l. of ethyl acetate and 1 l. of 10% methanol (100 ml. fractions). The eluate fractions 16–73 are combined, treated with charcoal filter and concentrated to 1.045 g. of 15-keto-17-phenyl-18,19,20-trinor-PGF$_{2\alpha}$.

To a solution of 15-keto-17-phenyl-PGF$_{2\alpha}$ in tetrahydrofuran, there are added hexamethyldisilazane (22 ml.) and trimethylchlorosilane (5 ml.) and the mixture, under nitrogen, is stirred for 18 hrs. at 25°. The solution is concentrated, the residue dissolved in xylene, filtered and concentrated to give an oily product (1.6 g.), the trimethyl silyl derivative of 17-phenyl-18,19,20-trinor-PGF$_{2\alpha}$.

The oily product is dissolved in diethyl ether (50 ml.), cooled to 0° under nitrogen and to it is added dropwise 3M ethereal methyl magnesium bromide (1.5 ml.). The reaction mixture is allowed to warm to room temperature and it is confirmed by TLC that no ketone remains. The mixture is poured into saturated aqueous ammonium chloride and ice and is extracted with diethyl ether. The organic layer is washed with brine, dried and concentrated to give a tertiary alcohol (1.6 g.), a mixture of C-15 epimers, the (15R)-15-methyl-17-phenyl-18,19,20-trinor-PGF$_{2\alpha}$ and (15S)-15-methyl-17-phenyl-8,19,20-trinor-PGF$_{2\alpha}$.

The mixture of epimers is dissolved in ethanol (60 ml.), diluted with water (40 ml.) and stirred for 3 hrs. at room temperature. The solution is concentrated to remove ethanol (35° max. temp.), to the residue is added potassium bisulfate and then the mixture is extracted with ethyl acetate. The organic layer is washed with brine, dried and concentrated and then is esterified with ethereal diazomethane. The product is chromatographed on 150 g. of neutral silica packed with 10% acetone and methylene chloride and is eluted (100 ml. fractions) using (1) 3 l. of 10% acetone and methylene chloride, (2) 3 l. of 40% acetone and methylene chloride and (3) 2 l. of 50% acetone and methylene chloride. Fractions 53–58 are combined to give 161 mg. of (15R)-15-methyl-17-phenyl-18,19,20-trinor-PGF$_{2\alpha}$, methyl ester, having IR absorptions at 3380, 1735, 1600, 1495, 1455, 1440, 1370, 1225, 1170, 1155, 1120, 1095, 1060, 1030, 975, 925, 750

10 minutes until the reaction is complete as monitored by TLC (50% ethylacetatecyclohexane). The reaction mixture is removed from the cooling bath and a mixture of tetrahydrofuran (60 ml.) and water (60 ml.) is added slowly during a period of 10–15 minutes. The mixture is stirred until it reaches room temperature. The mixture is filtered and the filter cake is washed with benzene. The filtrate is washed with brine, then dried and concentrated under vacuum. There is obtained about 31 g. of oily lactol product having IR absorptions at 3400, 1440, 1340, 1200, 1175, 1120, 1070, 1020, 970, 870, 815, 735 and 700 cm$^{-1}$.

Following the procedure of Example 49, but replacing the optically active Formula LXXI compound with a racemic mixture of that compound and the mirror image thereof, there is obtained the corresponding racemic mixture.

PREPARATION 7

(2-Carboxyethyl) triphenylphosphonium Bromide.

A mixture of 3-bromopropionic acid (50 g.), triphenylphosphine (85.8 g.) and acetonitrile (250 ml.) is heated under reflux for 23 hrs. and then 166 ml. of acetonitrile is removed by distillation. After cooling the remaining solution to room temperature, benzene (250 ml.) is added and the mixture is allowed to stand for 16 hrs. The solid which separates is removed by filtration to give 120.5 g. of the title compound, m.p. 197°–200°; infrared absorptions at 2900, 2610, 2540, 1745, 1620, 1585, 1485, 1435, 1385, 1325, 1230, 1110, 750, 725 and 690 cm$^{-1}$; NMR peaks at 2.7–3.3 (broad), 3.5–4.2 (broad) and 7.6–7.9 (multiplet) δ.

PREPARATION 7A a. (4-Carboxybutyl) triphenylphosphonium Bromide
b. (6-Carboxyhexyl) triphenylphosphonium Bromide
c. (8-Carboxyoctyl) triphenylphosphonium Bromide Following the procedure of Preparation 7 but replacing 3-bromopropionic acid with the equivalent amount of (a) 5-bromopentanoic acid, (b) 7-bromoheptanoic acid and (c) 9-bromononanoic acid the title compounds (a), (b) and (c) are obtained.

EXAMPLE 50

17-Phenyl-18,19,20-trinor-PGF$_{2\alpha}$ ,11,15-bis-(tetrahydropyranyl) ether (Formula LXXIII; Q is -(CH$_2$)$_2$C$_6$H$_5$, J is tetrahydropyranyl,

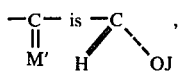

R$_2$ is H, A is -(CH$_2$)$_3$-)

Refer to Chart K. The oily lactol product (31 g.) of Example 49 is dissolved in dimethyl sulfoxide (35 ml.). Separately to a further quantity (320 ml.) of dimethyl sulfoxide, in a nitrogen atmosphere, there is added sodium hydride (18.9 g. of 50% dispersion) with stirring, and the mixture is heated and reacted at 60°–70° until the reaction is complete. The reaction mixture is cooled to 10° C. and carboxybutyl triphenylphosphonium bromide (Preparation 8, 87 g.) is added while maintaining the temperature below 35° to form a Wittig reaction solution. This solution is cooled to 15° C. and then the lactol solution is added dropwise over a period of 15 minutes and while maintaining the temperature at 15°–30°. This reaction mixture is stirred, mixed with benzene (800 ml.), cooled by adding ice and then to it there is added, with shaking, a solution of potassium hydrogen sulfate (60 g.) in water (650 ml.). The phases are allowed to separate, the organic (upper) phase is removed, the aqueous phase is washed with benzene and the organic phases are combined. The combined organic phases are washed with water, dried, filtered and concentrated. The resultant oily product is chromatographed over 350 g. of acid-washed silica gel. Elution is carried out with (1) 1.75 l. of 33% ethyl acetate in SSB, (2) 0.25 l. of 33% ethyl acetate in SSB, (3) 2 l. of 40% ethyl acetate in SSB, (4) 0.5 l. of 50% ethyl acetate in SSB, (5) 1.5 l. of 50% acetate in SSB and (6) 2 l. of 60% ethyl acetate in SSB. Fractions (3) and (4) yield 25 g. of the title compound. Fractions (1), (2) and recrystallized product from fractions (5) and (6) are rechromatographed under the same conditions and an additional 2.45 g. of the title compound is obtained. The desired product fractions are combined, concentrated under vacuum at 35°–40° C. and there is obtained 26.4 g. of pale-yellow oil having NMR peaks (CDCl$_3$) at 7.2, 6.3, 5.3–5.7, 4.7 and 3.3–4.2 δ.

Following the procedure of Example 50, but replacing the optically active lactol product with a racemic mixture of that compound and the mirror image thereof, there is obtained the corresponding racemic mixture.

EXAMPLE 51

17-Phenyl-18,19,20-trinor-PGF$_{2\alpha}$ (Formula LXXIV; Q is -(CH$_2$)$_2$C$_6$H$_5$ and A is -(CH$_2$)$_3$-.)

Refer to Chart K. The 17-phenyl PGF$_{2\alpha}$ bis(tetrahydropyranyl) ether product (6.95 g.) of Example 50 is dissolved in acetic acid (80 ml.) and this solution is diluted with water (40 ml.) and tetrahydrofuran (4 ml.). The solution is heated to 40° C. and is allowed to stand at that temperature for 4 hours. The solution is then diluted with brine (450 ml.) and is extracted four times with 100 ml. portions of chloroform. The first three extracts are combined with and are washed three times with brine. The combined brine washings are backwashed with the fourth chloroform extract. All the chloroform extracts are combined, dried, filtered and concentrated to obtain an oil. The oil is dissolved in methylene chloride and is chromatographed over 150 g. of acid washed silica gel packed with 50% ethyl acetate in SSB. Elution is performed as follows: (1) 500 ml. of 50% ethyl acetate in SSB, (2) 500 ml. of 75% ethyl acetate in SSB, (3) 500 ml. of 100% ethyl acetate, (4) 250 ml. ethyl acetate and 2.5% methanol, (5) 250 ml. of ethyl acetate and 2.5% methanol, (6) 500 ml. of ethyl acetate and 5% methanol, (7) 500 ml. ethyl acetate and 7.5% methanol and (8) 500 ml. ethyl acetate and 10% methanol. Fractions (5), (6) and (7) yield the desired 17-phenyl PGF$_{2\alpha}$ title product (1.974 g.). Fractions (4) and (8) are rechromatographed to obtain 1.302 g. of the desired 17-phenyl PGF$_{2\alpha}$ title product. The product after evaporation is a very viscous nearly colorless gum. It is recrystallized from ethyl acetate-SSB. It has a melting point of 79°–80° C., and IR absorptions (mull) at 3430, 3340, 2950b, 2630, 1695, 1600, 1495, 1275, 1245, 1100, 1000, 975 and 695 cm$^{-1}$ and NMR peaks (CDCl$_3$) at 7.2, 5.68, 5.45 and 4.1 δ.

Following the procedure of Example 51, but replacing the optically active 17-phenyl PGF$_{2\alpha}$ bis(tetrahydropyranyl) ether with a racemic mixture of that comand 705 cm$^{-1}$ and NMR peaks (CDCl$_3$) at 7.19, 5.75–5.05, 4.30–3.70, 3.62, 1.32 δ.

Continued elution yielded 220 mg. of a product which upon recrystallization from ethyl acetate Skellysolve B yielded 88 mg. of 15(S)-15-methyl-17-phenyl-18,19,20-trinor PGF$_{2\alpha}$, methyl ester having IR absorptions at 3290, 1730, 1600, 1585, 1495, 1315, 1225, 1175, 1105, 1040, 975, 910, 745, 740 and 700 cm$^{-1}$ and NMR peaks (CDCl$_3$) at 7.45–7.10, 5.85–5.30, 4.30–3.80, 3.68 and 1.38 δ.

EXAMPLES 55 – 176

Following the procedures of Preparations 1–5, but replacing the phenyl-substituted alkyl halide, e.g. (3-bromopropyl) benzene of Preparation 1, by various phenyl-substituted alkyl halides, there are obtained the corresponding triphenylphosphonium halides of the formula (φ)$_3$P$^+$-CH$^-$-Q, wherein φ is phenyl and Q is as defined above.

Following the procedure of Preparation 7, but replacing the halo-substituted acid by various halo-substituted acids, there are obtained the corresponding ω-carboxy triphenylphosphonium halides of the formula (φ)$_3$P$^+$-CH$^-$-A-COOH, wherein φ and A are as defined above.

Following the procedures of Examples 42–54, the optically active compound of the Formula LVIII is transformed to compounds of the Formulas LXXIV and LXXVI, using the various triphenylphosphonium halides and ω-carboxy triphenylphosphonium halides prepared as described above.

Tables III and IV below list the Formulas LXXIV and LXXVI PG compounds that are obtained.

Table III

Final PGF Compound (Formula LXXIV)

| Ex. | Q | A | M | R$_3$ |
|---|---|---|---|---|
| 55 | —(CH$_2$)$_3$—φ | —CH$_2$— | α | H |
| 56 | —(CH$_2$)$_3$—φ | —CH$_2$— | β | H |
| 57 | —(CH$_2$)$_3$—φ | —CH$_2$— | α | CH$_3$ |
| 58 | —(CH$_2$)—φ | —CH$_2$— | β | CH$_3$ |
| 59 | —(CH$_2$)$_3$—φ | —CH$_2$— | α | C$_2$H$_5$ |
| 60 | —(CH$_2$)—φ | —CH$_2$— | β | C$_2$H$_5$ |
| 61 | —CH$_2$—φ | —CH$_2$— | α | H |
| 62 | —CH$_2$—φ | —CH$_2$— | β | H |
| 63 | —CH$_2$—φ | —CH$_2$— | α | CH$_3$ |
| 64 | —CH$_2$—φ | —CH$_2$— | β | CH$_3$ |
| 65 | —CH$_2$—φ | —CH$_2$— | α | C$_2$H$_5$ |
| 66 | —CH$_2$—φ | —CH$_2$— | β | C$_2$H$_5$ |
| 67 | —C(CH$_3$)$_2$—CH$_2$—φ | —(CH$_2$)$_3$— | α | H |
| 68 | —C(CH$_3$)$_2$—CH$_2$—φ | —(CH$_2$)$_3$— | β | H |
| 69 | —C(CH$_3$)$_2$—CH$_2$—φ | —(CH$_2$)$_3$— | α | CH$_3$ |
| 70 | —C(CH$_3$)$_2$—CH$_2$—φ | —(CH$_2$)$_3$— | β | CH$_3$ |
| 71 | —(CH$_2$)$_4$—φ | —(CH$_2$)$_3$— | α | H |
| 72 | —(CH$_2$)$_4$—φ | —(CH$_2$)$_3$— | β | H |
| 73 | —(CH$_2$)$_4$—φ | —(CH$_2$)$_3$— | α | CH$_3$ |
| 74 | —(CH$_2$)$_4$—φ | —(CH$_2$)$_3$— | β | CH$_3$ |
| 75 | —(CH$_2$)$_5$—φ | —CH$_2$— | α | H |
| 76 | —(CH$_2$)$_5$—φ | —(CH$_2$)$_3$— | α | H |
| 77 | —(CH$_2$)$_7$—φ | —CH$_2$— | α | H |
| 78 | —(CH$_2$)$_7$φ | —(CH$_2$)$_3$— | α | H |
| 79 | —(CH$_2$)$_7$φ | —(CH$_2$)$_5$— | α | H |
| 80 | —CHF—(CH$_2$)$_3$φ | —CH$_2$— | α | H |
| 81 | —CHF—(CH$_2$)$_3$φ | —(CH$_2$)$_3$— | α | H |
| 82 | —CHF—(CH$_2$)$_3$φ | —(CH$_2$)$_3$— | β | H |
| 83 | —CHF—(CH$_2$)$_3$φ | —(CH$_2$)$_3$— | α | CH$_3$ |
| 84 | —CHF—(CH$_2$)$_3$φ | —(CH$_2$)$_3$— | β | CH$_3$ |
| 85 | —CHF—(CH$_2$)$_3$φ | —(CH$_2$)$_5$— | α | H |
| 86 | —CF$_2$—(CH$_2$)$_2$φ | —CH$_2$— | α | H |
| 87 | —CF$_2$—(CH$_2$)$_2$φ | —(CH$_2$)$_3$— | α | H |
| 88 | —CF$_2$—(CH$_2$)$_2$φ | —(CH$_2$)$_3$— | β | H |
| 89 | —CF$_2$—(CH$_2$)$_2$φ | —(CH$_2$)$_3$— | α | CH$_3$ |
| 90 | —CF$_2$—(CH$_2$)$_2$φ | —(CH$_2$)$_3$— | β | CH$_3$ |
| 91 | —CF$_2$—(CH$_2$)$_2$φ | —(CH$_2$)$_3$— | α | C$_2$H$_5$ |
| 92 | —CF$_2$—(CH$_2$)$_2$φ | —(CH$_2$)$_3$— | β | C$_2$H$_5$ |
| 93 | —CF$_2$—(CH$_2$)$_4$—φ | —CH$_2$— | α | H |
| 94 | —CF$_2$—(CH$_2$)$_4$φ | —(CH$_2$)$_3$— | α | H |
| 95 | (o-CH$_3$-phenyl) | —(CH$_2$)$_3$— | α | H |
| 96 | (o-CH$_3$-phenyl) | —(CH$_2$)$_3$— | β | H |
| 97 | (o-CH$_3$-phenyl) | —(CH$_2$)$_3$— | α | CH$_3$ |
| 98 | (o-CH$_3$-phenyl) | —(CH$_2$)$_3$— | β | CH$_3$ |
| 99 | (p-Cl-phenyl) | —(CH$_2$)$_3$— | α | H |
| 100 | (p-Cl-phenyl) | —(CH$_2$)$_3$— | β | H |

Table III-continued

Final PGF Compound (Formula LXXIV)

| Ex. | Q | A | M | $R_3$ |
|---|---|---|---|---|
| 101 | 4-Cl-C6H4- | $-(CH_2)_3-$ | α | $CH_3$ |
| 102 | 4-Cl-C6H4- | $-(CH_2)_3-$ | β | $CH_3$ |
| 103 | 3-CF3-C6H4- | $-(CH_2)_3-$ | α | H |
| 104 | 3-CF3-C6H4- | $-(CH_2)_3-$ | β | H |
| 105 | $-CH_2$-(3-F-C6H4) | $-(CH_2)_3-$ | α | H |
| 106 | $-CH_2$-(3-F-C6H4) | $-(CH_2)_3-$ | α | $CH_3$ |
| 107 | $-CH_2$-(2-Cl-C6H4) | $-(CH_2)_3-$ | α | H |
| 108 | $-CH_2$-(4-Cl-C6H4) | $-(CH_2)_3-$ | α | H |
| 109 | $-CH_2$-(4-Cl-C6H4) | $-(CH_2)_3-$ | β | H |
| 110 | $-CH_2$-(4-Cl-C6H4) | $-(CH_2)_3-$ | α | $CH_3$ |
| 111 | $-CH_2$-(4-Cl-C6H4) | $-(CH_2)_3-$ | β | $CH_3$ |
| 112 | $-(CH_2)_2$-(3,4-(OCH3)2-C6H3) | $-(CH_2)_3-$ | α | H |
| 113 | $-(CH_2)_2$-(2,4,6-(CH3)3-C6H2) | $-(CH_2)_3-$ | α | H |
| 114 | $-CH(C_4H_9)-CH_2-\phi$ | $-(CH_2)_3-$ | α | H |
| 115 | $-CH(C_4H_9)-CH_2-\phi$ | $-(CH_2)_3-$ | β | H |

Table IV

Final PGE Compound (Formula LXXVI)

| Ex. | Q | A | M | $R_3$ |
|---|---|---|---|---|
| 116 | $-(CH_2)_3-\phi$ | $-CH_2-$ | α | H |
| 117 | $-(CH_2)_3-\phi$ | $-CH_2-$ | β | H |
| 118 | $-(CH_2)_3-\phi$ | $-CH_2-$ | α | $CH_3$ |
| 119 | $-(CH_2)_3-\phi$ | $-CH_2-$ | β | $CH_3$ |
| 120 | $-(CH_2)_3-\phi$ | $-CH_2-$ | α | $C_2H_5$ |
| 121 | $-(CH_2)_3-\phi$ | $-CH_2-$ | β | $C_2H_5$ |
| 122 | $-CH_2-\phi$ | $-CH_2-$ | α | H |
| 123 | $-CH_2-\phi$ | $-CH_2-$ | β | H |
| 124 | $-CH_2-\phi$ | $-CH_2-$ | α | $CH_3$ |
| 125 | $-CH_2-\phi$ | $-CH_2-$ | β | $CH_3$ |
| 126 | $-CH_2-\phi$ | $-CH_2-$ | α | $C_2H_5$ |
| 127 | $-CH_2-\phi$ | $-CH_2-$ | β | $C_2H_5$ |
| 128 | $-C(CH_3)_2-CH_2-\phi$ | $-(CH_2)_3-$ | α | H |
| 129 | $-C(CH_3)_2-CH_2-\phi$ | $-(CH_2)_3-$ | β | H |
| 130 | $-C(CH_3)_2-CH_2-\phi$ | $-(CH_2)_3-$ | α | $CH_3$ |
| 131 | $-C(CH_3)_2-CH_2-\phi$ | $-(CH_2)_3-$ | β | $CH_3$ |
| 132 | $-(CH_2)_4-\phi$ | $-(CH_2)_3-$ | α | H |
| 133 | $-(CH_2)_4-\phi$ | $-(CH_2)_3-$ | β | H |
| 134 | $-(CH_2)_4-\phi$ | $-(CH_2)_3-$ | α | $CH_3$ |
| 135 | $-(CH_2)_4-\phi$ | $-(CH_2)_3-$ | β | $CH_3$ |
| 136 | $-(CH_2)_5-\phi$ | $-CH_2-$ | α | H |
| 137 | $-(CH_2)_5-\phi$ | $-(CH_2)_3-$ | α | H |
| 138 | $-(CH_2)_7-\phi$ | $-CH_2-$ | α | H |
| 139 | $-(CH_2)_7\phi$ | $-(CH_2)_3-$ | α | H |
| 140 | $-(CH_2)_7\phi$ | $-(CH_2)_5-$ | α | H |
| 141 | $-CHF-(CH_2)_3\phi$ | $-CH_2-$ | α | H |
| 142 | $-CHF-(CH_2)_3\phi$ | $-(CH_2)_3-$ | α | H |
| 143 | $-CHF-(CH_2)_3\phi$ | $-(CH_2)_3-$ | β | H |
| 144 | $-CHF-(CH_2)_3\phi$ | $-(CH_2)_3-$ | α | $CH_3$ |
| 145 | $-CHF-(CH_2)_3\phi$ | $-(CH_2)_3-$ | β | $CH_3$ |
| 146 | $-CHF-(CH_2)_3\phi$ | $-(CH_2)_5-$ | α | H |
| 147 | $-CF_2-(CH_2)_2\phi$ | $-CH_2-$ | α | H |
| 148 | $-CF_2-(CH_2)_2\phi$ | $-(CH_2)_3-$ | α | H |
| 149 | $-CF_2-(CH_2)_2\phi$ | $-(CH_2)_3-$ | β | H |
| 150 | $-CF_2-(CH_2)_2\phi$ | $-(CH_2)_3-$ | α | $CH_3$ |
| 151 | $-CF_2-(CH_2)_2\phi$ | $-(CH_2)_3-$ | β | $CH_3$ |
| 152 | $-CF_2-(CH_2)_2\phi$ | $-(CH_2)_3-$ | α | $C_2H_5$ |
| 153 | $-CF_2-(CH_2)_2\phi$ | $-(CH_2)_3-$ | β | $C_2H_5$ |
| 154 | $-CF_2-(CH_2)_4-\phi$ | $-CH_2-$ | α | H |
| 155 | $-CF_2-(CH_2)_4\phi$ | $-(CH_2)_3-$ | α | H |

Table IV-continued

Final PGE Compound (Formula LXXVI)

| Ex. | Q | A | M | $R_3$ |
|---|---|---|---|---|
| 156 | phenyl-o-CH₃ | —(CH₂)₃— | α | H |
| 157 | phenyl-o-CH₃ | —(CH₂)₃— | β | H |
| 158 | phenyl-o-CH₃ | —(CH₂)₃— | α | CH₃ |
| 159 | phenyl-o-CH₃ | —(CH₂)₃— | β | CH₃ |
| 160 | phenyl-p-Cl | —(CH₂)₃— | α | H |
| 161 | phenyl-p-Cl | —(CH₂)₃— | β | H |
| 162 | phenyl-p-Cl | —(CH₂)₃— | α | CH₃ |
| 163 | phenyl-p-Cl | —(CH₂)₃— | β | CH₃ |
| 164 | phenyl-o-CF₃ | —(CH₂)₃— | α | H |
| 165 | phenyl-o-CF₃ | —(CH₂)₃— | β | H |
| 166 | —CH₂-phenyl-o-F | —(CH₂)₃— | α | H |
| 167 | —CH₂-phenyl-o-F | —(CH₂)₃— | α | CH₃ |
| 168 | —CH₂-phenyl-o-Cl | —(CH₂)₃— | α | H |
| 169 | —CH₂-phenyl-p-Cl | —(CH₂)₃— | α | H |
| 170 | —CH₂-phenyl-p-Cl | —(CH₂)₃— | β | H |
| 171 | —CH₂-phenyl-p-Cl | —(CH₂)₃— | α | CH₃ |
| 172 | —CH₂-phenyl-p-Cl | —(CH₂)₃— | β | CH₃ |
| 173 | —(CH₂)₂-phenyl-(OCH₃)₂ | —(CH₂)₃— | α | H |
| 174 | —(CH₂)₂-phenyl-(CH₃)₃ | —(CH₂)₃— | α | H |
| 175 | —CH(C₄H₉)—CH₂—φ | —(CH₂)₃— | α | H |
| 176 | —CH(C₄H₉)—CH₂—φ | —(CH₂)₃— | β | H |

Following the procedure of Examples 55 – 176, but replacing the optically active compound of the Formula LVIII of each example by a racemic mixture of that compound and the mirror image thereof, there is obtained the corresponding racemic mixture for each Example 55 – 176.

PREPARATION 8

3α-Benzoyloxy-2β-carboxaldehyde-5α-hydroxy-1α-cyclopentaneacetic Acid γ-Lactone (Formula LXXVII; $R_{51}$ is phenyl)

Refer to Chart L. 1. To a mixture of laevorotatory (—) 3α-hydroxy-5α-hydroxy-4-iodo-2β-methoxy-methyl-1α-cyclopentaneacetic acid γ-lactone (E. J. Corey et al., J. Am. Chem. Soc. 92, 397 (1970), 75 g.) in 135 ml. of dry pyridine under a nitrogen atmosphere is added 30.4 ml. of benzoyl chloride with cooling to maintain the temperature at about 20°–40°. Stirring is continued for an additional 30 min. About 250 ml. of toluene is added and the mixture concentrated under reduced pressure. The residue is dissolved in one liter of ethyl acetate, washed with 10% sulfuric acid, brine, aqueous saturated sodium bicarbonate, and brine. The ethyl acetate solution is dried over sodium sulfate and concentrated under reduced pressure to yield an oil, 95 g. Crystallization of the oil yields the corresponding 3α-benzoyloxy compound, m.p. 84°–86° C.; $[\alpha]_D$ + 7° (CHCl₃); infrared spectral absorptions at 1768, 1722, 1600, 1570, 1490, 1275, 1265, 1180, 1125, 1090, 1060, 1030, and 710 cm⁻¹; and NMR (nuclear magnetic resonance) peaks at 2.1–3.45; 3.3, 3.58, 4.38, 5.12, 5.51, 7.18–7.58, and 7.83–8.05 δ.

2. The iodo group is removed as follows. To a solution of the above benzoyloxy compound (60 g.) in 240 ml. of dry benzene is added 2,2'-azobis-(2-methylpropionitrile) (approximately 60 mg.) The mixture is cooled to 15° and to it is added a solution of 75 g. tributyltin hydride in 600 ml. of ether, with stirring, at such a rate as to maintain continuous reaction at about 25°. When the reaction is complete as shown by TLC, the mixture is concentrated under reduced pressure to an oil. The oil is mixed with 600 ml. of Skellysolve B and 600 ml. of water and stirred for 30 min. The water layer, containing the product, is separated, then combined with 450 ml. of ethyl acetate and enough solid sodium chloride to saturate the aqueous phase. The ethyl acetate layer, now containing the product, is separated, dried over magnesium sulfate, and concentrated under reduced pressure to an oil, 39 g. of the iodine-free compound. An analytical sample gives [α] -99° (CHCl$_3$); infrared spectral absorptions at 1775, 1715, 1600, 1585, 1490, 1315, 1275, 1180, 1110, 1070, 1055, 1025, and 715 cm$^{-1}$; NMR peaks at 2.5–3.0, 3.25, 3.34, 4.84–5.17, 5.17–5.4, 7.1–7.5, and 7.8–8.05 δ; and mass spectral peaks at 290, 168, 105 and 77.

3. The 2β- methoxymethyl compound is changed to a hydroxymethyl compound as follows. To a cold (0.5°) solution of the above iodine-free methoxy-methyl lactone (20 g.) in 320 ml. of dichloromethane under nitrogen is added a solution of 24.8 ml. of boron tribromide in 320 ml. of dichloromethane, drop-wise with vigorous stirring over a period of 50 min. at 0°–5°. Stirring and cooling are continued for 1 hr. When the reaction is complete, as shown by TLC, there is cautiously added a solution of sodium carbonate (78 g. monohydrate) in 200 ml. of water. The mixture is stirred at 0°–5° for 10–15 min., saturated with sodium chloride, and the ethyl acetate layer separated. Additional ethyl acetate extractions of the water layer are combined with the main ethyl acetate solution. The combined solutions are rinsed with brine, dried over sodium sulfate and concentrated under reduced pressure to an oil, 18.1 g of the 2β-hydroxymethyl compound. An analytical sample has m.p. 116–118° C.; [α]$_D$ –80° (CHCl$_3$); infrared spectral absorptions at 3460, 1735, 1708, 1600, 1580, 1490, 1325, 1315, 1280, 1205, 1115, 1090, 1070, 1035, 1025, 730, and 720; and NMR peaks at 2.1–3.0, 3.58, 4.83–5.12, 5.2–5.45, 7.15–7.55, and 7.8–8.0 δ.

d. The title 2β- carboxaldehyde compound is prepared as follows. To a mixture of 150 ml. of dry dichloromethane and Collins' reagent (J. C. Collins et al., Tetrahedron Lett. 3363 (1968), 28 g.) at about 10° under nitrogen is added, with vigorous stirring, a cold (10°) solution of the hydroxymethyl compound above (5.0 g.) in 150 ml. of dichloromethane. After 5 min. additional stirring, about 100 ml. of dry benzene is added, the mixture is filtered, and the solution is concentrated under reduced pressure. The volume is brought to about 150 ml. with benzene. The solution of the title compound is used directly. In a repetitive experiment the Collins' reagent is prepared in situ with comparable results.

Following the procedure of Preparation 8, but replacing that optically active formula-XXIV iodolactone with the racemic compound of that formula and the mirror image thereof (see E. J. Corey et al., J. Am. Chem. Soc. 91, 5675 (1969)) there is obtained the racemic compound corresponding to the Formula LXXVII.

PREPARATION 9

Dimethyl 2-Oxo-4-phenylbutylphosphonate

To a solution of dimethyl methylphosphonate (115.5 g.) in tetrahydrofuran (2.1 l.) at −65°, there is added 660 ml. of a 1.6 M solution of n-butyl lithium in hexane, and then there is added a solution of ethylhydrocinnamate (93.5 g.) in tetrahydrofuran (225 ml.). The mixture is stirred at −65° for 2 hrs. and then stirring is continued at 25° for 16 hrs. Acetic acid (70 ml.) is added, the solution is concentrated under reduced pressure and the residue is partitioned between methylene chloride and water. The organic layer is dried, concentrated, and distilled at 2 mm. to give 121.5 g. of the title compound; b.p. 184–195; mass spectrum 256 (M$^+$).

PREPARATION 10

Dimethyl 3,3-dimethyl-2-oxo-4 phenylbutylphosphonate

1. To a solution of diisopropylamine (101.2 g.) in tetrahydrofuran (125 ml.) under nitrogen at 0°, there is added a solution of n-butyl lithium in hexane (625 ml.) and then isobutyric acid (44 g.). The mixture is stirred at 0° for 90 min., then cooled to −15° and benzyl chloride (60 ml.) is added while maintaining the temperature below −5°. The mixture is stirred at 25° for 4 hrs., then diluted with ether and washed with cold dilute hydrochloric acid. The organic layer is washed with brine, dried, concentrated and distilled to give 48 g. of 2,2-dimethyl-3-phenylpropionic acid.

2. The product of part 1 (48 g.) and thionyl chloride (82 g.) is heated for 2 hrs. then the mixture is concentrated, benzene (50 ml.) is added and the mixture is concentrated and distilled to give 48.2 g. of 2,2-dimethyl-3-phenylpropionyl chloride.

3. To a solution of dimethyl methylphosphonate (63 g.) in tetrahydrofuran (600 ml.) under nitrogen at −75°, there is added 312 ml. of 1.6 M n-butyl lithium in hexane, while maintaining the temperature below −55°. A solution of 2,2-dimethyl-3-phenylpropionyl chloride (part 2, 48.2 g.) in tetrahydrofuran is added while maintaining the temperature below −60°. The mixture is stirred at that temperature for 2 hrs. and then the temperature is allowed to rise to about 25° C. and the mixture is stirred at that temperature for 16 hrs. Acetic acid (20 ml.) is added, the mixture is concentrated, the residue is shaken with a mixture of diethyl ether-methylene chloride (3:1, v/v) and cold dilute sodium bicarbonate solution. The organic layer is separated, washed with brine, dried and concentrated. The residue is crystallized from diethylether to give the title compound, 62 g.; m.p. 48°–51°; NMR peaks at 7.2, 3.83 and 3.64, 3.28 and 2.9, 2.8 and 1.13 δ.

The following Examples describe the preparation of PG compounds by the process illustrated in Chart L.

EXAMPLE 177

2-Hydroxy-4-benzoxy-5-(1'-trans-3'-oxo-5'-phenyl-pentenyl)-cyclopentanyl acetic acid γ-lactone
(Formula LXXVIII; R$_{51}$ is phenyl, Q is —(CH$_2$)$_2$C$_6$H$_5$)

Refer to Chart L. A benzene solution (60 ml.) of the Formula LXXVII compound (Preparation 8) is added to a solution of the anion of dimethyl 2-oxo-4-phenyl-butylphosphonate prepared from that compound (Preparation 9, 14.28 g.) and sodium hydride (2.7 g.) in 250 ml. of tetrahydrofuran. The resulting reaction mixture is stirred for 2 hrs. at about 25°, then acidified with acetic acid (1.5 ml.) and concentrated under reduced pressure. The residue is diluted with ethyl acetate, washed with brine, dried, and concentrated and then chromatographed on silica gel, eluting with ethyl acetate-SSB (1:1) to yield 2.73 g. of the title compound, having m.p. 118°–119.5° and giving [α] −103° (chf, c=0.9826) and λ$_{Max}^{EtOH}$ 229m (26700), 264mμ(1200), 268mμ(1150), 274mμ(1100) and 281mμ(886).

Following the procedure of Example 177, but replacing the optically active Formula LXXVII compound with a racemic mixture of that compound and the mirror image thereof, there is obtained the corresponding racemic mixture.

EXAMPLE 178

2-Hydroxy-4-benzoxy-5(1'-trans-3'α-hydroxy-5'-phenyl-pentenyl)-cyclopentanyl acetic acid γ-lactone (Formula LXXIX; R$_{51}$ is phenyl, Q is -(CH$_2$)$_2$C$_6$H$_5$ M is

and the corresponding 3'β isomer (M is

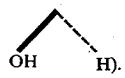).

Refer to Chart L. A mixture of sodium borohydride (3 g.) and zinc chloride (13.6 g.) in diglyme (120 ml.) is stirred at about 25° for 2 hrs. and then is cooled to −10°. A solution of the title compound (8.1 g.) of Example 177 in diglyme (45 ml.) is added and the reaction mixture is stirred at 0° for 2 hrs. and then at about 25° for 1 hr. Water (19.5 ml.) and ethyl acetate are added, the solids filtered off, the liquid washed with brine, dried and concentrated. The residue is chromatographed over silica gel, eluting with ethyl acetate-SSB(2:1). From the various fractions there is obtained the 3'α-hydroxy title compound (3.4 g.), the 3'β-hydroxy compound (2.75 g.) and a mixture of those compounds (0.49 g.). The 3'α and 3'β hydroxy compounds crystallize on standing. The 3'α-hydroxy compound, recrystallized from ethyl acetate-SSB, to give an analytical sample, has a m.p. 88°–90°.

Following the procedure of Example 178, but replacing the optically active Formula LXXVIII compound with a racemic mixture of that compound and the mirror image thereof, there is obtained the corresponding racemic mixture.

EXAMPLE 179

2,4-Dihydroxy-5-(1'-trans-3'α-hydroxy-5-phenyl-pentenyl)cyclopentyl acetaldehyde γ-lactol, 4,3'-bis(tetrahydropyranyl)Ether (Formula LXXII: Q is -(CH$_2$)$_2$C$_6$H$_5$, J is tetrahydropyranyl, M' is

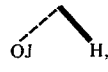

~ is alpha or beta)

Refer to Chart L. 1. A solution of the Formula LXXIX 3'α-hydroxy compound (Example 178, 3.3 g.) and potassium carbonate (1.11 g.) in methanol (38 ml.) is stirred at about 25° for 80 min. and then chloroform is added and the solids are removed by filtration. The filtrate is concentrated under reduced pressure. The residue is diluted with methylene chloride, washed with brine, dried and concentrated. The oily residue is triturated with three portions of Skellysolve B and concentrated to yield the oily 2,4-dihydroxy-5-(1'-trans-3'α-hydroxy-5-phenyl-pentenyl)cyclopentanyl acetic acid γ-lactone (2.02 g.), which crystallizes on standing. An analytical sample recrystallized from ethyl acetate-SSB has m.p. 65°–67° C.

2. The compound from part 1 above (1.985 g.) is converted to the corresponding bis(tetrahydropyranyl) ether by reaction with dihydropyran (5.95 ml.) in methylene chloride (45 ml.) in the presence of pyridine hydrochloride (33 mg.) at about 25° for 25 min. The reaction mixture is washed with aqueous potassium bicarbonate solution, dried and concentrated to yield oily Formula LXXI compound, 2,4-dihydroxy-5(1'-trans-3'α-hydroxy-5-phenyl-pentenyl) cyclopentyl acetic acid γ-lactone,-4,3'-bis(tetrahydropyranyl) ether (4.4 g.).

3. The title compound is prepared by adding diisobutylaluminium hydride (3.9 ml.) dropwise to a solution of the Formula LXXI compound from part 2 (4.4 g.) in toluene (45 ml.) cooled to −78°. Stirring is continued for 30 min. and then a solution of water (9 ml.) in tetrahydrofuran (17 ml.) is slowly added. The cooling bath is removed and the reaction mixture is stirred for 1 hr. at about 25°. The reaction mixture is filtered and the filtrate is washed with brine, dried and concentrated to give the oily title compound (4.39 g.).

Following the procedure of Example 178, but replacing the Formula LXXIX compound with a racemic mixture of that compound and the mirror image thereof, there is obtained the corresponding racemic mixture.

EXAMPLE 180

17-Phenyl-18,19,20-trinor-PGF$_{2α}$ ,4,3'-bis(tetrahydropyranyl) Ether (Formula LXXIII; A is -(CH$_2$)$_3$-, R$_2$ is H, Q is -(CH$_2$)$_2$C$_6$H$_5$, J is tetrahydropyranyl and M' is

Refer to Chart L. 4-Carboxybutyltriphenylphosphonium bromide (E. J. Corey et al., J. Am.Chem. Soc. 91,5677 (1969) (16.45 g.) is added to a solution of sodio dimethylsulfinylcarbanide prepared from sodium hydride (57%, 3.15 g.) in dimethylsulfoxide (75 ml.). To this reagent is added the Formula LXXII lactol of Example 179 dissolved in dimethylsulfoxide (10 ml.) The mixture is stirred at about 25° for 2 hrs. Then diluted with benzene. A solution of potassium hydrogen sulfate (10.1 g.) in water (45 ml.) is added. The organic layer is separated, washed with water, dried and concentrated under reduced pressure to give an oily residue (9.7 g.). The residue is chromatographed on silica gel, eluting with chloroform-methanol (7:1) combining those fractions shown by TLC to contain the product free of starting material and impurities. Concentration under reduced pressure give the title compound (3.26 g.) as an oil. This material is used in the subsequent Example without purification.

Following the procedure of Example 180 but replacing that Formula LXXII compound with a racemic mixture of that compound and the mirror image thereof, there is obtained the corresponding racemic mixture.

EXAMPLE 181

17-Phenyl-18,19,20-trinor-PGF$_{2α}$ (Formula LXXIV; A is -(CH$_2$)$_3$-, R$_2$ is H, Q is -(CH$_2$)$_2$C$_6$H$_5$ and M is

Refer to Chart L. A solution of the Formula LXXIII compound (1.27 g.) of Example 180 in tetrahydrofuran (5 ml.) and 50 ml. of 67% acetic acid is heated at about 45° for 2 hrs. Water (34 ml.) is added, tetrahydrofuran is evaporated under reduced pressure and the remaining aqueous solution is lyophilized. The solid residue is dissolved in toluene and then the toluene is removed, together with traces of acetic acid, by distillation under vacuum. The residue is chromatographed on silica gel, eluting with chloroform-methanol solvent. Those fractions shown by TLC to contain the title compound free of starting material and impurities are combined and concentrated to yield the title compound (506 mg.)

Following the procedure of Example 181, but replacing that Formula LXXIII compound with a racemic mixture of that compound and the mirror image thereof, there is obtained the corresponding racemic mixture.

EXAMPLE 182

17-Phenyl-18,19,20-trinor-PGE$_2$ (Formula LXXVI; A is -(CH$_2$)$_3$-, R$_2$ is H, Q is -(CH$_2$)$_2$C$_6$H$_5$ and M is 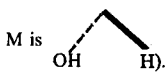

Refer to Chart L. 1. To a solution of the Formula LXXIII compound (2 g.) of Example 180 in acetone (30 ml.) cooled in an ice-methanol bath, there is added Jones' reagent (2,81 ml.). 2-Propanol (2 ml.) and water (80 ml.) are added and the solution is extracted with methylene chloride. The extract is washed with brine, dried and concentrated to yield a residue (1.45 g.) of PGE$_2$ bis(tetrahydropyranyl) ether (Formula LXXV).

2. The residue (1.45 g.) of part 1 is dissolved in tetrahydrofuran (6 ml.) and 60 ml. of 67% aqueous acetic acid and the solution is heated at 41° for 2 hrs. The solution is concentrated under reduced pressure and is chromatographed on silica gel, eluting with chloroform-methanol (10:1). Those fractions shown by TLC to contain the title compound free of starting material and impurities are combined and concentrated to yield the title compound (213 mg.).

Following the procedure for Example 182, but replacing that Formula LXXIII compound with a racemic mixture of that compound and the mirror image thereof, there is obtained the corresponding racemic mixture.

The foregoing Example 177 employs the phosphonate of Preparation 9 for transforming the Formula LXXVII compound to the Formula LXXVIII compound. This transformation can also be carried out using phosphoranes of the formula

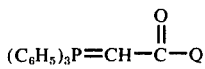

Preparations of representative phosphoranes are as follows:

PREPARATION 11

2-Oxo-3-phenylpropyltriphenylphosphorane

1. A solution of triphenylphosphine (33.5 g.) and

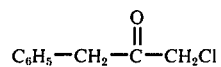

(Org. Syn. Coll. Vol. 3, p.119–21.5 g.) in toluene (100 ml.) is heated under reflux for 1 hr. The solution is cooled and filtered and there is obtained 2-oxo-3-phenylpropyltriphenylphosphonium chloride (33.8 g.); m.p. 206°–208° C.

2. To a solution of the product of part 1 (11.8 g.) in methanol (27 ml.) there is added sodium hydroxide (22 ml. of 5% solution). The crystals are separated and recrystallized to give 10.85 g. of the title compound; m.p. 99°–101° C.

Employing the title compound in the procedures of Examples 177, 178, 179, 180, 181 and 182 gives 16-Phenyl-17,18,19,20-tetranor-PGF$_{2\alpha}$ and racemic compound thereof, and 16-Phenyl-17,18,19,20-tetranor-PGE$_2$ and racemic compound thereof.

PREPARATION 12

2-Oxo-4-p-fluorophenylbutyltriphenylphosphorane

1. To a stirred mixture of 16.8 g. of magnesium turnings, 100 ml. of diethyl ether, and a small crystal of I$_2$, under nitrogen, is added about 13 ml. of a solution of 100 g. of 4-fluorobenzyl chloride in 300 ml. of diethyl ether. The mixture is heated until the reaction is initiated and then is cooled by an ice bath. The remainder of the 4-fluorobenzyl chloride solution is added during 30 minutes at such a rate as to maintain a vigorous reaction. The mixture is heated under reflux for 2 hrs., cooled to room temperature, and filtered to remove unreacted magnesium.

The solution is added to a stirred solution of 58.3 g. of epichlorohydrin in 100 ml. of diethyl ether, under nitrogen, during 1.5 hrs. at such a rate as to maintain a gentle reflux. The mixture is allowed to stand for 16 hrs. and then is poured on ice and acidified with dilute sulfuric acid (40 ml. of conc. H$_2$SO$_4$ in 500 ml. of H$_2$O). The layers are separated. The ether layer is washed with dilute aqueous sodium carbonate solution and water and dried. Evaporation of the ether leaves 120.3 g. of colorless oil. The oil is distilled at 0.2 mm giving 57.5 g. of 1-chloro-4-p-fluorophenyl-2-butanol as a colorless oil. The infrared spectrum shows absorptions at 3560, 3400, 1600, 1510, 1495, 1225, 1160, 1060, 830, and 760 cm$^{-1}$. NMR peaks are observed at 1.4–2.1, 2.4–3.1, 3.4–4.0, and 6.8–7.3 δ.

2. To a stirred solution of 57.5 g. of 1-chloro-4-p-fluorophenyl-2-butanol of part 1 in 200 ml. of acetone, cooled in an ice-methanol bath, is added 106 ml. of Jones' reagent during 30 minutes. The temperature rises to 10° and stirring with cooling is continued for 1.5 hrs. Then 106 ml. of isopropanol is added and the stirring is continued with cooling for 20 minutes. The mixture is poured into 700 ml. of water and extracted with methylene chloride. The extract is washed with brine, dried and concentrated to give 54.9 g. of dark oil. The oil is distilled at 0.2 mm. giving 44.5 g. of 1-chloro-4-p-fluorophenyl-2-butanone as a colorless oil; b.p. 92°–95° C. NMR peaks are observed at 2.95, 4.05, and 6.9–7.35 δ.

3. A mixture of 44.5 g. of 1-chloro-4-p-fluorophenyl-2-butanone of part 2, 58.2 g. of triphenylphosphine, and 200 ml. of acetonitrile is stirred and heated under reflux for 18 hrs. Then 150 ml. of acetonitrile is distilled from the mixture. After cooling the mixture to room temperature 200 ml. of benzene is added. Upon cooling for 16 hrs. at 5° a solid separates. The solid is collected by filtration giving 29.75 g. of white prisms of (2-Oxo-4-p-fluorophenylbutyl)triphenylphosphonium chloride; m.p. 194°–196°. The infrared spectrum show absorptions at 3280, 2800, 2740, 2690, 2570, 1705, 1600, 1590, 1510, 1225, 1115, 755, 725, and 695 cm$^{-1}$. NMR peaks are observed at 2.5–3.5, 5.9–6.2, 6.8–8.1 δ.

4. To a solution of 29.25 g. of (2-oxo-4-p-fluorophenylbutyl)-triphenylphosphonium chloride of part 3, in 250 ml. of warm water is added 80 ml. of 1N sodium hydroxide solution. An oil separates which solidifies. The solid is collected by filtration and dissolved in methylene chloride. The solution is dried and then concentrated on a steam bath. Skellysolve B is added to the boiling solution. Cooling gives cream prisms of the title compound (25.85 g.); m.p. 123°–125°. The infrared spectrum shows absorptions at 3490, 3540, 3240, 1605, 1590, 1575, 1550, 1525, 1510, 1485, 1440, 1390, 1220, 1105, 875, 860, 755, 720, and 700 cm$^{-1}$. NMR peaks are observed at 2.6–3.0, 6.9–7.4 and 7.4–7.8 δ.

Employing the title compound in the procedures of Examples 177, 178, 179, 180, 181 and 182 gives 17-p-fluorophenyl-18,19,20-trinor-PGF$_2\alpha$ and racemic compound thereof, and 17-p-fluorophenyl-18,19,20-trinor-PGE$_2$ and racemic compound thereof.

Example 183

Following the procedures of Preparations 9 and 10, but replacing the phenyl-substituted aliphatic acid esters used therein, e.g., ethylhydrocinnamate of Preparation 9, by various phenyl-substituted aliphatic acid esters, there are obtained the corresponding phosphonates of the formula

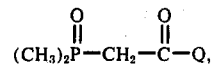

wherein Q is as defined above.

Following the procedures of Preparations 11 and 12, but replacing the ketone compound used therein, e.g.

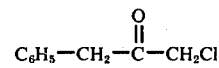

of Preparation 11, by various phenyl-substituted ketone compounds, there are obtained the corresponding phosphoranes of the formula

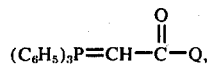

wherein Q is as defined above.

Following the procedures of Examples 177, 178, 179, 180, 181, and 182 each of the optically active compounds of the Formula LXXVII is transformed to compounds of the Formulas LXXIV and LXXVI, using (a) the various phosphonates or phosphoranes prepared as described above and (b) ω-carboxy triphenylphosphonium halides prepared as described above.

Tables V and VI below list the Formulas LXXIV and LXXVI PG compounds that are obtained.

Table V

Final PGF Compound
(Formula LXXIV)

| Example | Q | A | M | R$_3$ |
|---|---|---|---|---|
| 183 | —(CH$_2$)$_2\phi$ | —CH$_2$—CH$_2$—CHF— | α | H |
| 184 | —(CH$_2$)$_2\phi$ | —CH$_2$—CH$_2$—CHF— | β | H |
| 185 | —(CH$_2$)$_2\phi$ | —CH$_2$—CH$_2$—CHF— | α | CH$_3$ |
| 186 | —(CH$_2$)$_2\phi$ | —CH$_2$—CH$_2$—CHF— | β | CH$_3$ |
| 187 | —(CH$_2$)$_2\phi$ | —CH$_2$—CH$_2$—CHF— | α | C$_2$H$_5$ |
| 188 | —(CH$_2$)$_2\phi$ | —CH$_2$—CH$_2$—CHF— | β | C$_2$H$_5$ |
| 189 | —(CH$_2$)$_2\phi$ | —CH$_2$—CHF—CF$_2$— | α | H |
| 190 | —(CH$_2$)$_2\phi$ | —CH$_2$—CHF—CF$_2$— | β | H |
| 191 | —(CH$_2$)$_2\phi$ | —CH$_2$—CHF—CF$_2$ | α | CH$_3$ |
| 192 | —(CH$_2$)$_2\phi$ | —CH$_2$—CHF—CF$_2$ | β | CH$_3$ |
| 193 | —(CH$_2$)$_2\phi$ | —CH$_2$—CHF—CF$_2$ | α | C$_2$H$_5$ |
| 194 | —(CH$_2$)$_2\phi$ | —CH$_2$—CHF—CF$_2$ | β | C$_2$H$_5$ |
| 195 | —CH$_2\phi$ | —CH$_2$—CF$_2$— | α | H |

Table V-continued

Final PGF Compound
(Formula LXXIV)

| Example | Q | A | M | R₃ |
|---|---|---|---|---|
| 196 | —(CH₂)₂—⌬—F | —CF₂—CH₂— | α | H |
| 197 | —(CH₂)₃φ | —CH₂—CF₂—CHF | α | H |
| 198 | —C(CH₃)₂—CH₂ | —CH₂—CF₂—CF₂ | α | H |
| 199 | —(CH₂)₂φ | —CH₂—CH₂—CH(CH₃)— | α | H |
| 200 | —(CH₂)₂φ | —CH₂—CH₂—CH(CH₃)— | β | H |
| 201 | —(CH₂)₂φ | —CH₂—CH₂—CH(CH₃)— | α | CH₃ |
| 202 | —(CH₂)₂φ | —CH₂—CH₂—CH(CH₃)— | β | CH₃ |
| 203 | —(CH₂)₂φ | —CH₂—C(CH₃)₂—CH₂— | α | H |
| 204 | —(CH₂)₂φ | —CH₂—CH(CH₃)—CHF— | α | H |
| 205 | —(CH₂)₂φ | —CH₂CH(C₂H₅)—CH₂— | α | H |
| 206 | —CH₂φ | —CH₂—CH(CH₃)—CH₂— | α | H |
| 207 | —(CH₂)₂φ | —CH₂—CH(C₂H₅)—CHF— | α | H |
| 208 | —(CH₂)₂φ | —CH₂—CH(C₃H₈)—CH₂— | α | H |
| 209 | —(CH₂)₂φ | —CH₂—CH₂—CH(C₄H₉)— | α | H |
| 210 | —CH₂φ | —(CH₂)₅— | α | H |
| 211 | —CH₂φ | —(CH₂)₅— | β | H |
| 212 | —CH₂φ | —(CH₂)₅— | α | CH₃ |
| 213 | —CH₂φ | —(CH₂)₅— | β | CH₃ |
| 214 | —(CH₂)₂—⌬—Cl | —CH(CH₃)— | α | H |
| 215 | —(CH₂)₃—⌬—F | —CH₂—CH(CH₃)—CH₂— | α | H |
| 216 | —(CH₂)₂—⌬(F) | —(CH₂)₃— | α | H |
| 217 | —C(CH₃)₂—CH₂φ | —CH₂—CH₂—CH(C₃H₇)— | α | H |
| 218 | —C(CH₃)₂—CH₂φ | —CH₂—CH₂—CH(C₃H₇)— | β | H |
| 219 | —C(CH₃)₂—CH₂φ | —CH₂—CH₂—CH(C₃H₇) | α | CH₃ |
| 220 | —(CH₂)₂—⌬—F | —CH₂—CH₂—CF(CH₃)— | α | H |
| 221 | —(CH₂)₂φ | —CH₂—CHF—CH₂— | α | H |
| 222 | —(CH₂)₂φ | —CH₂—CHF—CH₂— | α | CH₃ |
| 223 | —(CH₂)₂φ | —(CH₂)₃—CF₂— | α | H |
| 224 | —(CH₂)₂φ | —(CH₂)₄—CF₂—CF₂— | α | H |
| 225 | —(CH₂)₂φ | —(CH₂)₃—CH₂—C(CH₃)₂— | α | H |

Table VI

Final PGE Compound
(Formula LXXVI)

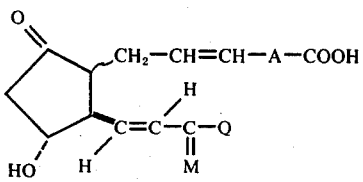

| Ex. | Q | A | M | $R_3$ |
|---|---|---|---|---|
| 226 | $-(CH_2)_2\phi$ | $-CH_2-CH_2-CHF-$ | $\alpha$ | H |
| 227 | $-(CH_2)_2\phi$ | $-CH_2-CH_2-CHF-$ | $\beta$ | H |
| 228 | $-(CH_2)_2\phi$ | $-CH_2-CH_2-CHF-$ | $\alpha$ | $CH_3$ |
| 229 | $-(CH_2)_2\phi$ | $-CH_2-CH_2-CHF-$ | $\beta$ | $CH_3$ |
| 230 | $-(CH_2)_2\phi$ | $-CH_2-CH_2-CHF-$ | $\alpha$ | $C_2H_5$ |
| 231 | $-(CH_2)_2\phi$ | $-CH_2-CH_2-CHF-$ | $\beta$ | $C_2H_5$ |
| 232 | $-(CH_2)_2\phi$ | $-CH_2-CHF-CF_2-$ | $\alpha$ | H |
| 233 | $-(CH_2)_2\phi$ | $-CH_2-CHF-CF_2-$ | $\beta$ | H |
| 234 | $-(CH_2)_2\phi$ | $-CH_2-CHF-CF_2$ | $\alpha$ | $CH_3$ |
| 235 | $-(CH_2)_2\phi$ | $-CH_2-CHF-CF_2$ | $\beta$ | $CH_3$ |
| 236 | $-(CH_2)_2\phi$ | $-CH_2-CHF-CF_2$ | $\alpha$ | $C_2H_5$ |
| 237 | $-(CH_2)_2\phi$ | $-CH_2-CHF-CF_2$ | $\beta$ | $C_2H_5$ |
| 238 | $-CH_2\phi$ | $-CH_2-CF_2-$ | $\alpha$ | H |
| 239 | $-(CH_2)_2\text{-}C_6H_4\text{-}F$ | $-CF_2-CH_2-$ | $\beta$ | H |
| 240 | $-(CH_2)_3\phi$ | $-CH_2-CF_2-CHF$ | $\alpha$ | H |
| 241 | $-C(CH_3)_2-CH_2$ | $-CH_2-CF_2-CF_2$ | $\alpha$ | H |
| 242 | $-(CH_2)_2\phi$ | $-CH_2-CH_2-CH(CH_3)-$ | $\alpha$ | H |
| 243 | $-(CH_2)_2\phi$ | $-CH_2-CH_2-CH(CH_3)-$ | $\beta$ | H |
| 244 | $-(CH_2)_2\phi$ | $-CH_2-CH_2-CH(CH_3)-$ | $\alpha$ | $CH_3$ |
| 245 | $-(CH_2)_2\phi$ | $-CH_2-CH_2-CH(CH_3)-$ | $\beta$ | $CH_3$ |
| 246 | $-(CH_2)_2\phi$ | $-CH_2-C(CH_3)_2-CH_2-$ | $\alpha$ | H |
| 247 | $-(CH_2)_2\phi$ | $-CH_2-CH(CH_3)-CHF-$ | $\alpha$ | H |
| 248 | $-(CH_2)_2\phi$ | $-CH_2CH(C_2H_5)-CH_2-$ | $\alpha$ | H |
| 249 | $-CH_2\phi$ | $-CH_2-CH(CH_3)-CH_2-$ | $\alpha$ | H |
| 250 | $-(CH_2)_2\phi$ | $-CH_2-CH(C_2H_5)-CHF-$ | $\alpha$ | H |
| 251 | $-(CH_2)_2\phi$ | $-CH_2-CH(C_3H_8)-CH_2-$ | $\alpha$ | H |
| 252 | $-(CH_2)_2\phi$ | $-CH_2-CH_2-CH(C_4H_9)-$ | $\alpha$ | H |
| 253 | $-CH_2\phi$ | $-(CH_2)_5-$ | $\alpha$ | H |
| 254 | $-CH_2\phi$ | $-(CH_2)_5-$ | $\beta$ | H |
| 255 | $-CH_2\phi$ | $-(CH_2)_5-$ | $\alpha$ | $CH_3$ |
| 256 | $-CH_2\phi$ | $-(CH_2)_5-$ | $\beta$ | $CH_3$ |

Table VI-continued

Final PGE Compound
(Formula LXXVI)

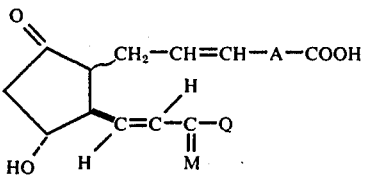

| Ex. | Q | A | M | R₃ |
|---|---|---|---|---|
| 257 | —(CH₂)₂—⌬—Cl | —CH(CH₃)— | α | H |
| 258 | —(CH₂)₃—⌬—F | —CH₂—CH(CH₃)—CH₂— | α | H |
| 259 | —(CH₂)₂—⌬(F) | —(CH₂)₃— | α | H |
| 260 | —C(CH₃)₂—CH₂φ | —CH₂—CH₂—CH(C₃H₇)— | α | H |
| 261 | —C(CH₃)₂—CH₂φ | —CH₂—CH₂—CH(C₃H₇)— | β | H |
| 262 | —C(CH₃)₂—CH₂φ | —CH₂—CH₂—CH(C₃H₇) | α | CH₃ |
| 263 | —(CH₂)₂—⌬—F | | | |
| 264 | —(CH₂)₂φ | —CH₂—CHF—CH₂— | α | H |
| 265 | —(CH₂)₂φ | —CH₂—CHF—CH₂— | α | CH₃ |
| 266 | —(CH₂)₂φ | —(CH₂)₃—CF₂— | α | H |
| 267 | —(CH₂)₂φ | —(CH₂)₄—CF₂—CF₂— | α | H |
| 268 | —(CH₂)₂φ | —(CH₂)₃—CH₂—C(CH₃)₂— | α | H |

Following the procedure of Examples 183–268, but replacing the optically active compound of the Formula LXXVII of each example by a racemic mixture of that compound and the mirror image thereof, there is obtained the corresponding racemic mixture for each Example.

The embodiments of the invention in which as exclusive property or privilege is claimed are defined as follows:

1. An optically active compound of the formula

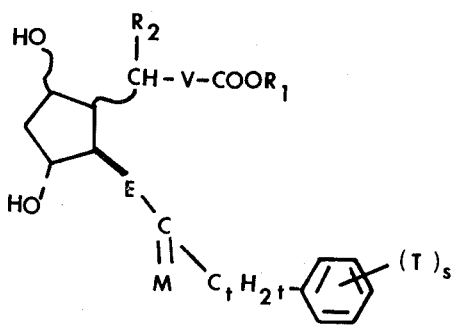

or a racemic compound of that formula and the mirror image thereof, wherein E is -CH₂CHR₄- or trans-CH=CR₄-: wherein R₁ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl-substituted with one, 2, or 3 chloro or alkyl or one to 4 carbon atoms, inclusive, or ethyl substituted in the β-position with 3 chloro; wherein M is

or

wherein R₂, R₃, and R₄ are hydrogen or alkyl of one to 4 carbon atoms, inclusive; wherein C₁H₂₁ represents a valence bond or alkylene of one to 10 carbon atoms, inclusive, substituted with zero, one, or 2 fluoro, with one to 7 carbon atoms, inclusive, between

and the phenyl ring; wherein T is alkyl of one to 4 carbon atoms, inclusive, fluoro, chloro, trifluoromethyl, or -OR$_9$, wherein R$_9$ is hydrogen, or alkyl of one to 4 carbon atoms, inclusive, and s is zero, one, 2, or 3, with the proviso that not more than two T's are other than alkyl; wherein V is (a) alkylene of 3 to 12 carbon atoms, inclusive, substituted with zero, one, 2, 3 or 4 fluoro, with 3 to 7 carbon atoms, inclusive, between -CHR$_2$- and COOR$_1$, with the proviso that when 3 or 4 fluoro are present, they are all substituents of the carbon atoms alpha and beta to -COOR$_1$, (b) -CH=CH-A-, cis or trans, or (c) -C≡C-A-, wherein A is alkylene of one to 10 carbon atoms, inclusive, substituted with zero, one, 2, 3, or 4 fluoro, with one to 5 carbon atoms, inclusive, between =CH- (or ≡C-) and -COOR$_1$, with the proviso that when 3 or 4 fluoro are present, they are all substituents of the carbon atoms alpha and beta to -COOR$_1$, with the further proviso that when E is -CH$_2$-CHR$_4$- V is (a) above; and wherein ~ indicates attachment of the group to the cyclopentane ring in alpha or beta configuration; including the lower alkanoates thereof, and the pharmacologically acceptable salts thereof when R$_1$ is hydrogen.

2. A compound according to claim 1 wherein the group

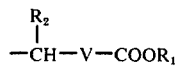

is attached to the cyclopentane ring in alpha configuration, wherein R$_2$ and R$_4$ are hydrogen, and wherein HO~ is attached to the cyclopentane ring in alpha configuration.

3. 2a,2b-Dihomo-17-phenyl-18,19,20-trinor-PGF$_{2\alpha}$, a compound according to claim 2.

4. 2a,2b-Dihomo-17-phenyl-18,19,20-trinor-PGF$_{2\alpha}$, methyl ester, a compound according to claim 2.

5. 17-Phenyl-2,18,19,20-tetranor-PGF$_{2\alpha}$, methyl ester, a compound according to claim 2.

6. A compound according to claim 2 wherein V is (a) -(CH$_2$)$_a$-X-, (b) -CH=CH-(CH$_2$)$_b$-X-, or (c) -C≡C-(CH$_2$)$_b$-X-, wherein a is one, 2, 3, 4, or 5, b is zero, one, 2, or 3, and X is ethylene substituted by one, 2, 3, or 4 fluoro, methyl, or ethyl, or by one alkyl of 3 to 4 carbon atoms.

7. A compound according to claim 6 wherein a is 3 and b is one.

8. 2,2-Difluoro-17-phenyl-18,19,20-trinor-PGF$_{2\alpha}$, methyl ester, a compound according to claim 7.

9. 3-Methyl-17-phenyl-18,19,20-trinor-PGF$_{2\alpha}$, methyl ester, compounds according to claim 7.

10. 15(S)-15-Methyl-2,2-difluoro-17-phenyl-18,19,20-trinor-PGF$_{2\alpha}$, methyl ester, a compound according to claim 7.

11. A compound according to claim 2 wherein V is (a) alkylene of 3 to 12 carbon atoms, inclusive, substituted with zero, one, 2, 3, or 4 fluoro, with 5 carbon atoms in the chain between -CHR$_2$- and -COOR$_1$, (b) -CH=CH-A-, cis or trans, or (c) -C≡C-A-, wherein A is alkylene of one to 10 carbon atoms, inclusive, substituted with zero, one, 2, 3, or 4 fluoro, with 3 carbon atoms in the chain between =CH- (or ≡C-) and -COOR$_1$.

12. A compound according to claim 11 wherein C$_t$H$_{2t}$ is limited to one to 4 carbon atoms in the chain between

and the phenyl ring.

13. A compound according to claim 12 wherein V is alkylene of 3 to 12 carbon atoms, inclusive, substituted with zero, one, 2, 3, or 4 fluoro, with 5 carbon atoms in the chain between -CHR$_2$- and -COOR$_1$; and wherein E is trans-CH=CH-.

14. A compound according to claim 13 wherein M is

15. A compound according to claim 14 wherein R$_3$ is hydrogen.

16. A compound according to claim 15 wherein C$_t$H$_{2t}$ is methylene.

17. A compound according to claim 16 wherein R$_1$ is hydrogen, and the pharmacologically acceptable salts thereof.

18. 16-Phenyl-17,18,19,20-tetranor-PGF$_{1\alpha}$, a compound according to claim 17.

19. A compound according to claim 16 wherein R$_1$ is alkyl of one to 8 carbon atoms, inclusive.

20. 16-Phenyl-17,18,19,20-tetranor-PGF$_{1\alpha}$, methyl ester, a compound according to claim 19.

21. A compound according to claim 15 wherein C$_t$H$_{2t}$ is ethylene.

22. A compound according to claim 21 wherein R$_1$ is hydrogen, and the pharmacologically acceptable salts thereof.

23. 17-Phenyl-18,19,20-trinor-PGF$_{1\alpha}$, a compound according to claim 22.

24. A compound according to claim 21 wherein R$_1$ is alkyl of one to 8 carbon atoms, inclusive.

25. 17-Phenyl-18,19,20-trinor-PGF$_{1\alpha}$, methyl ester, a compound according to claim 24.

26. A compound according to claim 15 wherein C$_t$H$_{2t}$ is

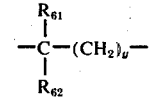

wherein g is zero, one, 2, or 3, and wherein R$_{61}$ and R$_{62}$ are hydrogen, alkyl of one to 4 carbon atoms, inclusive, or fluoro, being the same or different, with the proviso that R$_{62}$ is fluoro only when R$_{61}$ is hydrogen or fluoro, and with the further proviso that R$_{61}$ and R$_{62}$ are not both hydrogen.

27. A compound according to claim 26 wherein R$_{61}$ and R$_{62}$ are alkyl of one to 4 carbon atoms, inclusive.

28. A compound according to claim 27 wherein C$_t$H$_{2t}$ is -C(CH$_3$)$_2$-CH$_2$-.

29. A compound according to claim 28 wherein R$_1$ is hydrogen, and the pharmacologically acceptable salts thereof.

30. 16,16-Dimethyl-17-phenyl-18,19,20-trinor-PGF$_{1\alpha}$, a compound according to claim 29.

31. A compound according to claim 28 wherein $R_1$ is alkyl of one to 8 carbon atoms, inclusive.

32. 16,16-Dimethyl-17-phenyl-18,19,20-trinor-$PGF_{1\alpha}$, methyl ester, a compound according to claim 31.

33. A compound according to claim 15 wherein $C_tH_{2t}$ is trimethylene.

34. A compound according to claim 33 wherein $R_1$ is hydrogen, and the pharmacologically acceptable salts thereof.

35. 18-Phenyl-19,20-dinor-$PGF_{1\alpha}$, a compound according to claim 34.

36. A compound according to claim 33 wherein $R_1$ is alkyl of one to 8 carbon atoms, inclusive.

37. 18-Phenyl-19,20-dinor-$PGF_{1\alpha}$, methyl ester, a compound according to claim 36.

38. A compound according to claim 14 wherein $R_3$ is methyl.

39. A compound according to claim 38 wherein $C_tH_{2t}$ is methylene.

40. A compound according to claim 39 wherein $R_1$ is hydrogen and the pharmacologically acceptable salts thereof.

41. 15(S)-15-Methyl-16-phenyl-17,18,19,20-tetranor-$PGF_{1\alpha}$, a compound according to claim 40.

42. A compound according to claim 39 wherein $R_1$ is alkyl of one to 8 carbon atoms, inclusive.

43. 15(S)-15-Methyl-16-phenyl-17,18,19,20-tetranor-$PGF_{1\alpha}$, methyl ester, a compound according to claim 42.

44. A compound according to claim 38 wherein $C_tH_{2t}$ is ethylene.

45. A compound according to claim 44 wherein $R_1$ is hydrogen; and the pharmacologically acceptable salts thereof.

46. 15(S)-15-Methyl-17-phenyl-18,19,20-trinor-$PGF_{1\alpha}$, a compound according to claim 45.

47. A compound according to claim 44 wherein $R_1$ is alkyl of one to 8 carbon atoms, inclusive.

48. 15(S)-15-Methyl-17-phenyl-18,19,20-trinor-$PGF_{1\alpha}$, methyl ester, a compound according to claim 47.

49. A compound according to claim 38 wherein $C_tH_{2t}$ is trimethylene.

50. A compound according to claim 49 wherein $R_1$ is hydrogen, and the pharmacologically acceptable salts thereof.

51. 15(S)-15-Methyl-18-phenyl-19,20-dinor-$PGF_{1\alpha}$, a compound according to claim 50.

52. A compound according to claim 49 wherein $R_1$ is alkyl of one to 8 carbon atoms, inclusive.

53. 15(S)-15-Methyl-18-phenyl-19,20-dinor-$PGF_{1\alpha}$, a compound according to claim 52.

54. A compound according to claim 13 wherein M is

55. A compound according to claim 54 wherein $R_3$ is hydrogen.

56. A compound according to claim 54 wherein $R_3$ is methyl.

57. A compound according to claim 56 wherein $C_tH_{2t}$ is ethylene.

58. A compound according to claim 57 wherein $R_1$ is hydrogen, and the pharmacologically acceptable salts thereof.

59. 15(R)-15-Methyl-17-phenyl-18,19,20-trinor-$PGF_{1\alpha}$, a compound according to claim 58.

60. A compound according to claim 57 wherein $R_1$ is alkyl of one to 8 carbon atoms, inclusive.

61. 15(R)-15-Methyl-17-phenyl-18,19,20-trinor-$PGF_{1\alpha}$, methyl ester, a compound according to claim 60.

62. A compound according to claim 12 wherein V is -CH=CH-A-, cis or trans, wherein A is alkylene of one to 10 carbon atoms, inclusive, substituted with zero, one, 2, 3, or 4 fluoro, with 3 carbon atoms in the chain between =CH- and -$COOR_1$; and wherein E is trans-CH=CH-.

63. A compound according to claim 62 wherein M is

64. A compound according to claim 63 wherein $R_3$ is hydrogen.

65. A compound according to claim 64 wherein $C_tH_{2t}$ is methylene.

66. A compound according to claim 65 wherein $R_1$ is hydrogen, and the pharmacologically acceptable salts thereof.

67. 16-Phenyl-17,18,19,20-tetranor $PGF_{2\alpha}$, a compound according to claim 66.

68. A compound according to claim 65 wherein $R_1$ is alkyl of one to 8 carbon atoms, inclusive.

69. 16-Phenyl-17,18,19,20-tetranor-$PGF_{2\alpha}$, methyl ester, a compound according to claim 68.

70. A compound according to claim 64 wherein $C_tH_{2t}$ is ethylene.

71. A compound according to claim 70 wherein $R_1$ is hydrogen, and the phrmacologically acceptable salts thereof.

72. 17-Phenyl-18,19,20-trinor-$PGF_{2\alpha}$, a compound according to claim 71.

73. 17-(p-Chlorophenyl)-18,19,20-trinor-$PGF_{2\alpha}$, a compound according to claim 71.

74. 17-(p-Fluorophenyl)-18,19,20-trinor-$PGF_{2\alpha}$, a compound according to claim 71.

75. A compound according to claim 70 wherein $R_1$ is alkyl of one to 8 carbon atoms, inclusive.

76. 17-Phenyl-18,19,20-trinor-$PGF_{2\alpha}$, methyl ester, a compound according to claim 75.

77. 17-(p-Chlorophenyl)-18,19,20-trinor-$PGF_{2\alpha}$, methyl ester, a compound according to claim 75.

78. 17-(p-Chlorophenyl)-18,19,20-trinor-$PGF_{2\alpha}$, ethyl ester, a compound according to claim 75.

79. A compound according to claim 64 wherein $C_tH_{2t}$ is

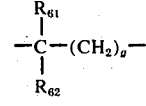

wherein g is zero, one, 2, or 3, and wherein $R_{61}$ and $R_{62}$ are hydrogen, alkyl of one to 4 carbon atoms, inclusive, or fluoro, being the same or different, with the proviso that $R_{62}$ is fluoro only when $R_{61}$ is hydrogen or fluoro, and with the further proviso that $R_{61}$ and $R_{62}$ are not both hydrogen.

80. A compound according to claim 79 wherein $R_{61}$ and $R_{62}$ are alkyl of one to 4 carbon atoms, inclusive.

81. A compound according to claim 80 wherein $C_tH_{2t}$ is $-C(CH_3)_2-CH_2-$.

82. A compound according to claim 81 wherein $R_1$ is hydrogen, and the pharmacologically acceptable salts thereof.

83. 16,16-Dimethyl-17-phenyl-18,19,20-trinor-$PGF_{2\alpha}$, a compound according to claim 82.

84. A compound according to claim 81 wherein $R_1$ is alkyl of one to 8 carbon atoms, inclusive.

85. 16,16-Dimethyl-17-phenyl-18,19,20-trinor-$PGF_{2\alpha}$, methyl ester, a compound according to claim 84.

86. A compound according to claim 64 wherein $C_tH_{2t}$ is trimethylene.

87. A compound according to claim 86 wherein $R_1$ is hydrogen, and the pharmacologically acceptable salts thereof.

88. 18-Phenyl-19,20-dinor-$PGF_{2\alpha}$, a compound according to claim 87.

89. A compound according to claim 86 wherein $R_1$ is alkyl of one to 8 carbon atoms, inclusive.

90. 18-Phenyl-19,20-dinor-$PGF_{2\alpha}$, methyl ester, a compound according to claim 89.

91. A compound according to claim 63 wherein $R_3$ is methyl.

92. A compound according to claim 91 wherein $C_tH_{2t}$ is methylene.

93. A compound according to claim 92 wherein $R_1$ is hydrogen, and the pharmacologically acceptable salts thereof.

94. 15(S)-15-Methyl-16-phenyl-17,18,19,20-tetranor-$PGF_{2\alpha}$, a compound according to claim 93.

95. A compound according to claim 92 wherein $R_1$ is alkyl of one to 8 carbon atoms, inclusive.

96. 15(S)-15-Methyl-16-phenyl-17,18,19,20-tetranor-$PGF_{2\alpha}$, methyl ester, a compound according to claim 95.

97. A compound according to claim 91 wherein $C_tH_{2t}$ is ethylene.

98. A compound according to claim 97 wherein $R_1$ is hydrogen, and the pharmacologically acceptable salts thereof.

99. 15(S)-15-Methyl-17-phenyl-18,19,20-trinor-$PGF_{2\alpha}$, a compound according to claim 98.

100. A compound according to claim 97 wherein $R_1$ is alkyl of one to 8 carbon atoms, inclusive.

101. 15(S)-15-Methyl-17-phenyl-18,19,20-trinor-$PGF_{2\alpha}$, methyl ester, a compound according to claim 100.

102. A compound according to claim 91 wherein $C_tH_{2t}$ is trimethylene.

103. A compound according to claim 102 wherein $R_1$ is hydrogen, and the pharmacologically acceptable salts thereof.

104. 15(S)-15-Methyl-18-phenyl-19,20-dinor-$PGF_{2\alpha}$, a compound according to claim 103.

105. A compound according to claim 102 wherein $R_1$ is alkyl of one to 8 carbon atoms, inclusive.

106. 15(S)-15-Methyl-18-phenyl-19,20-dinor-$PGF_{2\alpha}$, methyl ester, a compound according to claim 105.

107. A compound according to claim 62 wherein M is

108. A compound according to claim 107 wherein $R_3$ is hydrogen.

109. A compound according to claim 107 wherein $R_3$ is methyl.

110. A compound according to claim 109 wherein $C_tH_{2t}$ is ethylene.

111. A compound according to claim 110 wherein $R_1$ is hydrogen, and the pharmacologically acceptable salts thereof.

112. 15(R)-15-Methyl-17-phenyl-18,19,20-trinor-$PGF_{2\alpha}$, a compound according to claim 111.

113. A compound according to claim 110 wherein $R_1$ is alkyl of one to 8 carbon atoms, inclusive.

114. 15(R)-15-Methyl-17-phenyl-18,19,20-trinor-$PGF_{2\alpha}$, methyl ester, a compound according to claim 113.

115. A compound according to claim 12 wherein V is $-C\equiv C-A-$, wherein A is alkylene of one to 10 carbon atoms, inclusive, substituted with zero, one, 2, 3, or 4 fluoro, with 3 carbon atoms in the chain between $-C\equiv$ and $-COOR_1$; and wherein E is trans-$CH=CH-$.

116. A compound according to claim 115 wherein M is

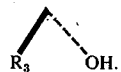

117. A compound according to claim 116 wherein $R_3$ is hydrogen.

118. A compound according to claim 117 wherein $C_tH_{2t}$ is ethylene.

119. A compound according to claim 118 wherein $R_1$ is hydrogen, and the pharmacologically acceptable salts thereof.

120. 5,6-Didehydro-17-phenyl-18,19,20-trinor-$PGF_{2\alpha}$, a compound according to claim 119.

121. A compound according to claim 118 wherein $R_1$ is alkyl of one to 8 carbon atoms, inclusive.

122. 5,6-Didehydro-17-phenyl-18,19,20-trinor-$PGF_{2\alpha}$, methyl ester, a compound according to claim 121.

123. A compound according to claim 116 wherein $R_3$ is methyl.

124. A compound according to claim 123 wherein $C_tH_{2t}$ is ethylene.

125. A compound according to claim 124 wherein $R_1$ is hydrogen, and the pharmacologically acceptable salts thereof.

126. 5,6-Didehydro-15(S)-15-methyl-17-phenyl-18,19,20-trinor-$PGF_{2\alpha}$, a compound according to claim 125.

127. A compound according to claim 115 wherein M is

128. A compound according to claim 12 wherein V is alkylene of 3 to 12 carbon atoms, inclusive, substituted with zero, one, 2, 3, or 4 fluoro, with 5 carbon atoms in the chain between $-CHR_2-$ and $-COOR_1$; and wherein E is $-CH_2CH_2-$.

129. A compound according to claim 128 wherein M is

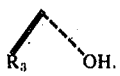

130. A compound according to claim 129 wherein $R_3$ is hydrogen.

131. A compound according to claim 130 wherein $C_tH_{2t}$ is ethylene.

132. A compound according to claim 131 wherein $R_1$ is hydrogen, and the pharmacologically acceptable salts thereof.

133. 13,14-Dihydro-17-phenyl-18,19,20-trinor-$PGF_{1\alpha}$, a compound according to claim 132.

134. A compound according to claim 131 wherein $R_1$ is alkyl of one to 8 carbon atoms, inclusive.

135. 13,14-Dihydro-17-phenyl-18,19,20-trinor-$PGF_{1\alpha}$, methyl ester, a compound according to claim 134.

136. A compound according to claim 129 wherein $R_3$ is methyl.

137. A compound according to claim 136 wherein $C_tH_{2t}$ is ethylene.

138. A compound according to claim 137 wherein $R_1$ is hydrogen, and the pharmacologically acceptable salts thereof.

139. 13,14-Dihydro-15(S)-15-methyl-17-phenyl-18,19,20-trinor-$PGF_{1\alpha}$, a compound according to claim 138.

140. A compound according to claim 128 wherein M is

141. A compound according to claim 1 wherein the group

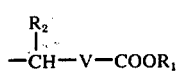

is attached to the cyclopentane ring in alpha configuration, wherein $R_2$ and $R_4$ are hydrogen, and wherein HO~ is attached to the cyclopentane ring in beta configuration.

142. A compound according to claim 141 wherein V is (a) -$(CH_2)_a$-X, (b) -CH=CH-$(CH_2)_b$-X-, or (c) -C≡C-$(CH_2)_b$-X-, wherein a is one, 2, 3, 4, or 5, b is zero, one, 2, or 3, and X is ethylene substituted by one, 2, 3, or 4 fluoro, methyl, or ethyl, or by one alkyl of 3 or 4 carbon atoms.

143. A compound according to claim 141 wherein V is (a) alkylene of 3 to 12 carbon atoms, inclusive, substituted with zero, one, 2, 3, or 4 fluoro, with 5 carbon atoms in the chain between -$CHR_2$- and -$COOOR_1$, (b) -CH=CH-A-, cis or trans, or (c) -C≡C-A-, wherein A is alkylene of one to 10 carbon atoms, inclusive, substituted with zero, one, 2, 3, or 4 fluoro, with 3 carbon atoms in the chain between =CH- (or ≡C-) and -$COOR_1$.

144. A compound according to claim 143 wherein $C_tH_{2t}$ is limited to one to 4 carbon atoms in the chain between

and the phenyl ring.

145. A compound according to claim 144 wherein V is alkylene of 3 to 12 carbon atoms, inclusive, substituted with zero, one, 2, 3, or 4 fluoro, with 5 carbon atoms in the chain between -$CHR_2$- and -$COOR_1$; and wherein E is trans-CH=CH-.

146. A compound according to claim 145 wherein M is

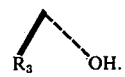

147. A compound according to claim 146 wherein $R_3$ is hydrogen.

148. A compound according to claim 147 wherein $C_tH_{2t}$ is methylene.

149. A compound according to claim 148 wherein $R_1$ is hydrogen, and the pharmacologically acceptable salts thereof.

150. 16-Phenyl-17,18,19,20-tetranor-$PGF_{1\beta}$, a compound according to claim 149.

151. A compound according to claim 148 wherein $R_1$ is alkyl of one to 8 carbon atoms, inclusive.

152. 16-Phenyl-17,18,19,20-tetranor-$PGF_{1\beta}$, methyl ester, a compound according to claim 151.

153. A compound according to claim 147 wherein $C_tH_{2t}$ is ethylene.

154. A compound according to claim 153 wherein $R_1$ is hydrogen, and the pharmacologically acceptable salts thereof.

155. 17-Phenyl-18,19,20-trinor-$PGF_{1\beta}$, a compound according to claim 154.

156. A compound according to claim 153 wherein $R_1$ is alkyl of one to 8 carbon atoms, inclusive.

157. 17-Phenyl-18,19,20-trinor-$PGB_{1\beta}$, methyl ester, a compound according to claim 156.

158. A compound according to claim 147 wherein $C_tH_{2t}$ is

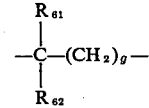

wherein g is zero, one, 2, or 3, and wherein $R_{61}$ and $R_{62}$ are hydrogen, alkyl of one to 4 carbon atoms, inclusive, or fluoro, being the same or different, with the proviso that $R_{62}$ is fluoro only when $R_{61}$ is hydrogen or fluoro, and with the further proviso that $R_{61}$ and $R_{62}$ are not both hydrogen.

159. A compound according to claim 158 wherein $R_{61}$ and $R_{62}$ are alkyl of one to 4 carbon atoms, inclusive.

160. A compound according to claim 159 wherein $C_tH_{2t}$ is -$C(CH_3)_2$-$CH_2$-.

161. A compound according to claim 160 wherein $R_1$ is hydrogen, and the pharmacologically acceptable salts thereof.

162. 16,16-Dimethyl-17-phenyl-18,19,20-trinor-$PGF_{1\beta}$, a compound according to claim 161.

163. A compound according to claim 160 wherein $R_1$ is alkyl of one to 8 carbon atoms, inclusive.

164. 16,16-Dimethyl-17-phenyl-18,19,20-trinor-PGF$_{1\beta}$, methyl ester, a compound according to claim 163.

165. A compound according to claim 147 wherein C$_t$H$_{2t}$ is trimethylene.

166. A compound according to claim 165 wherein R$_1$ is hydrogen, and the pharmacologically acceptable salts thereof.

167. 18-Phenyl-19,20-dinor-PGF$_{1\beta}$, a compound according to claim 166.

168. A compound according to claim 165 wherein R$_1$ is alkyl of one to 8 carbon atoms, inclusive.

169. 18-Phenyl-19,20-dinor-PGF$_{1\beta}$, methyl ester, a compound according to claim 168.

170. A compound according to claim 146 wherein R$_3$ is methyl.

171. A compound according to claim 170 wherein C$_t$H$_{2t}$ is methylene.

172. A compound according to claim 171 wherein R$_1$ is hydrogen and the pharmacologically acceptable salts thereof.

173. 15(S)-15-Methyl-16-phenyl-17,18,19,20-tetranor-PGF$_{1\beta}$, a compound according to claim 172.

174. A compound according to claim 171 wherein R$_1$ is alkyl of one to 8 carbon atoms, inclusive.

175. 15(S)-15-Methyl-16-phenyl-17,18,19,20-tetranor-PGF$_{1\beta}$, methyl ester, a compound according to claim 174.

176. A compound according to claim 170 wherein C$_t$H$_{2t}$ is ethylene.

177. A compound according to claim 176 wherein R$_1$ is hydrogen; and the pharmacologically acceptable salts thereof.

178. 15(S)-15-Methyl-17-phenyl-18,19,20-trinor-PGF$_{1\beta}$, a compound according to claim 177.

179. A compound according to claim 176 wherein R$_1$ is alkyl of one to 8 carbon atoms, inclusive.

180. 15(S)-15-Methyl-17-phenyl-18,19,20-trinor-PGF$_{1\beta}$, methyl ester, a compound according to claim 179.

181. A compound according to claim 170 wherein C$_t$H$_{2t}$ is trimethylene.

182. A compound according to claim 181 wherein R$_1$ is hydrogen, and the pharmacologically acceptable salts thereof.

183. 15(S)-15-Methyl-18-phenyl-19,20-dinor-PGF$_{1\beta}$, a compound according to claim 182.

184. A compound according to claim 181 wherein R$_1$ is alkyl of one to 8 carbon atoms, inclusive.

185. 15(S)-15-Methyl-18-phenyl-19,20-dinor-PGF$_{1\beta}$, methyl ester, a compound according to claim 184.

186. A compound according to claim 145 wherein M is

187. A compound according to claim 186 wherein R$_3$ is hydrogen.

188. A compound according to claim 186 wherein R$_3$ is methyl.

189. A compound according to claim 188 wherein C$_t$H$_{2t}$ is ethylene.

190. A compound according to claim 189 wherein R$_1$ is hydrogen, and the pharmacologically acceptable salts thereof.

191. 15(R)-15-Methyl-17-phenyl-18,19,20-trinor-PGF$_{1\beta}$, a compound according to claim 190.

192. A compound according to claim 189 wherein R$_1$ is alkyl of one to 8 carbon atoms, inclusive.

193. 15(R)-15-Methyl-17-phenyl-18,19,20-trinor-PGF$_{1\beta}$, methyl ester, a compound according to claim 192.

194. A compound according to claim 144 wherein V is -CH=CH-A-, cis or trans, wherein A is alkylene of one to 10 carbon atoms, inclusive, substituted with zero, one, 2, 3, or 4 fluoro, with 3 carbon atoms in the chain between =CH- and -COOR$_1$; and wherein E is trans-CH=CH-.

195. A compound according to claim 194 wherein M is

196. A compound according to claim 195 wherein R$_3$ is hydrogen.

197. A compound according to claim 196 wherein C$_t$H$_{2t}$ is methylene.

198. A compound according to claim 197 wherein R$_1$ is hydrogen, and the pharmacologically acceptable salts thereof.

199. 16-Phenyl-17,18,19,20-tetranor-PGF$_{2\beta}$, a compound according to claim 198.

200. A compound according to claim 197 wherein R$_1$ is alkyl of one to 8 carbon atoms, inclusive.

201. 16-Phenyl-17,18,19,20-tetranor-PGF$_{2\beta}$, methyl ester, a compound according to claim 200.

202. A compound according to claim 196 wherein C$_t$H$_{2t}$ is ethylene.

203. A compound according to claim 202 wherein R$_1$ is hydrogen, and the pharmacologically acceptable salts thereof.

204. 17-Phenyl-18,19,20-trinor-PGF$_{2\beta}$, a compound according to claim 203.

205. A compound according to claim 202 wherein R$_1$ is alkyl of one to 8 carbon atoms, inclusive.

206. 17-Phenyl-18,19,20-trinor-PGF$_{2\beta}$, methyl ester, a compound according to claim 205.

207. A compound according to claim 196 wherein C$_t$H$_{2t}$ is

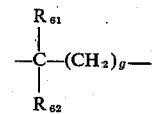

wherein g is zero, one, 2, or 3, and wherein R$_{61}$ and R$_{62}$ are hydrogen, alkyl of one to 4 carbon atoms, inclusive, or fluoro, being the same or different, with the proviso that R$_{62}$ is fluoro only when R$_{61}$ is hydrogen or fluoro, and with the further proviso that R$_{61}$ and R$_{62}$ are not both hydrogen.

208. A compound according to claim 207 wherein R$_{61}$ and R$_{62}$ are alkyl of one to 4 carbon atoms, inclusive.

209. A compound according to claim 208 wherein C$_t$H$_{2t}$ is -C(CH$_3$)$_2$-CH$_2$-.

210. A compound according to claim 196 wherein C$_t$H$_{2t}$ is trimethylene.

211. A compound according to claim 210 wherein R$_1$ is hydrogen, and the pharmacologically acceptable salts thereof.

212. 18-Phenyl-19,20-dinor-PGF$_{2\beta}$, a compound according to claim 209.

213. A compound according to claim 210 wherein R$_1$ is alkyl of one to 8 carbon atoms, inclusive.

214. 18-Phenyl-19,20-dinor-PGF$_{2\beta}$, methyl ester, a compound according to claim 213.

215. A compound according to claim 195 wherein R$_3$ is methyl.

216. A compound according to claim 215 wherein C$_t$H$_{2t}$ is methylene.

217. A compound according to claim 216 wherein R$_1$ is hydrogen, and the pharmacologically acceptable salts thereof.

218. 15(S)-15-Methyl-16-phenyl-17,18,19,20-tetranor-PGF$_{2\beta}$, a compound according to claim 217.

219. A compound according to claim 216 wherein R$_1$ is alkyl of one to 8 carbon atoms, inclusive.

220. 15(S)-15-Methyl-16-phenyl-17,18,19,20-tetranor-PGF$_{2\beta}$, methyl ester, a compound according to claim 219.

221. A compound according to claim 215 wherein C$_t$H$_{2t}$ is ethylene.

222. A compound according to claim 221 wherein R$_1$ is hydrogen, and the pharmacologically acceptable salts thereof.

223. 15(S)-15-Methyl-17-phenyl-18,19,20-tetranor-PGF$_{2\beta}$, a compound according to claim 222.

224. A compound according to claim 221 wherein R$_1$ is alkyl of one to 8 carbon atoms, inclusive.

225. 15(S)-17-phenyl-18,19,20-trinor-PGF$_{2\beta}$, methyl ester, a compound according to claim 224.

226. A compound according to claim 215 wherein C$_t$H$_{2t}$ is trimethylene.

227. A compound according to claim 226 wherein R$_1$ is hydrogen, and the pharmacologically acceptable salts thereof.

228. 15(S)-15-Methyl-18-phenyl-19,20-dinor-PGF$_{2\beta}$, a compound according to claim 227.

229. A compound according to claim 226 wherein R$_1$ is alkyl of one to 8 carbon atoms, inclusive.

230. 15(S)-15-Methyl-18-phenyl-19,20-dinor-PGF$_{2\beta}$, methyl ester, a compound according to claim 229.

231. A compound according to claim 194 wherein M is

232. A compound according to claim 231 wherein R$_3$ is hydrogen.

233. A compound according to claim 231 wherein R$_3$ is methyl.

234. A compound according to claim 233 wherein C$_t$H$_{2t}$ is ethylene.

235. A compound according to claim 234 wherein R$_1$ is hydrogen, and the pharmacologically acceptable salts thereof.

236. 15(R)-15-Methyl-17-phenyl-18,19,20-trinor-PGF$_{2\beta}$, a compound according to claim 235.

237. A compound according to claim 234 wherein R$_1$ is alkyl of one to 8 carbon atoms, inclusive.

238. 15(R)-15-Methyl-17-phenyl-18,19,20-trinor-PGF$_{2\beta}$, methyl ester, a compound according to claim 237.

239. A compound according to claim 144 wherein V is -C≡C-A-, wherein A is alkylene of one to 10 carbon atoms, inclusive, substituted with zero, one, 2, 3, or 4 fluoro, with 3 carbon atoms in the chain between ≡C- and -COOR$_1$; and wherein E is trans-CH=CH-.

240. A compound according to claim 239 wherein M is

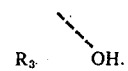

241. A compound according to claim 240 wherein R$_3$ is hydrogen.

242. A compound according to claim 241 wherein C$_t$H$_{2t}$ is ethylene.

243. A compound according to claim 242 wherein R$_1$ is hydrogen, and the pharmacologically acceptable salts thereof.

244. 5,6-Didehydro-17-phenyl-18,19,20-trinor-PGF$_{2\beta}$, a compound according to claim 243.

245. A compound according to claim 242 wherein R$_1$ is alkyl of one to 8 carbon atoms, inclusive.

246. 5,6-Didehydro-17-phenyl-18,19,20-trinor-PGF$_{2\beta}$, methyl ester, a compound according to claim 245.

247. A compound according to claim 239 wherein M is

248. A compound according to claim 144 wherein V is alkylene of 3 to 12 carbon atoms, inclusive, substituted with zero, one, 2, 3, or 4 fluoro, with 5 carbon atoms in the chain between -CHR$_2$- and -COOR$_1$; and wherein E is -CH$_2$CH$_2$-.

249. A compound according to claim 248 wherein M is

250. A compound according to claim 249 wherein R$_3$ is hydrogen.

251. A compound according to claim 250 wherein C$_t$H$_{2t}$ is ethylene.

252. A compound according to claim 251 wherein R$_1$ is hydrogen, and the pharmacologically acceptable salts thereof.

253. 13,14-Dihydro-17-phenyl-18,19,20-trinor-PGF$_{1\beta}$, a compound according to claim 252.

254. A compound according to claim 251 wherein R$_1$ is alkyl of one to 8 carbon atoms, inclusive.

255. 13,14-Dihydro-17-phenyl-18,19,20-trinor-PGF$_{1\beta}$, methyl ester, a compound according to claim 254.

256. A compound according to claim 249 wherein R$_3$ is methyl.

257. A compound according to claim 256 wherein C$_t$H$_{2t}$ is ethylene.

258. A compound according to claim 257 wherein R$_1$ is hydrogen, and the pharmacologically acceptable salts thereof.

259. 13,14-Dihydro-15(S)-15-methyl-17-phenyl-18,19,20-trinor-PGF$_{1\beta}$, a compound according to claim 258.

260. A compound according to claim 248 wherein M is

* * * * *